United States Patent [19]
Kojima et al.

[11] Patent Number: 6,040,160
[45] Date of Patent: Mar. 21, 2000

[54] METHOD OF PRODUCING L-LYSINE BY FERMENTATION

[75] Inventors: Hiroyuki Kojima; Yuri Ogawa; Kazue Kawamura; Konosuke Sano, all of Kawasaki, Japan

[73] Assignee: Ajinomoto Co., Inc., Tokyo, Japan

[21] Appl. No.: 08/648,010

[22] PCT Filed: Nov. 28, 1994

[86] PCT No.: PCT/JP94/01994

§ 371 Date: May 29, 1996

§ 102(e) Date: May 29, 1996

[87] PCT Pub. No.: WO95/16042

PCT Pub. Date: Jun. 15, 1995

[30] Foreign Application Priority Data

Dec. 8, 1993 [JP] Japan ..................................... 5-308397

[51] Int. Cl.[7] .............................. C12P 13/08; C12N 1/20; C12N 15/00; C07H 21/04
[52] U.S. Cl. ................. 435/115; 435/252.3; 435/254.11; 435/320.1; 435/325; 536/23.2
[58] Field of Search ................................ 435/115, 252.3, 435/254.11, 320.1, 325; 536/23.2

[56] References Cited

U.S. PATENT DOCUMENTS

| | | | |
|---|---|---|---|
| 5,258,300 | 11/1993 | Glassman et al. | 435/240.4 |
| 5,367,110 | 11/1994 | Galili et al. | 800/205 |
| 5,545,545 | 8/1996 | Gengenbach et al. | 435/172.3 |

FOREIGN PATENT DOCUMENTS

| | | | |
|---|---|---|---|
| 0 435 132 | 7/1991 | European Pat. Off. . | |
| 19190 | 9/1993 | WIPO | 536/23.2 |
| WO 93/19190 | 9/1993 | WIPO . | |
| 11517 | 5/1994 | WIPO | 536/23.2 |
| WO 94/11517 | 5/1994 | WIPO . | |

OTHER PUBLICATIONS

M. Hermann, et al., European Journal of Biochemistry, vol. 30, pp. 100–106, "Consequences of Lysine Oversynthesis in Pseudomonas Mutants Insensitive to Feedback Inhibition. Lysine Excretion of Endogenous Induction of Lysine–Catabolic Pathway", 1972.

D.C. Bittel, et al., Am. Soc. Plant Physiologists, pp. 322–323, "Characterization of A Lysine–Intensive Form of Dihydrodipicolinate Synthase From Maize", 1992.

Valérie Frankard et al, "Two Feedback–Insensitive Enzymes of the Aspartate Pathway in *Nicotiana sylvestris*[1]", Plant Physiol., vol. 99, pp. 1285–1293, 1992.

Orit Shaul et al., "Concerted Regulation of Lysine and Threonine Synthesis in Tobacco Plants Expressing Bacterial Feedback–Insensitive Aspartate Kinase and Dihydrodipicolinate Synthase", Plant Molecular Biology., vol. 23, pp. 759–768, 1993.

Michel Cassan et al, Nucleotide Sequence of IysC Gene Encoding the Lysine–sensitive Aspartokinase III of *Escherichia coli* K12.

Journal of Bacteriology, vol. 166, No. 1, pp. 297–300, Apr. 1986, F. Richaud, et al., "Chromosomal Location and Nucleotide Sequence of the Escherichia Coli dapA Gene".

Brock et al. (1973) Modification of amino acid composition of higher plants by mutation and selection. Caplus Access No: 1974:488102 Caplus, May 1973.

*Primary Examiner*—Bradley Sisson
*Assistant Examiner*—Einar Stole
*Attorney, Agent, or Firm*—Oblon, Spivak, McClelland, Maier & Neustadt, P.C.

[57] ABSTRACT

A bacterium belonging to the genus Escherichia, which is transformed by introducing, into its cells, a DNA coding for a dihydrodipicolinate synthase originating from a bacterium belonging to the genus Escherichia having mutation to desensitize feedback inhibition by L-lysine and a DNA coding for an aspartokinase III originating from a bacterium belonging to the genus Escherichia having mutation to desensitize feedback inhibition by L-lysine; preferably a bacterium belonging to the genus Escherichia in which a dihydrodipicolinate reductase gene and a diaminopimelate dehydrogenase gene originating from *Brevibacterium lactofermentum* (or a succinyldiaminopimelate transaminase gene and a succinyldiaminopimelate deacylase gene) are further enhanced, is cultivated in an appropriate medium, L-lysine is produced and accumulated in a culture thereof, and L-lysine is collected from the culture.

22 Claims, 18 Drawing Sheets

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:1:

CCGCAACTAC TGACATGACG                                                        20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:2:

AGTAAGCCAT CAAATCTCCC                                                        20

(2) INFORMATION FOR SEQ ID NO:3:

(i) SEQUENCE CHARACTERISTICS:
      (A) LENGTH: 1197 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: ESCHERICHIA COLI
      (B) STRAIN: MC1061

(ix) FEATURE:
      (A) NAME/KEY: prim_transcript
      (B) LOCATION: 248
      (D) OTHER INFORMATION: /note= "IDENTIFICATION METHOD: E"

(ix) FEATURE:
      (A) NAME/KEY: CDS
      (B) LOCATION: 272..1150
      (D) OTHER INFORMATION: /note= "IDENTIFICATION METHOD: E"

(ix) FEATURE:

(A) NAME/KEY: primer_bind
        (B) LOCATION: 27..46
        (D) OTHER INFORMATION: /note= "IDENTIFICATION METHOD: E"

(ix) FEATURE:
        (A) NAME/KEY: primer_bind
        (B) LOCATION: 1156..1175
        (D) OTHER INFORMATION: /note= "IDENTIFICATION METHOD: E"

(ix) FEATURE:
        (A) NAME/KEY: RBS
        (B) LOCATION: 261..265
        (D) OTHER INFORMATION: /note= "IDENTIFICATION METHOD: S"

(xi) SEQUENCE DESCRIPTION: SEQ ID NO:3:

```
CCAGGCGACT GTCTTCAATA TTACAGCCGC AACTACTGAC ATGACGGGTG ATGGTGTTCA      60

CAATTCCACG GCGATCGGCA CCCAACGCAG TGATCACCAG ATAATGTGTT GCGATGACAG     120

TGTCAAACTG GTTATTCCTT TAAGGGGTGA GTTGTTCTTA AGGAAAGCAT AAAAAAAACA     180

TGCATACAAC AATCAGAACG TTCTGTCTG CTTGCTTTTA ATGCCATACC AAACGTACCA     240

TTGAGACACT TGTTTGCACA GAGGATGGCC C ATG TTC ACG GGA AGT ATT GTC        292
                                  Met Phe Thr Gly Ser Ile Val
                                    1               5

GCG ATT GTT ACT CCG ATG GAT GAA AAA GGT AAT GTC TGT CGG GCT AGC       340
Ala Ile Val Thr Pro Met Asp Glu Lys Gly Asn Val Cys Arg Ala Ser
         10                  15                  20

TTG AAA AAA CTG ATT GAT TAT CAT GTC GCC AGC GGT ACT TCG GCG ATC       388
Leu Lys Lys Leu Ile Asp Tyr His Val Ala Ser Gly Thr Ser Ala Ile
 25                  30                  35

GTT TCT GTT GGC ACC ACT GGC GAG TCC GCT ACC TTA AAT CAT GAC GAA       436
Val Ser Val Gly Thr Thr Gly Glu Ser Ala Thr Leu Asn His Asp Glu
 40                  45                  50                  55

CAT GCT GAT GTG GTG ATG ATG ACG CTG GAT CTG GCT GAT GGG CGC ATT       484
His Ala Asp Val Val Met Met Thr Leu Asp Leu Ala Asp Gly Arg Ile
             60                  65                  70

CCG GTA ATT GCC GGG ACC GGC GCT AAC GCT ACT GCG GAA GCC ATT AGC       532
Pro Val Ile Ala Gly Thr Gly Ala Asn Ala Thr Ala Glu Ala Ile Ser
         75                  80                  85

CTG ACG CAG CGC TTC AAT GAC AGT GGT ATC GTC GGC TGC CTG ACG GTA       580
Leu Thr Gln Arg Phe Asn Asp Ser Gly Ile Val Gly Cys Leu Thr Val
     90                  95                 100

ACC CCT TAC TAC AAT CGT CCG TCG CAA GAA GGT TTG TAT CAG CAT TTC       628
Thr Pro Tyr Tyr Asn Arg Pro Ser Gln Glu Gly Leu Tyr Gln His Phe
105                 110                 115

AAA GCC ATC GCT GAG CAT ACT GAC CTG CCG CAA ATT CTG TAT AAT GTG       676
Lys Ala Ile Ala Glu His Thr Asp Leu Pro Gln Ile Leu Tyr Asn Val
120                 125                 130                 135

CCG TCC CGT ACT GGC TGC GAT CTG CTC CCG GAA ACG GTG GGC CGT CTG       724
Pro Ser Arg Thr Gly Cys Asp Leu Leu Pro Glu Thr Val Gly Arg Leu
                140                 145                 150

GCG AAA GTA AAA AAT ATT ATC GGA ATC AAA GAG GCA ACA GGG AAC TTA       772
Ala Lys Val Lys Asn Ile Ile Gly Ile Lys Glu Ala Thr Gly Asn Leu
        155                 160                 165

ACG CGT GTA AAC CAG ATC AAA GAG CTG GTT TCA GAT GAT TTT GTT CTG       820
Thr Arg Val Asn Gln Ile Lys Glu Leu Val Ser Asp Asp Phe Val Leu
    170                 175                 180

CTG AGC GGC GAT GAT GCG AGC GCG CTG GAC TTC ATG CAA TTG GGC GGT       868
Leu Ser Gly Asp Asp Ala Ser Ala Leu Asp Phe Met Gln Leu Gly Gly
185                 190                 195

CAT GGG GTT ATT TCC GTT ACG ACT AAC GTC GCA GCG CGT GAT ATG GCC       916
His Gly Val Ile Ser Val Thr Thr Asn Val Ala Ala Arg Asp Met Ala
200                 205                 210                 215
```

-continued

```
CAG ATG TGC AAA CTG GCA GCA GAA GAA CAT TTT GCC GAG GCA CGC GTT       964
Gln Met Cys Lys Leu Ala Ala Glu Glu His Phe Ala Glu Ala Arg Val
            220                 225                 230

ATT AAT CAG CGT CTG ATG CCA TTA CAC AAC AAA CTA TTT GTC GAA CCC      1012
Ile Asn Gln Arg Leu Met Pro Leu His Asn Lys Leu Phe Val Glu Pro
            235                 240                 245

AAT CCA ATC CCG GTG AAA TGG GCA TGT AAG GAA CTG GGT CTT GTG GCG      1060
Asn Pro Ile Pro Val Lys Trp Ala Cys Lys Glu Leu Gly Leu Val Ala
            250                 255                 260

ACC GAT ACG CTG CGC CTG CCA ATG ACA CCA ATC ACC GAC AGT GGT CGT      1108
Thr Asp Thr Leu Arg Leu Pro Met Thr Pro Ile Thr Asp Ser Gly Arg
        265                 270                 275

GAG ACG GTC AGA GCG GCG CTT AAG CAT GCC GGT TTG CTG TAA              1150
Glu Thr Val Arg Ala Ala Leu Lys His Ala Gly Leu Leu *
280                 285                 290

AGTTTAGGGA GATTTGATGG CTTACTCTGT TCAAAAGTCG CGCCTGG                  1197
```

(2) INFORMATION FOR SEQ ID NO:4:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO:4:

```
Met Phe Thr Gly Ser Ile Val Ala Ile Val Thr Pro Met Asp Glu Lys
 1               5                  10                  15

Gly Asn Val Cys Arg Ala Ser Leu Lys Lys Leu Ile Asp Tyr His Val
            20                  25                  30

Ala Ser Gly Thr Ser Ala Ile Val Ser Val Gly Thr Thr Gly Glu Ser
        35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240
```

```
Asn Lys Leu Phe Val Glu Pro Asn Pro Ile Pro Val Lys Trp Ala Cys
            245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
            275                 280                 285

Ala Gly Leu Leu
        290
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:5:

```
CTTCCCTTGT GCCAAGGCTG                                              20
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:6:

```
GAATTCCTTT GCGAGCAG                                                18
```

(2) INFORMATION FOR SEQ ID NO:7:

(i) SEQUENCE CHARACTERISTICS:
        (A) LENGTH: 2147 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: ESCHERICHIA COLI
        (B) STRAIN: MC1061

(ix) FEATURE:
        (A) NAME/KEY: -35_signal
        (B) LOCATION: 242..249
        (D) OTHER INFORMATION: /note= "IDENTIFICATION METHOD: S"

(ix) FEATURE:
        (A) NAME/KEY: -10_signal
        (B) LOCATION: 265..273
        (D) OTHER INFORMATION: /note= "IDENTIFICATION METHOD: S"

(ix) FEATURE:
        (A) NAME/KEY: primer_bind
        (B) LOCATION: 536..555
        (D) OTHER INFORMATION: /note= "IDENTIFICATION METHOD: E"

(ix) FEATURE:
        (A) NAME/KEY: RBS
        (B) LOCATION: 575..578
        (D) OTHER INFORMATION: /note= "IDENTIFICATION METHOD: S"

(ix) FEATURE:
            (A) NAME/KEY: CDS
            (B) LOCATION: 584..1933
            (D) OTHER INFORMATION: /note= "IDENTIFICATION METHOD: S"

(ix) FEATURE:
            (A) NAME/KEY: terminator
            (B) LOCATION: 1941..1968
            (D) OTHER INFORMATION: /note= "IDENTIFICATION METHOD: S"

(ix) FEATURE:
            (A) NAME/KEY: primer_bind
            (B) LOCATION: 2128..2147
            (D) OTHER INFORMATION: /note= "IDENTIFICATION METHOD: E"

(xi) SEQUENCE DESCRIPTION: SEQ ID NO:7:

```
TCGAAGTGTT TCTGTAGTGC CTGCCAGGCA GCGGTCTGCG TTGGATTGAT GTTTTTCATT      60

AGCAATACTC TTCTGATTTT GAGAATTGTG ACTTTGGAAG ATTGTAGCGC CAGTCACAGA     120

AAAATGTGAT GGTTTTAGTG CCGTTAGCGT AATGTTGAGT GTAAACCCTT AGCGCAGTGA     180

AGCATTTATT AGCTGAACTA CTGACCGCCA GGAGTGGATG AAAAATCCGC ATGACCCCAT     240

CGTTGACAAC CGCCCCGCTC ACCCTTTATT TATAAATGTA CTACCTGCGC TAGCGCAGGC     300

CAGAAGAGGC GCGTTGCCCA AGTAACGGTG TTGGAGGAGC CAGTCCTGTG ATAACACCTG     360

AGGGGGTGCA TCGCCGAGGT GATTGAACGG CTGGCCACGT TCATCATCGG CTAAGGGGGC     420

TGAATCCCCT GGGTTGTCAC CAGAAGCGTT CGCAGTCGGG CGTTTCGCAA GTGGTGGAGC     480

ACTTCTGGGT GAAAATAGTA GCGAAGTATC GCTCTGCGCC CACCCGTCTT CCGCTCTTCC     540

CTTGTGCCAA GGCTGAAAAT GGATCCCCTG ACACGAGGTA GTT ATG TCT GAA ATT       595
                                              Met Ser Glu Ile
                                               1

GTT GTC TCC AAA TTT GGC GGT ACC AGC GTA GCT GAT TTT GAC GCC ATG       643
Val Val Ser Lys Phe Gly Gly Thr Ser Val Ala Asp Phe Asp Ala Met
 5              10                  15                  20

AAC CGC AGC GCT GAT ATT GTG CTT TCT GAT GCC AAC GTG CGT TTA GTT       691
Asn Arg Ser Ala Asp Ile Val Leu Ser Asp Ala Asn Val Arg Leu Val
             25                  30                  35

GTC CTC TCG GCT TCT GCT GGT ATC ACT AAT CTG CTG GTC GCT TTA GCT       739
Val Leu Ser Ala Ser Ala Gly Ile Thr Asn Leu Leu Val Ala Leu Ala
         40                  45                  50

GAA GGA CTG GAA CCT GGC GAG CGA TTC GAA AAA CTC GAC GCT ATC CGC       787
Glu Gly Leu Glu Pro Gly Glu Arg Phe Glu Lys Leu Asp Ala Ile Arg
     55                  60                  65

AAC ATC CAG TTT GCC ATT CTG GAA CGT CTG CGT TAC CCG AAC GTT ATC       835
Asn Ile Gln Phe Ala Ile Leu Glu Arg Leu Arg Tyr Pro Asn Val Ile
 70                  75                  80

CGT GAA GAG ATT GAA CGT CTG CTG GAG AAC ATT ACT GTT CTG GCA GAA       883
Arg Glu Glu Ile Glu Arg Leu Leu Glu Asn Ile Thr Val Leu Ala Glu
 85              90                  95                 100

GCG GCG GCG CTG GCA ACG TCT CCG GCG CTG ACA GAT GAG CTG GTC AGC       931
Ala Ala Ala Leu Ala Thr Ser Pro Ala Leu Thr Asp Glu Leu Val Ser
            105                 110                 115

CAC GGC GAG CTG ATG TCG ACC CTG CTG TTT GTT GAG ATC CTG CGC GAA       979
His Gly Glu Leu Met Ser Thr Leu Leu Phe Val Glu Ile Leu Arg Glu
        120                 125                 130

CGC GAT GTT CAG GCA CAG TGG TTT GAT GTA CGT AAA GTG ATG CGT ACC      1027
Arg Asp Val Gln Ala Gln Trp Phe Asp Val Arg Lys Val Met Arg Thr
    135                 140                 145

AAC GAC CGA TTT GGT CGT GCA GAG CCA GAT ATA GCC GCG CTG GCG GAA      1075
Asn Asp Arg Phe Gly Arg Ala Glu Pro Asp Ile Ala Ala Leu Ala Glu
150                 155                 160
```

```
CTG GCC GCG CTG CAG CTG CTC CCA CGT CTC AAT GAA GGC TTA GTG ATC      1123
Leu Ala Ala Leu Gln Leu Leu Pro Arg Leu Asn Glu Gly Leu Val Ile
165                 170                 175                 180

ACC CAG GGA TTT ATC GGT AGC GAA AAT AAA GGT CGT ACA ACG ACG CTT      1171
Thr Gln Gly Phe Ile Gly Ser Glu Asn Lys Gly Arg Thr Thr Thr Leu
                185                 190                 195

GGC CGT GGA GGC AGC GAT TAT ACG GCA GCC TTG CTG GCG GAG GCT TTA      1219
Gly Arg Gly Gly Ser Asp Tyr Thr Ala Ala Leu Leu Ala Glu Ala Leu
                200                 205                 210

CAC GCA TCT CGT GTT GAT ATC TGG ACC GAC GTC CCG GGC ATC TAC ACC      1267
His Ala Ser Arg Val Asp Ile Trp Thr Asp Val Pro Gly Ile Tyr Thr
            215                 220                 225

ACC GAT CCA CGC GTA GTT TCC GCA GCA AAA CGC ATT GAT GAA ATC GCG      1315
Thr Asp Pro Arg Val Val Ser Ala Ala Lys Arg Ile Asp Glu Ile Ala
230                 235                 240

TTT GCC GAA GCG GCA GAG ATG GCA ACT TTT GGT GCA AAA GTA CTG CAT      1363
Phe Ala Glu Ala Ala Glu Met Ala Thr Phe Gly Ala Lys Val Leu His
245                 250                 255                 260

CCG GCA ACG TTG CTA CCC GCA GTA CGC AGC GAT ATC CCG GTC TTT GTC      1411
Pro Ala Thr Leu Leu Pro Ala Val Arg Ser Asp Ile Pro Val Phe Val
                265                 270                 275

GGC TCC AGC AAA GAC CCA CGC GCA GGT GGT ACG CTG GTG TGC AAT AAA      1459
Gly Ser Ser Lys Asp Pro Arg Ala Gly Gly Thr Leu Val Cys Asn Lys
                280                 285                 290

ACT GAA AAT CCG CCG CTG TTC CGC GCT CTG GCG CTT CGT CGC AAT CAG      1507
Thr Glu Asn Pro Pro Leu Phe Arg Ala Leu Ala Leu Arg Arg Asn Gln
            295                 300                 305

ACT CTG CTC ACT TTG CAC AGC CTG AAT ATG CTG CAT TCT CGC GGT TTC      1555
Thr Leu Leu Thr Leu His Ser Leu Asn Met Leu His Ser Arg Gly Phe
            310                 315                 320

CTC GCG GAA GTT TTC GGC ATC CTC GCG CGG CAT AAT ATT TCG GTA GAC      1603
Leu Ala Glu Val Phe Gly Ile Leu Ala Arg His Asn Ile Ser Val Asp
325                 330                 335                 340

TTA ATC ACC ACG TCA GAA GTG AGC GTG GCA TTA ACC CTT GAT ACC ACC      1651
Leu Ile Thr Thr Ser Glu Val Ser Val Ala Leu Thr Leu Asp Thr Thr
                345                 350                 355

GGT TCA ACC TCC ACT GGC GAT ACG TTG CTG ACG CAA TCT CTG CTG ATG      1699
Gly Ser Thr Ser Thr Gly Asp Thr Leu Leu Thr Gln Ser Leu Leu Met
                360                 365                 370

GAG CTT TCC GCA CTG TGT CGG GTG GAG GTG GAA GAA GGT CTG GCG CTG      1747
Glu Leu Ser Ala Leu Cys Arg Val Glu Val Glu Glu Gly Leu Ala Leu
            375                 380                 385

GTC GCG TTG ATT GGC AAT GAC CTG TCA AAA GCC TGC GGC GTT GGC AAA      1795
Val Ala Leu Ile Gly Asn Asp Leu Ser Lys Ala Cys Gly Val Gly Lys
390                 395                 400

GAG GTA TTC GGC GTA CTG GAA CCG TTC AAC ATT CGC ATG ATT TGT TAT      1843
Glu Val Phe Gly Val Leu Glu Pro Phe Asn Ile Arg Met Ile Cys Tyr
405                 410                 415                 420

GGC GCA TCC AGC CAT AAC CTG TGC TTC CTG GTG CCC GGC GAA GAT GCC      1891
Gly Ala Ser Ser His Asn Leu Cys Phe Leu Val Pro Gly Glu Asp Ala
                425                 430                 435

GAG CAG GTG GTG CAA AAA CTG CAT AGT AAT TTG TTT GAG TAA              1933
Glu Gln Val Val Gln Lys Leu His Ser Asn Leu Phe Glu  *
                440                 445                 450

ATACTGTATG GCCTGGAAGC TATATTTCGG GCCGTATTGA TTTTCTTGTC ACTATGCTCA    1993

TCAATAAACG AGCCTGTACT CTGTTAACCA GCGTCTTTAT CGGAGAATAA TTGCCTTTAA    2053

TTTTTTTATC TGCATCTCTA ATTAATTATC GAAAGAGATA AATAGTTAAG AGAAGGCAAA    2113
```

ATGAATATTA TCAGTTCTGC TCGCAAAGGA ATTC                                           2147

(2) INFORMATION FOR SEQ ID NO:8:

(i) SEQUENCE CHARACTERISTICS:
        (A) LENGTH: 449 amino acids
        (B) TYPE: amino acid
        (D) TOPOLOGY: linear (ii) MOLECULE TYPE: protein (xi) SEQUENCE DESCRIPTION: SEQ ID NO:8:

Met Ser Glu Ile Val Val Ser Lys Phe Gly Gly Thr Ser Val Ala Asp
 1               5                  10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
 65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
        290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

```
Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu
    450

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:9:

CTTTCACTGA TATCCCTCCC                                           20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:10:

AAAAAGTGGA CCAAATGGTC                                           20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:11:

CATCTAAGTA TGCATCTCGG                                           20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: other nucleic acid
             (A) DESCRIPTION: /desc = "SYNTHETIC DNA"

(xi) SEQUENCE DESCRIPTION: SEQ ID NO:12:

TGCCCCTCGA GCTAAATTAG                                                 20

(2) INFORMATION FOR SEQ ID NO:13:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:13:

TGCACGGTAG GATGTAATCG                                                 20

(2) INFORMATION FOR SEQ ID NO:14:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:14:

TTAATGAAAC AAATGCCCGG                                                 20

(2) INFORMATION FOR SEQ ID NO:15:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:15:

TTTATTCATA ATTGCCACCG                                                 20

(2) INFORMATION FOR SEQ ID NO:16:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:16:

CACGGTAATA CATATAACCG                                                 20

(2) INFORMATION FOR SEQ ID NO:17:

(i) SEQUENCE CHARACTERISTICS:
             (A) LENGTH: 20 base pairs
             (B) TYPE: nucleic acid
             (C) STRANDEDNESS: single
             (D) TOPOLOGY: linear

```
        (ii) MOLECULE TYPE: other nucleic acid
             (A) DESCRIPTION: /desc = "SYNTHETIC DNA"

(xi) SEQUENCE DESCRIPTION: SEQ ID NO:17:

CCTGCAATTG TCAAACGTCC                                                    20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:18:

GTCGACGCGC TTGAGATCTT                                                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:19:

TCATAAAGAG TCGCTAAACG                                                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:20:

CAACCGCCCG GTCATCAAGC                                                    20
```

METHOD OF PRODUCING L-LYSINE BY FERMENTATION

TECHNICAL FIELD

The present invention relates to microbial industry, and in particular relates to a method of producing L-lysine by fermentation, DNA's and microorganisms to be used for this production method.

BACKGROUND ART

In the prior art, when L-lysine is produced by a fermentative method, a microbial strain separated from the natural environment or an artificial mutant strain obtained from such a microbial strain is used in order to improve the productivity. A large number of artificial mutant strains producing L-lysine are known. Most of them are S-2-aminoethylcysteine (AEC) resistant mutant strains, and belong to the genus of Brevibacterium, Corynebacterium, Bacillus or Escherichia. Further, various techniques have been disclosed for increasing amino acid production, for example, by employing a transformant using recombinant DNA (U.S. Pat. No. 4,278,765).

With respect to those belonging to the genus Escherichia, for example, Japanese Patent Application Laid-open No. 56-18596, U.S. Pat. No. 4,346,170, and *Applied Microbiology and Biotechnoloay*, 15, 227–231 (1982) describe methods of producing L-lysine using a bacterial strain in which dihydrodipicolinate synthase (hereinafter sometimes abbreviated as "DDPS") is enhanced. However, DDPS used in these cases is a wild type, which suffers feedback inhibition by L-lysine. Thus sufficiently satisfactory L-lysine productivity has not been obtained. Incidentally, *Applied Microbiology and Biotechnology*, 15, 227–231 (1982) mentioned above is describes an L-lysine production of 3 g/l of L-lysine hydrochloride from 75 g/l of glucose, wherein a consumption coefficient (number of g of L-lysine produced from 1 g of sugar, or percentage thereof) is calculated to be 0.04, or 4%.

On the other hand, Korean Patent Publication No. 92–8382 describes a method of producing L-lysine using a bacterium belonging to Escherichia to which DDPS originating from a bacterium belonging to the genus Corynebacterium, which is known not to suffer feedback inhibition by L-lysine (consumption coefficient: 17%), is introduced. However, the upper limit temperature for growth of bacteria belonging to the genus Corynebacterium is lower than the upper limit temperature for growth of bacteria belonging to the genus Escherichia by about 10 degrees. Thus it seems that cultivation should be performed at a lowered cultivation temperature if DNA coding for DDPS originating from a bacterium belonging to the genus Corynebacterium is introduced into a bacterium belonging to the genus Escherichia in order to utilize it for L-lysine production. Therefore, it is anticipated that it is difficult to exhibit advantages possessed by the bacterium belonging to the genus Escherichia that the growth temperature is high, the growth speed is fast, and the L-lysine-producing speed is also fast. Generally, when a gene originating from a heterologous organism is expressed, there are occasionally caused decomposition of an expression product by protease and formation of an insoluble inclusion body, in which more difficulties are anticipated as compared with a case of expression of a homologous gene. Further, when DNA coding for DDPS originating from a bacterium belonging to the genus Corynebacterium is introduced into a bacterium belonging to the genus Escherichia to industrially produce L-lysine, more strict regulation is obliged as compared with a case of use of a recombinant to which a homologous gene is introduced, in accordance with the recombinant DNA guideline.

By the way, the dihydrodipicolinate synthase (DDPS) is an enzyme for dehydrating and condensing aspartosemialdehyde and pyruvic acid to synthesize dihydrodipicolinic acid. This reaction is located at an entrance into a branch to proceed to an L-lysine biosynthesis system in biosynthesis of amino acids of the aspartic acid family. This enzyme is known to be in charge of an important regulatory site as aspartokinase is in bacteria belonging to the genus Escherichia.

DDPS is encoded by a gene called dapA in *E. coli* (*Escherichia coli*). The dapA has been cloned, and its nucleotide sequence has been also determined (Richaud, F. et al., *J. Bacteriol.*, 297 (1986)).

On the other hand, aspartokinase (hereinafter sometimes abbreviated as "AK") is an enzyme for catalyzing a reaction to convert aspartic acid into β-phosphoaspartic acid, which serves as a main regulatory enzyme in a biosynthesis system of amino acids of the aspartic acid family. AK of *E. coli* has three types (AKI, AKII, AKIII), two of which are complex enzymes with homoserine dehydrogenase (hereinafter sometimes abbreviated as "HD"). One of the complex enzymes is AKI-HDI encoded by a thrA gene, and the other is AKII-HDII encoded by a metLM gene. AKI is subjected to concerted suppression by threonine and isoleucine and inhibited by threonine, while AKII is suppressed by methionine.

On the contrary, it is known that only AKIII is a simple function enzyme, which is a product of a gene designated as lysC, and is subjected to suppression and feedback inhibition by L-lysine. The ratio of their intracellular activities is AKI:AKII:AKIII=about 5:1:4.

As described above, DDPS originating from bacteria belonging to the genus Corynebacterium is not subjected to feedback inhibition by L-lysine. However, when it is introduced into a bacterium belonging to the genus Escherichia to utilize it for L-lysine production, a problem arises in the cultivation temperature. It is expected that L-lysine can be efficiently produced by fermentation by using a bacterium belonging to the genus Escherichia if a mutant enzyme of DDPS or AKIII originating from a bacterium belonging to the genus Escherichia, which is not subjected to feedback inhibition by L-lysine, can be obtained. However, there is no preceding literature which describes such a mutant enzyme of DDPS, and although there is one report on a mutant enzyme of AKIII (Boy, E., et al., J. Bacteriol., 112, 84 (1972)) no example has been known which suggests that such a mutant enzyme may improve productivity of L-lysine.

DISCLOSURE OF THE INVENTION

The present invention has been made taking the aforementioned viewpoints into consideration, an object of which is to obtain DDPS and AKIII originating from bacteria belonging to the genus Escherichia with sufficiently desensitized feedback inhibition by L-lysine, and provide a method of producing L-lysine by fermentation which is more improved than those in the prior art.

As a result of diligent and repeated investigation in order to achieve the object described above, the present inventors have succeeded in obtaining DNA coding for DDPS originating from a bacterium belonging to the genus Escherichia in which feedback inhibition by L-lysine is sufficiently desensitized. The DNA coding for DDPS originating from E. coli in which feedback inhibition by L-lysine is sufficiently desensitized is sometimes referred to herein as mutant dapA or dapA*.

The inventors have further created a bacterium belonging to the genus Escherichia harboring mutant dapA and aspartokinase which is desensitized feedback inhibition by L-lysine. The DNA coding for aspartokinase originating from E. coli in which feedback inhibition by L-lysine is sufficiently desensitized is sometimes referred to herein as mutant lysC or lysC*.

The inventors have further created a bacterium belonging to the genus Escherichia harboring mutant dapA and mutant lysC. And it has been found that a considerable amount of L-lysine can be produced and accumulated in a culture by cultivating the aforementioned bacterium belonging to the genus Escherichia in a preferred medium.

The inventors have still further found that the productivity of L-lysine can be further improved by enhancing other genes in the L-lysine biosynthesis system of a bacterium belonging to the genus Escherichia harboring the mutant dapA and the mutant lysC.

Namely, the present invention lies in a DNA coding for a dihydrodipicolinate synthase originating from a bacterium belonging to the genus Escherichia having mutation to desensitize feedback inhibition by L-lysine. The mutation to desensitize feedback inhibition by L-lysine is exemplified by mutation selected from the group consisting of mutation to replace a 81st alanine residue with a valine residue, mutation to replace a 118th histidine residue with a tyrosine residue, and mutation to replace the 81st alanine residue with the valine residue and replace the 118th histidine residue with the tyrosine residue, as counted from the N-terminal in an amino acid sequence of dihydrodipicolinate synthase defined in SEQ ID NO:4 in Sequence Listing.

The present invention further lies in a bacterium belonging to the genus Escherichia transformed by introducing, into its cells, a DNA coding for a dihydrodipicolinate synthase originating from a bacterium belonging to the genus Escherichia having mutation to desensitize feedback inhibition by L-lysine. The mutation to desensitize feedback inhibition by L-lysine is exemplified by mutation to replace a 81st alanine residue with a valine residue, mutation to replace a 118th histidine residue with a tyrosine residue, and mutation to replace the 81st alanine residue with the valine residue and replace the 118th histidine residue with the tyrosine residue, as counted from the N-terminal in an amino acid sequence of dihydrodipicolinate synthase defined in SEQ ID NO:4 in Sequence Listing.

The present invention further lies in the aforementioned bacterium belonging to the genus Escherichia harboring an aspartokinase which is also desensitized feedback inhibition by L-lysine. A method to allow the bacterium belonging to the genus Escherichia to harbor the aspartokinase which is desensitized feedback inhibition by L-lysine is exemplified by a method for introducing, into its cells, a DNA coding for an aspartokinase III originating from a bacterium belonging to the genus Escherichia having mutation to desensitize feedback inhibition by L-lysine.

The mutation of the aspartokinase III to desensitize feedback inhibition by L-lysine is exemplified by mutation to replace a 323rd glycine residue with an aspartic acid residue, mutation to replace the 323rd glycine residue with the aspartic acid residue and replace a 408th glycine residue with an aspartic acid residue, mutation to replace a 34th arginine residue with a cysteine residue and replace the 323rd glycine residue with the aspartic acid residue, mutation to replace a 325th leucine residue with a phenylalanine residue, mutation to replace a 318th methionine residue with an isoleucine residue, mutation to replace the 318th methionine residue with the isoleucine residue and replace a 349th valine residue with a methionine residue, mutation to replace a 345th serine residue with a leucine residue, mutation to replace a 347th valine residue with a methionine residue, mutation to replace a 352nd threonine residue with an isoleucine residue, mutation to replace the 352nd threonine residue with the isoleucine residue and replace a 369th serine residue with a phenylalanine residue, mutation to replace a 164th glutamic acid residue with a lysine residue, and mutation to replace a 417th methionine residue with an isoleucine residue and replace a 419th cysteine residue with a tyrosine residue, as counted from the N-terminal in an amino acid sequence of aspartokinase III defined in SEQ ID NO:8 in Sequence Listing.

The DNA coding for a dihydrodipicolinate synthase originating from a bacterium belonging to the genus Escherichia having mutation to desensitize feedback inhibition by L-lysine, and the DNA coding for an aspartokinase III having mutation to desensitize feedback inhibition by L-lysine may be harbored on a chromosome of a bacterium belonging to the genus Escherichia respectively, or may be harbored in cells on an identical plasmid or separate plasmids. Further, it is also acceptable that one of the respective DNA's is harbored on a chromosome, and the other DNA is harbored on a plasmid.

The present invention still further lies in the aforementioned bacterium belonging to the genus Escherichia wherein a dihydrodipicolinate reductase gene is enhanced. The enhancement of the dihydrodipicolinate reductase gene can be achieved by transformation with a recombinant DNA constructed by ligating the dihydrodipicolinate reductase gene with a vector autonomously replicable in cells of bacteria belonging to the genus Escherichia.

The present invention further lies in the aforementioned bacterium belonging to the genus Escherichia wherein an enhanced diaminopimelate dehydrogenase gene originating from coryneform bacteria such as Brevibacterium lactofermentum is introduced. The introduction of the enhanced diaminopimelate dehydrogenase gene originating from coryneform bacteria can be achieved by transformation with a recombinant DNA constructed by ligating the gene with a vector autonomously replicable in cells of bacteria belonging to the genus Escherichia. As coryneform bacteria, there may be exemplified wild type strains producing glutamic acid, and mutant strains thereof producing other amino acids, which belong to the genus Corynebacterium or the genus Brevibacterium. More concretely, Brevibacterium flavum, Brevibacterium divaricatum, Corynebacterium glutamicum and Corynebacterium lilium as well as Brevibacterium lactofermentum are exemplified as coryneform bacteria used for the present invention.

The present invention further lies in the bacterium belonging to the genus Escherichia wherein a tetrahydrodipicotinate succinylase gene and a succinyldiaminopmelate deacylase gene are enhanced instead of the aforementioned diaminodipimelate dehydrogenase gene. The enhancement of these genes can be achieved by transformation with a single recombinant DNA or two recombinant DNA's constructed by ligating these genes with an identical vector or different vectors autonomously replicable in cells of bacteria belonging to the genus Escherichia.

The present invention further provides a method of producing L-lysine comprising the steps of cultivating any of the bacteria belonging to the genus Escherichia described above in an appropriate medium, producing and accumulating L-lysine in a culture thereof, and collecting L-lysine from the culture.

In this specification, DNA coding for DDPS or AKIII, or DNA containing a promoter in addition thereto is sometimes referred to as "DDPS gene" or "AKIII gene". Further, the mutant enzyme which is desensitized feedback inhibition by L-lysine, and DNA coding for it or DNA containing a promoter in addition to it are sometimes simply refereed to as "mutant enzyme" and "mutant gene", respectively. Further, the phrase "feedback inhibition by L-lysine is desensitized" means that substantial desensitization of inhibition is sufficient, and complete desensitization is not necessary.

The present invention will be explained in detail below.

<1> DNA Coding for Mutant Dihydrodipicolinate Synthase (DDPS) of the Present Invention The DNA coding for the mutant DDPS of the present invention has mutation to desensitize feedback inhibition by L-lysine of DDPS encoded in DNA coding for the wild type DDPS. DDPS is exemplified by those originating from bacteria belonging to the genus Escherichia, especially DDPS originating from *E. coli* The mutation of DDPS to desensitize feedback inhibition by L-lysine is exemplified by:

(1) mutation to replace a 81st alanine residue with a valine residue;

(2) mutation to replace a 118th histidine residue with a tyrosine residue; and (3) mutation to replace the 81st alanine residue with the valine residue and replace the 118th histidine residue with the tyrosine residue; as counted from the N-terminal of DDPS in an amino acid sequence of DDPS defined in SEQ ID NO:4 in Sequence Listing.

The DNA coding for the wild type DDPS is not especially limited provided that it codes for DDPS originating from a bacterium belonging to the genus Escherichia, which is concretely exemplified by DNA coding for an amino acid sequence defined in SEQ ID NO:4, and is further concretely exemplified by a sequence represented by base numbers 272–1147 in a base sequence defined in SEQ ID NO:3. In these sequences, those having the mutation in nucleotide sequence to cause the replacement of amino acid residues described above are the DNA coding for the mutant DDPS of the present invention. Any codon corresponding to the replaced amino acid residue is available especially irrelevantly to its kind, provided that it codes for the identical amino acid residue. Further, it is postulated that possessed DDPS is slightly different in sequence depending on difference in bacterial species and bacterial strain, however, those having replacement, deletion or insertion of amino acid residue(s) at position(s) irrelevant to enzyme activity are also included in the mutant DDPS gene of the present invention.

A method for obtaining such a mutant gene is as follows. At first, a DNA containing a wild type DDPS gene or DDPS gene having another mutation is subjected to an in vitro mutation treatment, and a DNA after the mutation treatment is ligated with a vector DNA adapted to a host to obtain a recombinant DNA. The recombinant DNA is introduced into a host microorganism to obtain transformants. When one which expresses a mutant DDPS is selected among the aforementioned transformants, such a transformant harbors a mutant gene. Alternatively, a DNA containing a wild type DDPS gene or DDPS gene having another mutation may be ligated with a vector DNA adapted to a host to obtain a recombinant DNA. The recombinant DNA is thereafter subjected to an in vitro mutation treatment, and a recombinant DNA after the mutation treatment is introduced into a host microorganism to obtain transformants. When one which expresses a mutant DDPS is selected among the aforementioned transformants, such a transformant also harbors a mutant gene.

It is also acceptable that a microorganism which, produces a wild type enzyme is subjected to a mutation treatment to create a mutant strain which produces a mutant enzyme, and then a mutant gene is obtained from the mutant strain. Alternatively, a transformant to which a recombinant DNA ligated with a wild type gene is introduced may be subjected to a mutation treatment to create a mutant strain which produces a mutant enzyme. When a recombinant DNA is thereafter recovered from the mutant strain, a mutant gene is created on the aforementioned DNA.

The agent for performing the in vitro mutation treatment of DNA is exemplified by hydroxylamine and the like. Hydroxylamine is a chemical mutation treatment agent which causes mutation from cytosine to thymine by changing cytosine to $N^4$-hydroxycytosine. Alternatively, when a microorganism itself is subjected to a mutation treatment, the treatment is performed by using ultraviolet light irradiation, or a mutating agent usually used for artificial mutation such as N-methyl-N'-nitro-N-nitrosoguanidine (NTG) or nitrous acid.

No problem occurs when any one is used as a donor microorganism for DNA containing the wild type DDPS gene or DDPS gene having another mutation described above, provided that it is a microorganism belonging to the genus Escherichia. Concretely, it is possible to utilize those described in a book written by Neidhardt et al. (Neidhardt, F. C. et al., *Escherichia coli* and *Salmonella Typhimurium*, American Society for Microbiology, Washington D. C., 1208, table 1). For example, an *E. coli* JM109 strain and an MC1061 strain are exemplified. When a wild strain is used as a donor microorganism for DNA containing a DDPS gene, a DNA containing a wild type DDPS gene can be obtained.

(1) Preparation of Wild Type DDPS Gene

An example of preparation of DNA containing a DDPS gene will be described below. At first, *E. coli* having wild type dapA, for example, MC1061 strain, is cultivated to obtain a culture. When the microorganism described above is cultivated, cultivation may be performed in accordance with an ordinary solid culture method, however, cultivation is preferably performed by adopting a liquid culture method considering efficiency during collection of the bacterium. A medium may be used in which one or more nitrogen sources such as yeast extract, peptone, meat extract, corn steep liquor and exudate of soybean or wheat are added with one or more inorganic salts such as potassium dihydrogenphosphate, dipotassium hydrogenphosphate, magnesium sulfate, sodium chloride, magnesium chloride, ferric chloride, ferric sulfate or manganese sulfate, and further optionally and adequately added with sugar materials, vitamins and the like. It is appropriate that the initial pH of the medium is adjusted to 6–8. The cultivation is performed for 4–24 hours at 30–42° C., preferably at about 37° C. by means of deep culture with aeration and agitation, shaking culture or stationary culture or the like.

The culture thus obtained is centrifuged, for example, at 3,000 r.p.m. for 5 minutes to obtain a cell pellet of *E. coli* MC1061 strain. Chromosomal DNA can be obtained from the cell pellet by means of, for example, a method of Saito and Miura (*Biochem. Biophys. Acta.*, 72, 619 (1963)), or a method of K. S. Kirby (*Biochem. J.*, 64, 405 (1956)).

In order to isolate the DDPS gene from the chromosomal DNA thus obtained, a chromosomal DNA library is prepared. At first, the chromosomal DNA is partially digested with a suitable restriction enzyme to obtain a mixture of various fragments. A wide variety of restriction enzymes can be used if the degree of cutting is controlled by the cutting reaction time and the like. For example, Sau3AI is allowed to react on the chromosomal DNA at a temperature not less than 30° C., preferably at 37° C. at an enzyme concentration of 1–10 units/ml for various periods of time (1 minute to 2 hours) to digest it.

Next, obtained DNA fragments are ligated with a vector DNA autonomously replicable in cells of bacteria belonging to the genus Escherichia to prepare recombinant DNA. Concretely, a restriction enzyme, which generates the terminal nucleotide sequence complement to that generated by the restriction enzyme Sau3AI used to cut the chromosomal DNA, for example, BmHI, is allowed to act on the vector DNA under a condition of a temperature not less than 30° C. and an enzyme concentration of 1–100 units/ml for not less than 1 hour, preferably for 1–3 hours to completely digest it, and cut and cleave it. Next, the chromosomal DNA fragment mixture obtained as described above is mixed with the cleaved and cut vector DNA, on which DNA ligase, preferably T4 DNA ligase is allowed to act under a condition of a temperature of 4–16° C. at an enzyme concentration of 1–100 units/ml for not less than 1 hour, preferably for 6–24 hours to obtain recombinant DNA.

The obtained recombinant DNA is used to transform a microorganism belonging to the genus Escherichia, for example, a DDPS deficient mutant strain such as an *Escherichia coli* K-12 strain, preferably a JE7627 strain (ponB704, dacB12, pfv$^+$, tonA2, dapA, lysA, str, malA38, metB1, ilvH611, leuA371, proA3, lac-3, tsx-76) to prepare a chromosomal DNA library. The transformation can be performed, for example, by a method of D. M. Morrison (*Methods in Enzymology* 68, 326 (1979)) or a method in which recipient bacterial cells are treated with calcium chloride to increase permeability of DNA (Mandel, M. and Higa, A., *J. Mol. Biol.*, 53, 159 (1970)). The JE7627 strain is available from National Institute of Genetics (Mishimashi, Shizuoka-ken, Japan).

A bacterial strain having recombinant DNA of the DDPS gene is obtained from strains having increased DDPS activity or strains in which auxotrophy resulting from deficiency in DDPS gene is complemented, among the obtained chromosomal DNA library. For example, a DDPS deficient mutant strain requires diaminopimelic acid. Thus when the DDPS deficient mutant strain is used as a host, a DNA fragment containing the DDPS gene can be obtained by isolating a bacterial strain which becomes capable of growing on a medium containing no diaminopimelic acid, and recovering recombinant DNA from the bacterial strain.

Confirmation of the fact whether or not a candidate strain having recombinant DNA containing a DDPS gene actually harbors recombinant DNA in which the DDPS gene is cloned can be achieved by preparing a cellular extract from the candidate strain, and preparing a crude enzyme solution therefrom to confirm whether or not the DDPS activity has been increased. A procedure to measure the enzyme activity of DDPS can be performed by a method of Yugari et al. (Yugari, Y. and Gilvarg, C., *J. Biol. Chem.*, 240, 4710 (1962)).

Recombinant DNA in which DNA containing the DDPS gene is inserted into the vector DNA can be isolated from the bacterial strain described above by means of, for example, a method of P. Guerry et al. (*J. Bacteriol.*, 116, 1064 (1973)) or a method of D. B. Clewell (*J. Bacteriol.*, 110, 667 (1972)).

Preparation of the wild type DDPS gene can be also performed by preparing chromosomal DNA from a strain having a DDPS gene on chromosome by means of a method of Saito and Miura or the like, and amplifying the DDPS gene by means of a polymerase chain reaction (PCR) method (see White, T. J. et al.; *Trends Genet.*, 5, 185 (1989)). DNA primers to be used for the amplification reaction are those complemental to both 3'-terminals of a double stranded DNA containing an entire region or a partial region of the DDPS gene. When only a partial region of the DDPS gene is amplified, it is necessary to use such DNA fragments as primers to perform screening of a DNA fragment containing the entire region from a chromosomal DNA library. When the entire region of the DDPS gene is amplified, a PCR reaction solution including DNA fragments containing the amplified DDPS gene is subjected to agarose gel electrophoresis, and then an aimed DNA fragment is extracted. Thus a DNA fragment containing the DDPS gene can be recovered.

The DNA primers may be adequately prepared on the basis of, for example, a sequence known in *E. coli* (Richaud, F. et al., *J. Bacteriol.*, 297 (1986)). Concretely, primers which can amplify a region comprising 1150 bases coding for the DDPS gene are preferable, and two species of primers defined in SEQ ID NO:1 and NO:2 are suitable. Synthesis of the primers can be performed by an ordinary method such as a phosphoamidite method (see *Tetrahedron Letters*, 22, 1859 (1981)) by using a commercially available DNA synthesizer (for example, DNA Synthesizer Model 380B produced by Applied Biosystems Inc.). Further, the PCR can be performed by using a commercially available PCR apparatus (for example, DNA Thermal Cycler Model PJ2000 produced by Takara Shuzo Co., Ltd.), using Tag DNA polymerase (supplied by Takara Shuzo Co., Ltd.) in accordance with a method designated by the supplier.

With respect to the DDPS gene amplified by the PCR method, operations such as introduction of mutation into the DDPS gene become easy, when it is ligated with a vector DNA autonomously replicable in cells of bacteria belonging to the genus Escherichia, and introduced into cells of bacteria belonging to the genus Escherichia. The vector DNA to be used, the transformation method, and the confirmation method for the presence of the DDPS gene are the same as those in the aforementioned procedure.

(2) Introduction of Mutation Into DDPS Gene

The method for carrying out mutation such as replacement, insertion and deletion of amino acid residues is exemplified by a recombinant PCR method (Higuchi, R., 61, in *PCR Technology* (Erlich, H. A. Eds., Stockton press (1989))), and a site specific mutagenesis method (Kramer, W. and Frits, H. J., *Meth. in Enzymol.*, 154, 350 (1987); Kunkel T. A. et al., *Meth. in Enzymol.*, 154, 367 (1987)). Aimed mutation can be caused at an aimed site by using these methods.

Further, according to chemical synthesis of an aimed gene, it is possible to introduce mutation or random mutation into an aimed site.

Further, a method is available in which the DDPS gene on chromosome or plasmid is directly treated with hydroxylamine (Hashimoto, T. and Sekiguchi, M. *J. Bacteriol.*, 159, 1039 (1984)). Alternatively, it is acceptable to use a method in which a bacterium belonging to the genus Escherichia having the DDPS gene is irradiated by ultraviolet light, or a method based on a treatment with a chemical agent such as N-methyl-N'-nitrosoguanidine or nitrous acid. According to these methods, mutation can be introduced randomly.

With respect to a selection method for the mutant gene, recombinant DNA comprising a DNA fragment containing the DDPS gene and vector DNA is at first directly subjected to a mutation treatment with hydroxylamine or the like, which is used to transform, for example, an *E. coli* W3110 strain. Next, transformed strains are cultivated on a minimal medium such as M9 containing S-2-aminoethylcysteine (AEC) as an analog of L-lysine. Strains harboring recombinant DNA containing the wild type DDPS gene cannot synthesize L-lysine and diaminopimelic acid (DAP) and are suppressed in growth because DDPS expressed from the recombinant DNA is inhibited by AEC. On the contrary, a strain harboring recombinant DNA containing the DDPS gene in which inhibition by L-lysine is desensitized has a mutant enzyme encoded by the DDPS gene in the aforementioned recombinant DNA which is not inhibited by AEC. Thus it should be capable of growth on the minimal medium in which AEC is added. This phenomenon can be utilized to select a strain which is resistant in growth to AEC as an analog of L-lysine, that is a strain harboring recombinant DNA containing a mutant DDPS gene in which inhibition is desensitized.

The mutant gene thus obtained may be introduced as a recombinant DNA into a suitable host microorganism, and expressed. Thus a microorganism can be obtained which harbors DDPS being desensitized feedback inhibition. The host is preferably a microorganism belonging to the genus Escherichia, for which *E. coli* is exemplified.

Alternatively, a mutant DDPS gene fragment may be taken out from the recombinant DNA, and inserted into another vector to make use. The vector DNA which can be used in the present invention is preferably plasmid vector DNA, for which there are exemplified pUC19, pUC18, pBR322, pHSG299, pHSG298, pHSG399, pHSG398, RSF1010, pMW119, pMW118, pMW219 and pMW218. Besides, vectors of phage DNA can be also utilized.

Further, in order to express the mutant DDPS gene efficiently, another promoter which works in microorganisms such as lac, trp and PL may be ligated upstream from a DNA sequence coding for the mutant DDPS, or a promoter contained in the DDPS gene may be used as it is, or after amplifying the promoter.

In addition, as described above, the mutant gene may be inserted into an autonomously replicable vector DNA, which is inserted into a host, and allowed to be harbored by the host as extrachromosomal DNA such as a plasmid. Alternatively, the mutant gene may be integrated into chromosome of a host microorganism by a method using transduction, transposon (Berg, D. E. and Berg, C. M., *Bio/Technol.*, 1, 417 (1983)), Mu phage (Japanese Patent Application Laid-open No. 2-109985) or homologous recombination (*Experiments in Molecular Genetics*, Cold Spring Harbor Lab. (1972)).

<2> DNA Coding for Mutant Aspartokinase III (AKIII) Used for the Present Invention The DNA coding for mutant AKIII used for the present invention has mutation to desensitize feedback inhibition of encoded AKIII by L-lysine in DNA coding for wild type AKIII. The mutation to desensitize feedback inhibition of AKIII by L-lysine is exemplified by:

(a) mutation to replace a 323rd glycine residue with an aspartic acid residue;

(b) mutation to replace the 323rd glycine residue with the aspartic acid residue and replace a 408th glycine residue with an aspartic acid residue;

(c) mutation to replace a 34th arginine residue with a cysteine residue and replace the 323rd glycine residue with the aspartic acid residue;

(d) mutation to replace a 325th leucine residue with a phenylalanine residue;

(e) mutation to replace a 318th methionine residue with an isoleucine residue;

(f) mutation to replace the 318th methionine residue with the isoleucine residue and replace a 349th valine residue with a methionine residue;

(g) mutation to replace a 345th serine residue with a leucine residue;

(h) mutation to replace a 347th valine residue with a methionine residue;

(i) mutation to replace a 352nd threonine residue with an isoleucine residue;

(j) mutation to replace the 352nd threonine residue with the isoleucine residue and replace a 369th serine residue with a phenylalanine residue;

(k) mutation to replace a 164th glutamic acid residue with a lysine residue; and (l) mutation to replace a 417th methionine residue with an isoleucine residue and replace a 419th cysteine residue with a tyrosine residue;

as counted from the N-terminal of AKIII in an amino acid sequence of AKIII defined in SEQ ID NO:8 in Sequence Listing.

The DNA coding for the wild type AKIII is not especially limited, for which DNA coding for AKIII originating from a bacterium belonging to the genus Escherichia such as *E. coli* is exemplified. Concretely, there are exemplified DNA coding for an amino acid sequence defined in SEQ ID NO:8, and a sequence represented by base numbers 584–1930 in a base sequence defined in SEQ ID NO:7. Incidentally, AKIII of *E. coli* is encoded by a lysC gene.

In these sequences, those which have mutation in base sequence to cause replacement of amino acid residues described above are DNA coding for the mutant AKIII of the present invention. Any codon corresponding to the replaced amino acid residue is available especially regardless of its kind, provided that it codes for the identical amino acid residue. Further, there are those in which amino acid sequences of possessed wild type AKIII are slightly different depending on difference in bacterial species and bacterial strains. Those having replacement, deletion or insertion of amino acid residue(s) at position(s) irrelevant to enzyme activity in such a manner are also included in the mutant AKIII gene of the present invention. For example, a base sequence of a wild type lysC gene obtained in Example 2 described below (SEQ ID NO:7) is different from an already published sequence of lysC of an *E. coli* K-12 JC411 strain at 6 sites (Cassan, M., Parsot, C., Cohen, G. N., and Patte, J. C., *J. Biol. Chem.*, 261 1052 (1986)). Encoded amino acid residues are different at 2 sites of them (in lysC of the JC411 strain, a 58th glycine residue is replaced with a cysteine residue, and a 401st glycine residue is replaced with an alanine residue, as counted from the N-terminal in an amino acid sequence of lysC defined in SEQ ID NO:8). It is expected even for lysC having the same sequence as that of lysC of the *E. coli* K-12 JC411 strain that lysC having mutation in which feedback inhibition by L-lysine is desensitized is obtained if any of the aforementioned mutation of (a) to (l) is introduced.

A method for obtaining DNA coding for the mutant AKIII in which feedback inhibition by L-lysine is desensitized is as follows. At first, a DNA containing a wild type AKIII gene or AKIII gene having another mutation is subjected to an in vitro mutation treatment, and a DNA after the mutation treatment is ligated with a vector DNA adapted to a host to obtain a recombinant DNA. The recombinant DNA is introduced into a host microorganism to obtain transformants. When one which expresses a mutant AKIII is selected among the aforementioned transformants, such a transformant harbors a mutant gene. Alternatively, a DNA containing a wild type AKIII gene or AKIII gene having another mutation may be ligated with a vector DNA adapted to a host to obtain a recombinant DNA. The recombinant DNA is thereafter subjected to an in vitro mutation treatment, and a recombinant DNA after the mutation treatment is introduced into a host microorganism to obtain transformants. When one which expresses a mutant AKIII is selected among the aforementioned transformants, such a transformant also harbors a mutant gene.

Alternatively, it is also acceptable that a microorganism which produces a wild type enzyme is subjected to a mutation treatment to create a mutant strain which produces a mutant enzyme, and then a mutant gene is obtained from the mutant strain. The agent for performing a direct mutation treatment of DNA is exemplified by hydroxylamine and the like. Hydroxylamine is a chemical mutation treatment agent which causes mutation from cytosine to thymine by changing cytosine to $N^4$-hydroxycytosine. Alternatively, when a microorganisms itself is subjected to a mutation treatment, the treatment is performed by ultraviolet light irradiation, or using a mutating agent usually used for artificial mutation such as N-methyl-N'-nitro-N-nitrosoguanidine (NTG).

Any one is used as a donor microorganism for DNA containing the wild type AKIII gene or AKIII gene having another mutation described above, provided that it is a microorganism belonging to the genus Escherichia. Concretely, it is possible to utilize those described in a book written by Neidhardt et al. (Neidhardt, F. C. et al., *Escherichia coli* and *Salmonella Typhimurium,* American Society for Microbiology, Washington D. C., 1208, table 1). For example, an *E. coli* JM109 strain and an MC1061 strain are exemplified. When the AKIII gene is obtained from these strains, preparation of chromosomal DNA, preparation of a chromosomal DNA library and the like may be performed in the same manner as the preparation of the DDPS gene described above. As the host to be used for preparation of the library, it is preferable to use a strain entirely deficient in AKI, II and III such as an *E. coli* GT3 strain (available from *E. coli* Genetic Stock Center (Connecticut, United States)).

From the obtained chromosomal DNA library, a bacterial strain having a recombinant DNA of the AKIII gene is obtained as a strain in which the AKIII activity is increased, or a strain in which auxotrophy is complemented. Cellular extracts are prepared from candidate strains, and crude enzyme solutions are prepared therefrom to confirm the AKIII activity. The measurement procedure for the AKIII enzyme activity may be performed in accordance with a method of Stadtman et al. (Stadtman, E. R., Cohen, G. N., LeBras, G., and Robichon-Szulmajster, H., *J. Biol. Chem.,* 236, 2033 (1961)).

For example, when a mutant strain completely deficient in AK is used as a host, a DNA fragment containing an AKIII gene can be obtained by isolating a transformed strain which becomes capable of growing on a medium not containing L-lysine, L-threonine, L-methionine and diaminopimelic acid, or on a medium not containing homoserine and diaminopimelic acid, and recovering recombinant DNA from the bacterial strain.

When the AKIII gene is amplified from chromosomal DNA by means of the PCR method, DNA primers to be used for the PCR reaction can be properly prepared on the basis of, for example, a sequence known in *E. coli* (Cassan, M., Parsot, C., Cohen, G. N., and Patte, J. C., *J. Biol. Chem.,* 261, 1052 (1986)). However, primers which can amplify a region comprising 1347 bases coding for lysC gene is suitable, and for example, two primers having sequences defined in SEQ ID NO:5 and NO:6 are suitable.

The method for carrying out mutation such as replacement, insertion and deletion of amino acid residue(s) on the AKIII gene obtained as described above is exemplified by the recombinant PCR method, the site specific mutagenesis method and the like, in the same manner as the mutation treatment of the DDPS gene described above.

Further, according to chemical synthesis of an aimed gene, it is possible to introduce mutation or random mutation into an aimed site.

Further, a method is available in which DNA of the AKIII gene on chromosome or extrachromosomal recombinant DNA is directly treated with hydroxylamine (Hashimoto, T. and Sekiguchi, M. *J. Bacteriol.,* 159, 1039 (1984)). Alternatively, it is acceptable to use a method in which a bacterium belonging to the genus Escherichia having an AKIII gene on chromosome or extrachromosomal recombinant DNA is irradiated by ultraviolet light, or a method to perform a treatment with a chemical agent such as N-methyl-N'-nitrosoguanidine or nitrous acid.

With respect to a selection method for the mutant AKIII gene, a strain completely deficient in AK, for example, an *E. coli* GT3 strain is at first transformed with a recombinant DNA containing an AKIII gene having been subjected to the mutation treatment. Next, transformed strains are cultivated on a minimal medium such as M9 containing a considerable amount of L-lysine. Strains harboring recombinant DNA containing a wild type AKIII gene cannot synthesize L-threonine, L-isoleucine, L-methionine and diaminopimelic acid (DAP) and are suppressed in growth because only one AK is inhibited by L-lysine. On the contrary, the strain harboring recombinant DNA containing the mutant AKIII gene in which inhibition by L-lysine is desensitized should be capable of growth on the minimal medium added with the considerable amount of L-lysine. This phenomenon can be utilized to select a strain which is resistant in growth to L-lysine or AEC as an analog of L-lysine, that is a strain harboring recombinant DNA containing a mutant AKIII gene in which inhibition is desensitized.

The mutant gene thus obtained may be introduced as a recombinant DNA into a suitable microorganism (host), and expressed. Thus a microorganism can be obtained which harbors AKIII being desensitized feedback inhibition.

The host is preferably a microorganism belonging to the genus Escherichia, for which *E. coli* is exemplified.

Alternatively, a mutant AKIII gene fragment may be taken out from the recombinant DNA, and inserted into another vector to make use. The vector DNA which can be used in the present invention is preferably plasmid vector DNA, for which there are exemplified pUC19, pUC18, pBR322, pHSG299, pHSG298, pHSG399, pHSG398, RSF1010, pMW119, pMW118, pMW219 and pMW218. Besides, vectors of phage DNA can be also utilized.

Further, in order to express the mutant AKIII gene efficiently, another promoter which works in microorganisms such as lac, trp and PL may be ligated upstream from a DNA sequence coding for the mutant AKIII, or a promoter contained in the AKIII gene may be used as it is, or after amplifying it.

In addition, as described above, the mutant gene may be inserted into an autonomously replicable vector DNA, inserted into a host, and allowed to be harbored by the host as extrachromosomal DNA such as plasmid. Alternatively, the mutant gene may be integrated into chromosome of a host microorganism by a method using transduction, transposon (Berg, D. E. and Berg, C. M., Bio/Technol., 1, 417 (1983)), Mu phage (Japanese Patent Application Laid-open No. 2-109985) or homologous recombination (*Experiments in Molecular Genetics,* Cold Spring Harbor Lab. (1972)).

<3> Production of L-lysine According to the Present Invention

L-lysine can be efficiently produced by cultivating, in a preferred medium, the bacterium transformed by introducing the mutant DDPS gene obtained as described above and allowed to harbor AK which is desensitized feedback inhibition by L-lysine, producing and accumulating L-lysine in a culture thereof, and collecting L-lysine from the culture. Namely, L-lysine can be efficiently produced by allowing the bacterium belonging to the genus Escherichia to harbor both of the mutant DDPS and the mutant AKIII.

The bacterium belonging to the genus Escherichia harboring AK which is desensitized feedback inhibition by L-lysine is exemplified by bacteria belonging to the genus Escherichia transformed by integrating, into chromosomal DNA, a DNA coding for AKIII having mutation to desensitize feedback inhibition by L-lysine, or bacteria belonging to the genus Escherichia transformed by introducing, into cells, a recombinant DNA constructed by ligating the DNA with a vector DNA autonomously replicable in cells of bacteria belonging to the genus Escherichia. Further, AK in which feedback inhibition by L-lysine is desensitized may be a wild type AK which does not suffer feedback inhibition by L-lysine, or one to which such a wild type AK gene is introduced into a bacterium belonging to the genus Escherichia in the same manner. Further, a mutant strain of a bacterium belonging to the genus Escherichia, which has become to produce a mutant AKIII by means of a mutation treatment of cells of a bacterium belonging to the genus Escherichia, is also acceptable.

On the other hand, in order to achieve transformation by introducing the mutant DDPS gene into a bacterium belonging to the genus Escherichia, the mutant DDPS gene may be integrated into chromosomal DNA to achieve transformation, or transformation may be achieved by introducing, into cells, a recombinant DNA constructed by ligating the mutant DDPS gene with a vector DNA autonomously replicable in cells of bacteria belonging to the genus Escherichia.

When the both of the mutant DDPS gene and the mutant AKIII gene are introduced into a bacterium belonging to the genus Escherichia, the both mutant genes may be integrated into and harbored on chromosomal DNA of the bacterium belonging to the genus Escherichia, or they may be harbored on an identical plasmid or separated plasmids in cells as extrachromosomal DNA. When separated plasmids are used, it is preferable to use plasmids having a stable distribution mechanism to allow each of them to be compatibly harbored in the cell. Further, one of the mutant genes may be integrated into and harbored on chromosomal DNA, and the other mutant gene may be harbored on a plasmid in cells as extrachromosomal DNA, respectively. When the mutant DDPS gene and the mutant AKIII gene are introduced into a bacterium belonging to the genus Escherichia, any order of introduction of the both genes is acceptable.

The productivity of L-lysine can be further improved by enhancing a dihydrodipicolinate reductase gene of the bacterium belonging to the genus Escherichia in which the mutant DDPS gene and the mutant AKIII gene have been introduced. The productivity of L-lysine can be still further improved by introducing a diaminopimelate dehydrogenase gene originating from a coryneform bacterium into the bacterium belonging to the genus Escherichia in which the dihydrodipicolinate reductase gene has been enhanced. This diaminopimelate dehydrogenase gene should be enhanced. Alternatively, the productivity of L-lysine can be also improved in a similar degree by enhancing tetrahydrodipicolinate succinylase gene and a succinyldiaminopimelate deacylase gene instead of the introduction of the diaminopimelate dehydrogenase.

The enhancement of gene herein refers to enhancement in activity of an enzyme as an expression product of the gene per a cell. Concretely, there may be exemplified enhancement in copy number of the gene in a cell, enhancement in expression amount per the gene by using a promoter having a high expression efficiency, and introduction of mutation to enhance enzyme activity into the gene. In order to enhance the copy number of a gene in a cell, the gene is inserted into a vector autonomously replicable in bacteria belonging to the genus Escherichia, and a bacterium belonging to the genus Escherichia may be transformed with this vector. This vector is preferably a multi-copy type plasmid. Alternatively, the copy number may be increased by amplifying DNA integrated into chromosomal DNA by using Mu phage or the like. With respect to the use of the plasmid, when plasmids are used for introduction of the mutant DDPS gene and the mutant AKIII gene, such plasmids having a stable distribution mechanism are preferably used in which these plasmids are stably harbored in a cell together. Any order of introduction of the genes is acceptable.

A mechanism will be explained below in which the productivity of L-lysine can be improved in a stepwise manner by successively enhancing genes of the L-lysine biosynthesis system as described above. A biosynthesis system comprising a plurality of reactions can be compared to a liquid flowing through a plurality of conduits having different thicknesses connected in serial. Herein each conduit corresponds to an individual enzyme, and the thickness of the conduit corresponds to an enzyme reaction velocity. In order to increase the amount of the liquid flowing through the conduits, it is effective to thicken the thinnest pipe. No effect can be expected even if a thick conduit is further thickened. In order to further increase the flow amount, the second thinnest conduit may be thickened. From such a viewpoint, the present inventors have tried to enhance the L-lysine biosynthesis system. For this purpose, as shown in Example 6 described below, the order of rate determining steps of the L-lysine biosynthesis system has been elucidated by introducing, into *E. coli,* genes of the L-lysine biosynthesis system originating from *E. coli* in a stepwise manner. In this elucidation, four genes of dapC succinyl-diaminopimelate transaminase dapD (tetrahydrodipicolinate succinylase gene) dapE (succinyldiaminopimelate deacylase gene), and dapF (diaminopimelate epimerase gene) located downstream in the biosynthesis pathway were replaced with a gene DDH coding for DDH (diaminopimelate dehydrogenase) of *Brevibacterium lactofermentum* capable of catalyzing reactions participated by these gene products by itself. Namely, introduced genes for enzymes of the L-lysine biosynthesis system and the enzymes encoded by them are as follows:

ppc: phosphoenolpyruvate carboxylase
aspC: aspartate aminotransferase
lysC: aspartokinase III
lysC*: inhibition-desensitized aspartokinase III asd: aspartate semialdehyde dehydrogenase
dapA: dihydrodipicolinate synthase
dapA*: inhibition-desensitized dihydrodipicolinate synthase
dapB: dihydrodipicolinate reductase
DDH: diaminopimelate dehydrogenase (originating from *Brevibacterium lactofermentum*)
lysA: diaminopimelate decarboxylase As a result of individual introduction of each of the genes into *E. coli*, production of L-lysine was found in strains in which lysC*, dapA or dapA* was introduced, and a dapA*-introduced strain showed the highest L-lysine productivity. According to the result, it was found that a reaction catalyzed by dapA was the first rate determining step. Next, when each of the genes of the L-lysine biosynthesis system was introduced into the dapA*-introduced strain, lysC* had the largest effect on the improvement in L-lysine productivity. Thus it was found that a reaction catalyzed by lysC was the second rate determining step. In the same manner, it was found that a reaction catalyzed by dapB was the third rate determining step, and a reaction catalyzed by DDH was the fourth rate determining step. Further, as a result of investigation on rate determining steps among reactions catalyzed by dapC, dapD, dapE and dapF replaced with DDH, it was found that dapD and dapE concerned rate determining.

A method for obtaining the genes of the L-lysine biosynthesis system of *E. coli* and the DDH gene of *Brevibacterium lactofermentum* will be exemplified below.

The ppc gene can be obtained from a plasmid pS2 (Sabe, H. et al., *Gene*, 31, 279 (1984)) or pT2 having this gene. A DNA fragment containing the ppc gene is obtained by cutting pS2 with AatII and AflII. A DNA fragment having the ppc gene is also obtained by cutting pT2 with SmaI and ScaI. An *E. coli* F15 strain (AJ12873) harboring pT2 is internationally deposited in National Institute of Bioscience and Human Technology of Agency of Industrial Science and Technology (postal code: 305, 1-3, Higashi 1-chome, Tsukuba-shi, Ibaraki-ken, Japan) under a deposition number of FERM BP-4732 based on the Budapest Treaty.

The aspc gene is obtained from a plasmid pLF4 (Inokuchi, K. et al., *Nucleic Acids Res.*, 10, 6957 (1982)) having this gene. A DNA fragment having the aspc gene is obtained by cutting pLF4 with PvuII and StuI.

The asd gene is obtained from a plasmid pAD20 (Haziza, C. et al., *EMBO*, 1, 379 (1982)) having this gene. A DNA fragment having the asd gene is obtained by cutting pAD20 with AseI and ClaI.

The dapB gene is obtained by amplifying chromosomal DNA of *E. coli* by means of the PCR method by using two species of oligonucleotide primers (for example, SEQ ID NO:9, NO:10) prepared on the basis of a nucleotide sequence of a known dapB gene (Bouvier, J. et al., *J. Biol. Chem.*, 259, 14829 (1984)).

The DDH gene is obtained by amplifying chromosomal DNA of *Brevibacterium lactofermentum* by means of the PCR method by using two species of oligonucleotide primers (for example, SEQ ID NO:11, NO:12) prepared on the basis of a known nucleotide sequence of a DDH gene of *Corynebacterium glutamicum* (Ishino, S. et al., *Nucleic Acids Res.*, 15, 3917 (1987)).

The lysA gene is obtained by amplifying chromosomal DNA of *E. coli* by means of the PCR method by using two species of oligonucleotide primers (for example, SEQ ID NO:13, NO:14) prepared on the basis of a nucleotide sequence of a known lysA gene (Stragier, P. et al., *J. Mol. Biol.*, 168, 321 (1983)).

The dapD gene is obtained by amplifying chromosomal DNA of an *E. coli* W3110 strain by means of the PCR method by using two species of oligonucleotide primers (for example, SEQ ID NO:15, NO:16) prepared on the basis of a nucleotide sequence of a known dapD gene (Richaud, C. et al., *J. Biol. Chem.*, 259, 14824 (1984)).

The dapE gene is obtained by amplifying *E. coli* DNA by means of the PCR method by using two species of oligonucleotide primers (SEQ ID NO:17, NO:18) prepared on the basis of a nucleotide sequence of a known dapE gene (Bouvier, J. et al., *J. Bacteriol.*, 174, 5265 (1992)).

The dapF gene is obtained by amplifying chromosomal DNA of *E. coli* by means of the PCR method by using two species of oligonucleotide primers (for example, SEQ ID NO:19, NO:20) prepared on the basis of a nucleotide sequence of a known dapF gene (Richaud, C. et al., *Nucleic Acids Res.*, 16, 10367 (1988)).

In the present invention, any bacterium belonging to the genus Escherichia is available for the use as a host provided that a promoter of the mutant DDPS gene, the mutant AKIII gene or another gene of the L-lysine biosynthesis system, or another promoter for expressing these genes functions in its cells, and a replication origin of a vector DNA to be used for introduction functions in its cells to be capable of replication when the mutant DDPS gene, the mutant AKIII gene or another gene of the L-lysine biosynthesis system is introduced into a plasmid as extrachromosomal DNA.

For example, there may be exemplified L-lysine-producing *E. coli*, concretely a mutant strain having resistance to L-lysine analogs. The lysine analog is such one which inhibits proliferation of bacteria belonging to the genus Escherichia, but the suppression is entirely or partially desensitized if L-lysine co-exists in a medium. For example, there are oxalysine, lysine hydroxamate, AEC, γ-methyllysine, α-chlorocaprolactam and the like. Mutant strains having resistance to these lysine analogs are obtained by applying an ordinary artificial mutation operation to microorganisms belonging to the genus Escherichia. The bacterial strain to be used for L-lysine production is concretely exemplified by *Escherichia coli* AJ11442 (deposited as FERM BP-1543 and NRRL B-12185; see Japanese Patent Application Laid-open No. 56-18596 or U.S. Pat. No. 4,346, 170). In aspartokinase of the microorganisms described above, feedback inhibition by L-lysine is desensitized.

Besides, for example, L-threonine-producing microorganisms are exemplified, because inhibition of their aspartokinase by L-lysine is generally desensitized also in the L-threonine-producing microorganisms. As an L-threonine-producing bacterium belonging to *E. coli*, a B-3996 strain has the highest producibility known at present. The B-3996 strain is deposited in Research Institute for Genetics and Industrial Microorganism Breeding under a registration number of RIA 1867.

The medium to be used for cultivation of the transformant harboring the mutant gene according to the present invention is an ordinary medium containing a carbon source, a nitrogen source, organic ions and optionally other organic components.

As the carbon source, it is possible to use sugars such as glucose, lactose, galactose, fructose, or starch hydrolysate; alcohols such as glycerol or sorbitol; or organic acids such as fumaric acid, citric acid or succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

It is desirable to allow required substances such as vitamin $B_1$ and L-isoleucine or yeast extract to be contained in appropriate amounts as organic trace nutrients. Other than the above, potassium phosphate, magnesium sulfate, iron ion, manganese ion and the like are added in small amounts, if necessary.

Cultivation is preferably carried out under an aerobic condition for 16–72 hours. The cultivation temperature is controlled at 25° C. to 45° C., and pH is controlled at 5–8 during cultivation. Inorganic or organic, acidic or alkaline substances as well as ammonia gas or the like can be used for pH adjustment.

Collection of L-lysine from a fermented liquor is usually carried out by combining an ion exchange resin method, a precipitation method and other known methods.

BEST MODE FOR CARRYING OUT THE INVENTION

The present invention will be more concretely explained below with reference to Examples.

EXAMPLE 1

Preparation of Mutant DDPS Gene

<1> Cloning of Wild Type dapA Gene

A nucleotide sequence of a dapA gene of $E.$ $coli$ has been already reported (Richaud, F. et al., $J.$ $Bacteriol.,$ 297 (1986)), and it is known that its open reading frame (ORF) comprises 876 base pairs, and codes for a protein comprising 292 amino acid residues. Since it is unknown how this dapA gene is regulated, a region containing only an SD sequence and ORF except for a promoter region was amplified by using the PCR method and cloned.

Figure 1:
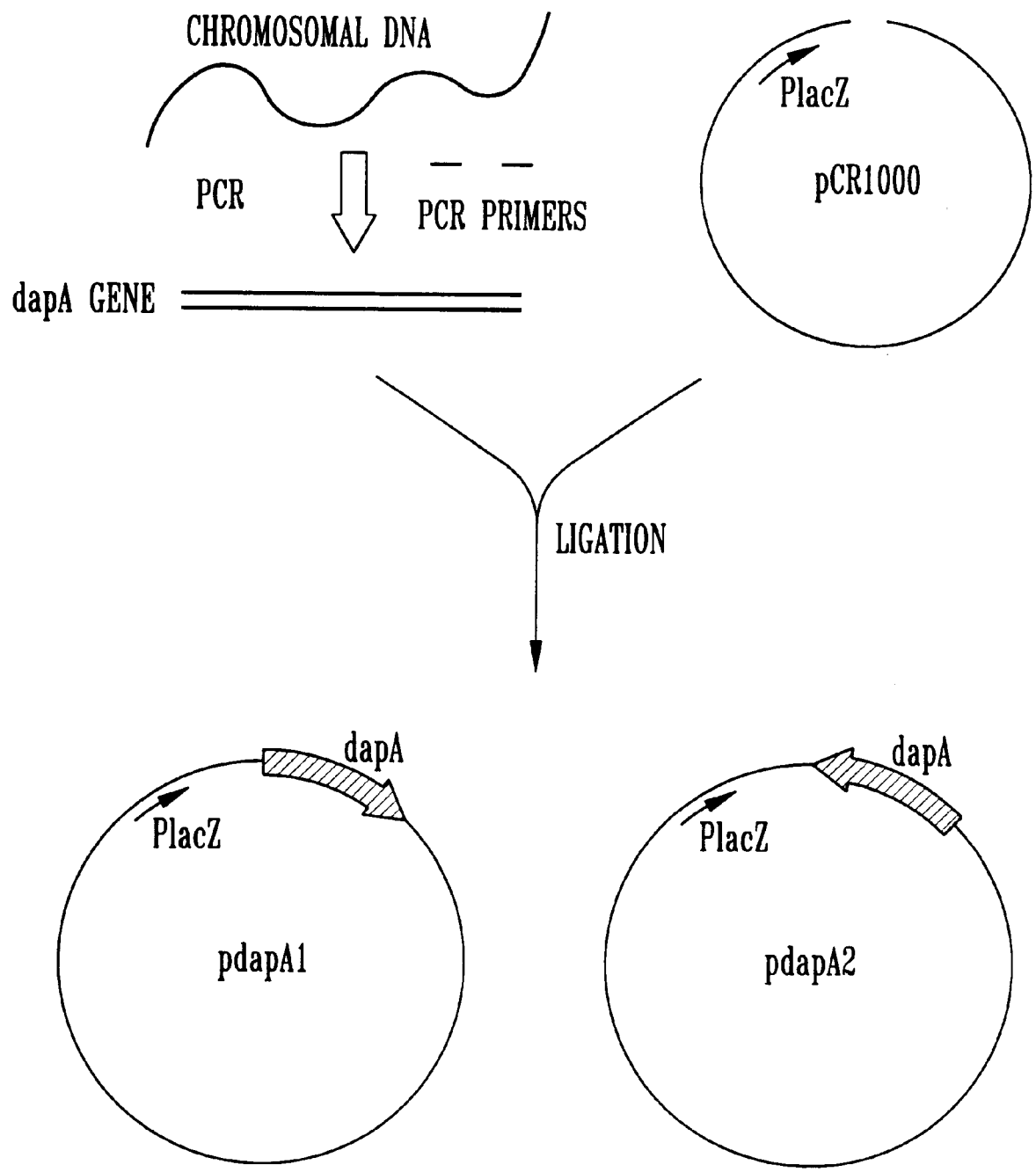
FIG. 1 shows preparation steps for pdapA1 and pdapA2.

Total genomic DNA of an $E.$ $coli$ K-12 MC1061 strain was extracted in accordance with a method of Saito and Miura ($Biochem.$ $Biophys.$ $Acta.,$ 72, 619 (1963)). Two species of primers having sequences shown in SEQ ID NO:1 and NO:2 were prepared, which were used to perform the PCR reaction in accordance with a method of Erlich et al. ($PCR$ $Technology,$ Stockton press (1989)), and target DNA was amplified. Obtained DNA was inserted into a commercially available cloning vector pCR1000 for PCR fragments (purchased from Invitrogen, Ltd., (California, the United States)) as it was. pCR1000 contains a lacZ promoter (Placz), and is sold in a state of being cut at a site downstream from the lacZ promoter. When a recombinant DNA obtained by ligating a PCR fragment between both cut termini of pCR1000 is introduced into $E.$ $coli,$ the PCR fragment is transcribed under control of the lacZ promoter. Upon ligation of the PCR fragment with PCR1000, two species of plasmids were obtained, which were pdapA1 as a plasmid ligated in a normal orientation and pdapA2 as a plasmid ligated in a reversed orientation, for the direction of transcription of dapA with respect to the direction of transcription by the lacZ promoter (FIG. 1).

When these plasmids were introduced into $E.$ $coli$ JE7627 which is a strain deficient in DDPS, strains with the introduced plasmids is complemented auxotrophy for diaminopimelic acid of the host JE7627. Thus it was confirmed that DNA fragments inserted into the both plasmids contain the gene dapA coding for active DDPS.

A transformed strain obtained by introducing pdapA1 into a wild type $E.$ $coli$ W3110 strain (available from National Institute of Genetics (Mishima-shi, Shizuoka-ken, Japan)) was designated as W3110/pdapA1, and a transformed strain obtained by introducing pdapA2 into the $E.$ $coli$ W3110 strain was designated as W3110/pdapA2, respectively. These two transformed strains were cultivated respectively in a minimal medium M9 having the following composition added with AEC as an analog of lysine. The W3110 strain with no introduced plasmid was also cultivated in the same medium as a control. These two transformed strains and the W3110 strain having no plasmid were suppressed in growth by AEC, however, their growth inhibition was recovered by addition of L-lysine.

(Minimal medium M9)

| A: | (20 × M9) | |
|---|---|---|
| | $Na_2HPO_4 \cdot 12H_2O$ | 303 g/L |
| | $KH_2PO_4$ | 60 g/L |
| | NaCl | 10 g/L |
| | $NH_4Cl$ | 20 g/L |

B: 1 M $MgSO_4$
C: 50% Glucose
D: 1 g/L Thiamine

A, B, C and D described above were separately sterilized, and mixed in a ratio of A:B:C:D: water=5:0.1:1:0.1:95.

<2> Preparation of Mutant DDPS Gene (dapA*)

It was assumed that a strain harboring a plasmid containing dapA* coding for DDDPS with desensitized inhibition by L-lysine could grow on a minimal medium M9 added with a considerable amount of AEC. A strain harboring a plasmid containing dapA* was selected by their growth resistance to AEC.

In order to efficiently obtain dapA*, dapA's on pdapA1 and pdapA2 prepared in <1> were subjected to a mutation treatment.

(1-2-1) Investigation on Selection Condition for Strain Harboring Plasmid Containing dapA*

The W3110/pdapA1 strain and the W3110/pdapA2 strain obtained as described above were cultivated on M9 agar plate media containing various concentrations of AEC, respectively. Growth inhibitory concentrations by AEC were examined, and a selection condition was investigated for a strain harboring a plasmid containing dapA*.

Growth of the transformants on the M9 media containing AEC at various concentrations is shown in Table 1. In this table, +indicates growth of transformant, and–indicates no growth.

TABLE 1

| AEC concentration (mM) | W3110/pdapA1 | W3110/pdapA2 |
|---|---|---|
| 250 | − | − |
| 125 | − | − |
| 60 | − | − |
| 30 | − | − |
| 15 | + | − |
| 8 | + | + |
| 4 | + | + |
| 2 | + | + |

The direction of transcription of the dapA gene on pdapA1 coincides with the direction of transcription by the lacZ promoter (FIG. 1). Thus it was found that the dapA gene on pdapA1 provided resistance to AEC at considerably high concentrations even when dapA remained as a wild type because its expression amount was amplified by the lacZ promoter, while the dapA gene on pdapA2 had a smaller expression amount and provided inhibition in growth by AEC at lower concentrations because the direction of transcription was in the reversed direction with respect to the lacZ promoter, and a promoter of dapA's own was also deficient (the growth was suppressed in an allotment of addition of 30 mM in the case of the W3110/pdapA1 strain, and of 15 mM in the case of the W3110/pdapA2 strain). It was confirmed that the growth inhibition was eliminated by simultaneous addition of L-lysine.

Therefore, pdapA2 was used as an object for introduction of mutation. A medium prepared by adding 60 mM of AEC to the minimal medium M9 was used for selection of a strain harboring a plasmid containing dapA*. This medium is referred to as "selection medium" in Example 1 below.

(1-2-2) In Vitro Mutation Treatment for pdapA2 with Hydroxylamine

An in vitro mutation treatment method in which plasmids are directly treated with hydroxylamine was used for introduction of mutation into the pdapA2 plasmid.

2 μg of DNA was treated at 75° C. for 1–4 hours in 0.4 M hydroxylamine (0.1 M $KH_2PO_4$-1 mM EDTA (pH 6.0): 100 μl, 1 M hydroxylamine-1 mM EDTA (pH 6.0): 80 μl, DNA: 2 μg, total: 200 μl by filling up with water). DNA after the treatment was purified with glass powder, introduced into E. coli W3110, and spread on a complete medium (L-broth: 1% Bacto trypton, 0.5% Yeast extract, 0.5% NaCl, 1.5% agar), and colonies were formed. They were replicated onto the selection medium described in (1-2-1), and those which formed colonies on the selection medium were selected. Candidates of mutant plasmids in a total of 36 strains were obtained after two times of experiments.

The candidate strains of 36 strains in total thus obtained were spotted on the selection medium again, and AEC resistance was confirmed.

(1-2-3) Isolation of dapA* Gene and Investigation on dapA* Product

Mutant pdapA2's were recovered from the 36 strains described above. A dapA-deficient strain, JE7627 was transformed with them and the wild type pdapA2, respectively. A cell-free extract was prepared from each of the transformed strains, and the enzyme activity of DDPS was measured.

The cell-free extract (crude enzyme solution) was prepared as follows. A transformed strain was cultivated in a 2×TY medium (1.6% Bacto trypton, 1% Yeast extract, 0.5% NaCl), and collected at an optical density at 660 nm ($OD_{660}$) of about 0.8. A cell pellet was washed with 0.85% NaCl under a condition of 0° C., and suspended in 20 mM potassium phosphate buffer (pH 7.5) containing 400 mM KCl. The cells were ruptured by sonication (0° C., 200 W, 10 minutes). A ruptured cell solution was centrifuged at 33 krpm for 1 hour under a condition of 0° C. to obtain a supernatant to which ammonium sulfate was added to give 80% saturation to be stored at 0° C. overnight followed by centrifugation. A pellet was dissolved in 20 mM potassium phosphate buffer (pH 7.5)-400 mM KCl.

The enzyme activity of DDPS was measured in accordance with a method of Yugari et al. (Yugari, Y. and Gilvarg, C., J. Biol. Chem., 240, 4710 (1962)). Namely, the absorbance of a reaction solution having the following composition was measured at 37° C. with a spectrophotometer at a wavelength of 270 nm in a time-dependent manner. And generated dihydrodipicolinate was measured. Sodium pyruvate was removed from the reaction system to be used as a blank.

(Composition of Reaction Solution)

Figure 2:
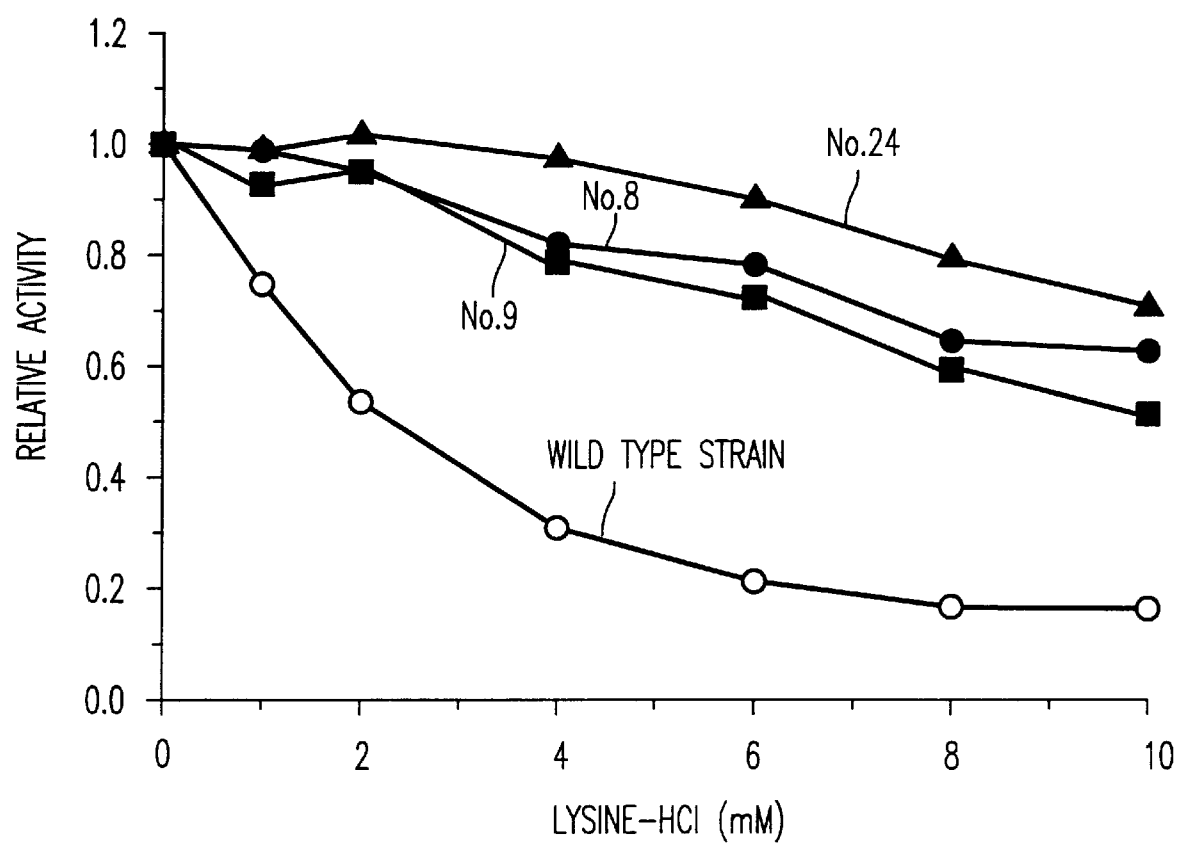
FIG. 2 shows inhibition by L-lysine for wild type and mutant DDPS's.

50 mM imidazole-HCl pH 7.4
20 mM L-aspartate semialdehyde
20 mM sodium pyruvate
enzyme solution
water (balance)
    total 1.0 ml Various concentrations of L-lysine were added to the enzyme reaction solution during measurement of the enzyme activity of DDPS, and the degree of inhibition by L-lysine was examined. As shown in FIG. 2, the wild type DDPS suffered inhibition by L-lysine. Mutant plasmids originating from the transformed strains having DDPS difficult to suffer inhibition by L-lysine as compared with the wild type were three species among the 36 species of the candidate plasmids. They were designated as pdapAS8, pdapAS9 and pdapAS24, respectively. According to following determination of nucleotide sequences, it was revealed that pdapAS8 and pdapAs9 had the same mutation.

The degree of desensitization of inhibition by L-lysine was varied in the three species of mutant DDPS encoded by pdapAS8, pdapAS9 and pdapAS24, however, the inhibition by L-lysine was desensitized in all of the three species. Although the specific activity of the enzyme might be affected by growth situations of cells and preparation of samples, it was found to be lowered a little in any case as compared with the wild type. However, it was judged that no substantial problem would be caused by them as a material for breeding.

(1-2-4) Determination of Nucleotide Sequence of Mutant dapA Gene

Nucleotide sequences of the mutant dapA genes were determined in accordance with an ordinary method by using a DNA sequencer ABI Model 373A (produced by Applied Biosystems Inc.). As a result, it was revealed that 487th C was changed to T in pdapAS8 and pdapAS9, and 597th C was changed to T in pdapAS24 on a sequence of the wild type dapA gene shown in SEQ ID NO:3. Therefore, it was revealed that a 81st alanine residue was changed to a valine residue in DDPS encoded by pdapAS8 and pdapAS9, and a 118th histidine residue was changed to a tyrosine residue in DDPS encoded by pdapAS24 in an amino acid sequence of DDPS shown in SEQ ID NO:4.

(1-2-5) Preparation of dapA Having Double Mutation

Figure 3:
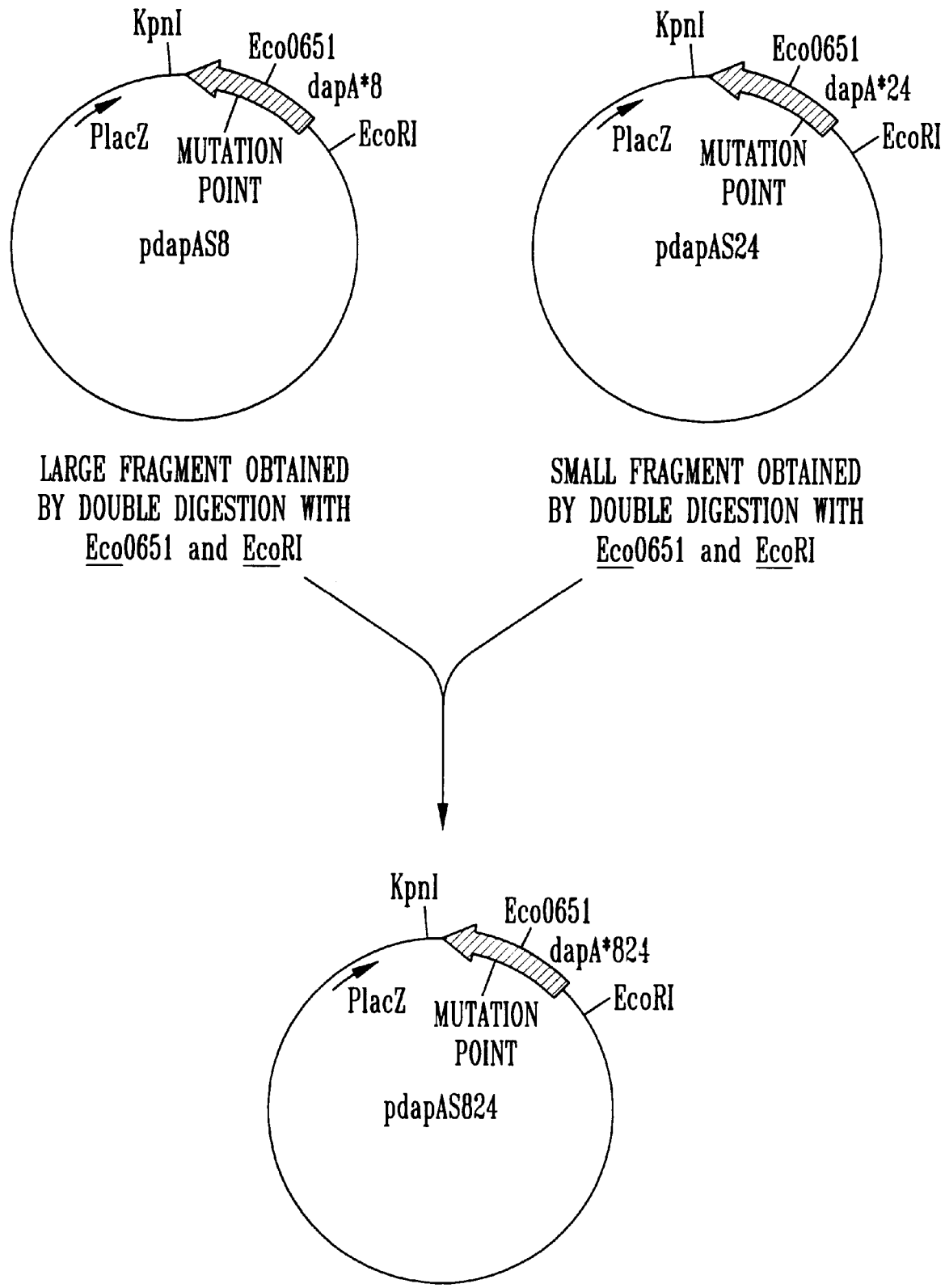
FIG. 3 shows preparation steps for a plasmid pdapAS824 having a double mutation type dapA* gene.

Two species of the mutant dapA genes were obtained as described above. In order to verify whether or not desensitization of inhibition works additively for these mutations, a plasmid containing mutant dapA having both of the two mutations was prepared. A procedure of preparation is as shown in FIG. 3. An obtained plasmid having double mutation was designated as pdapAS824.

EXAMPLE 2

Preparation of Mutant AKIII Gene

<1> Cloning of Wild Type lysC Gene

A nucleotide sequence of an AKIII gene (lysC) of *E. coli* has been already reported (Cassan, M., Parsot, C., Cohen, G. N., and Patte, J. C., *J. Biol. Chem.*, 261, 1052 (1986)), and it is known that its open reading frame (ORF) comprises 1347 base pairs, and codes for a protein comprising 449 amino acid residues. An operator is present in this gene, and is subjected to suppression by L-lysine. Thus in order to remove the operator region, a region containing only an SD sequence and ORF was amplified by using the PCR method and cloned.

Figure 4:
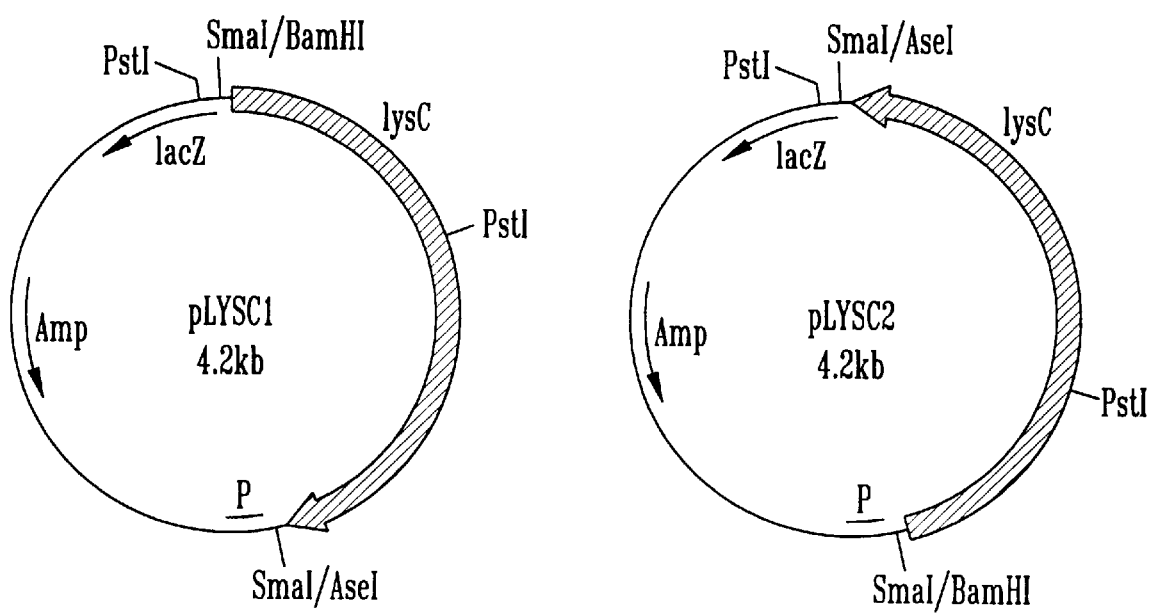
FIG. 4 shows preparation steps for pLYSC1 and pLYSC2.

Total genomic DNA of an *E. coli* K-12 MC1061 strain was prepared in accordance with a method of Saito and Miura (*Biochem. Biophys. Acta.*, 72, 619 (1963)). Two species of primers having sequences shown in SEQ ID NO:5 and NO:6 were prepared, which were used to perform the PCR reaction in accordance with a method of Erlich et al. (*PCR Technology*, Stockton press (1989)), and the lysc gene was amplified. Obtained DNA was digested with BamHI and AseI, then blunt-ended, and inserted into a SmaI site of a multi-copy vector, pUC18. This SmaI site is located at a downstream side from a lacZ promoter existing in the vector, and when recombinant DNA obtained by inserting a DNA fragment into the SmaI site of pUC18 is introduced into *E. coli*, the inserted DNA fragment is transcribed by means of read-through transcription under the control by the lacZ promoter. Upon insertion of the PCR fragment into the SmaI site of pUC18, two species of plasmids were obtained, which were pLYSC1 as a plasmid inserted in a reversed orientation and pLYSC2 as a plasmid inserted in a normal orientation, for the direction of transcription of lysC with respect to the direction of transcription by the lacZ promoter (FIG. 4).

When these plasmids were used to transform *E. coli* GT3 (thrA1016b, metLM1005, lysC1004) as a completely deficient strain for AKI, II, III, auxotrophy of GT3 for homoserine and diaminopimelic acid was complemented. Thus it was confirmed that DNA fragments inserted into the both plasmids contain the gene lysC coding for active AKIII.

A transformed strain obtained by introducing pLYSC1 into the AK completely deficient strain, *E. coli* GT3 was designated as GT3/pLYSC1, and a transformed strain obtained by introducing pLYSC2 into the *E coli* GT3 was designated as GT3/pLYSC2. A considerable amount of L-lysine was added to the minimal medium M9, and the GT3/pLYSC1 strain and the GT3/pLYSC2 strain were cultivated, respectively. Both of the GT3/pLYSC1 strain and the GT3/pLYSC2 strain harbor plasmids containing the wild type lysC, in which AKIII encoded by lysC on the plasmids is a sole AK. The wild type AKIII as the sole AK is inhibited by L-lysine in the presence of a considerable amount of L-lysine. Thus the both strains could not synthesize L-threonine, L-isoleucine, L-methionine and diaminopimelic acid (DAP), and were suppressed in growth.

<2> Preparation of Mutant AKIII Gene (lysC*)

It was assumed that a strain harboring a plasmid containing lysc* coding for AK with desensitized inhibition by L-lysine could grow on a minimal medium M9 added with a considerable amount of L-lysine. A strain harboring a plasmid containing lysC* was selected by selecting strains with their growth resistant to L-lysine or AEC as an analog of L-lysine.

In order to efficiently obtain lysc*, lysc's on pLYSC1 and pLYSC2 prepared in <1> were subjected to a mutation treatment.

(2-2-1) Investigation on Selection Condition for Strain Harboring Plasmid Containing lysC*

The GT3/pLYSC1 strain and the GT3/pLYSC2 strain were cultivated on M9 agar plate media containing various concentrations of L-lysine or AEC, respectively. Growth inhibitory concentrations by L-lysine or AEC were examined, and a selection condition was investigated for a strain harboring a plasmid containing lysC*.

Growth of the transformants on the M9 media containing L-lysine or AEC at various concentrations is shown in Table 2. In this table, + indicates growth of transformant, ± indicates a little growth, and – indicates no growth.

TABLE 2

| | Growth and L-lysine concentration | | | | | | | | | | | |
|---|---|---|---|---|---|---|---|---|---|---|---|---|
| | 0 | 0.2 | 0.4 | 0.8 | 1.5 | 3 | 6 | 12 | 25 | 50 | 100 | 200 | (mM) |
| GT3/pLYSC1 | + | – | – | – | – | – | – | – | – | – | – | – | |
| GT3/pLYSC2 | + | + | + | + | + | + | + | + | + | + | + | – | |
| | Growth and AEC concentration | | | | | | | | | | | |
| | 0 | 0.2 | 0.4 | 0.8 | 1.5 | 3 | 6 | | 12 | 25 | 50 | (mM) |
| GT3/pLYSC1 | + | – | – | – | – | – | – | | – | – | – | |
| GT3/pLYSC2 | + | ± | ± | ± | ± | ± | – | | – | – | – | |

The direction of transcription of the lysC gene on pLYSC2 coincides with the direction of transcription by the lacZ promoter (FIG. 4). Thus it was found that the lysc gene on pLYSC2 provided resistance to L-lysine and AEC at considerably high concentrations even when lysC remained as a wild type because its expression amount was amplified by the lacZ promoter, while the lysC gene on pLYSC1 had a smaller expression amount and provided inhibition in growth by L-lysine and AEC at lower concentrations because the direction of transcription was in the reversed direction with respect to the lacZ promoter, and a promoter of itself was also deficient (the growth was not suppressed up to an allotment of addition of 100 mM for L-lysine and up to an allotment of addition of 3 mM for AEC in the case of the GT3/pLYSC2 strain, while the growth was completely suppressed in an allotment of addition of 0.2 mM for both L-lysine and AEC in the case of GT3/pLYSC1 strain). It was confirmed that the growth inhibition was eliminated by simultaneous addition of homoserine and diaminopimelic acid.

Therefore, pLYSC1 was used for experiments of introduction of mutation. A medium prepared by adding 10 mM of L-lysine or 0.2 mM of AEC to the minimal medium M9 was used for selection of plasmid-harboring strains containing lysC*. This medium is referred to as "selection medium" in Example 2 below.

(2-2-2) In Vitro Mutation Treatment for pLYSC1 with Hydroxylamine

Two kinds of methods were used for introduction of mutation into the pLYSC1 plasmid, which were an in vitro mutation treatment method in which plasmids are directly treated with hydroxylamine, and an additional in vivo mutation treatment method in which a cell harboring a plasmid is treated with nitrosoguanidine (NTG) followed by extraction of the plasmid in order to provide diversity of mutation, namely expecting mutation other than the mutation from cytosine to thymine with hydroxylamine.

(In Vitro Mutation Treatment with Hydroxylamine)

Figure 5:
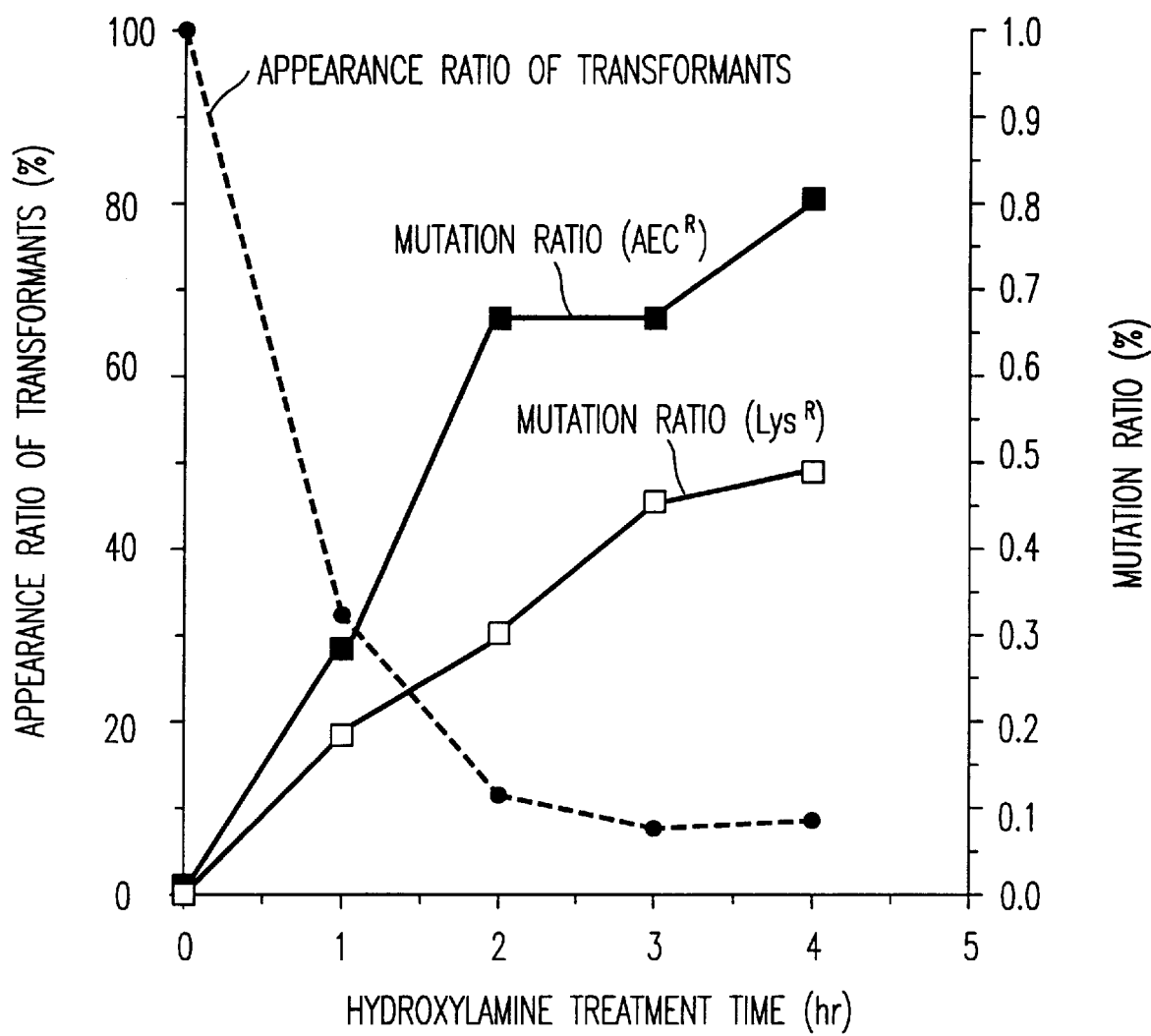
FIG. 5 shows an appearance ratio and a mutation ratio of transformants after a hydroxylamine treatment.

2 μg of DNA was treated under a condition of 75° C. for 1–4 hours in 0.4 M hydroxylamine (0.1 M $KH_2PO_4$-1 mM EDTA (pH 6.0): 100 μl, 1 M hydroxylamine-1 mM EDTA (pH 6.0): 80 μl, DNA: 2 μg, total: 200 μl by filling up with water). DNA after the treatment was purified with glass powder, introduced into an AK completely deficient strain, an E. coli GT3 strain, and spread on a complete medium (L-broth: 1% Bacto trypton, 0.5% Yeast extract, 0.5% NaCl, 1.5% agar), and colonies were formed. They were replicated onto the selection medium described in (2-2-1), and strains capable of growth on the selection medium were selected as candidate strains. The appearance ratio of transformants and the mutation ratio were found to proceed as shown in FIG. 5. Mutant strains were obtained by a treatment for 4 hours at a considerably high ratio of 0.5–0.8%.

(In Vivo Mutation Treatment with NTG)

pLYSC1 was introduced into E. coli MC1061, and an NTG treatment was performed with a whole cell. The cell after the treatment was cultivated overnight to fix mutation, and then a plasmid was extracted and introduced into E. coli GT3. Namely, the transformed strain was cultivated in a 2×TY medium (1.6% Bacto trypton, 1% Yeast extract, 0.5% NaCl), collected at an $OD_{660}$ of about 0.3, washed with a TM buffer described below, then suspended in an NTG solution (prepared by dissolving NTG at a concentration of 0.2 mg/ml in TM buffer), and treated at 37° C. for 0–90 minutes. The cell was washed with TM buffer and 2×TY medium, and then mutation was fixed by cultivation in 2×TY medium overnight. Subsequently plasmid DNA was extracted from the cell, and introduced into an E. coli GT3 strain. Screening of candidate strains was performed in the same manner as in the in vitro mutation, and mutants of lysine resistance ($Lys^R$) and AEC resistance ($AEC^R$) were obtained.

| (TM buffer) | |
|---|---|
| Tris | 50 mM |
| Maleic acid | 50 mM |
| $(NH_4)_2SO_4$ | 1 g/L |
| $MgSO_4·7H_2O$ | 0.1 g/L |
| $Ca(NO_3)2$ | 5 mg/L |
| $FeSO_4·7H_2O$ | 0.25 mg/L | pH was adjusted to 6.0 with NaOH.

Total 180 strains of candidate strains obtained as described above (hydroxylamine treatment: 48 strains, NTG treatment: 132 strains) were spotted on the selection medium again, and AEC and L-lysine resistances were confirmed to obtain 153 strains. Taking a notice of difference in amino acid accumulation pattern in the medium, these 153 strains were divided into 14 groups, and the AK activity was measured after selecting representative strains of each of the groups. There was no large difference in AK activity between the mutant strains obtained by the hydroxylamine treatment and the mutant strains obtained by the NTG treatment. Thus the following experiments were performed without distinguishing them.

(2-2-3) Isolation of lysc* Gene and Investigation on lysc* Product

No. 24, No. 43, No. 48, No. 60, No. 80, No. 117, No. 126, No. 149, No. 150, No. 156, No. 158, No. 167, No. 169 and No. 172 were selected as representative strains of the aforementioned 14 groups. Mutant plasmids derived from pLYSC1 were recovered from each of them, and designated as pLYSC1*24, pLYSC1*43, pLYSC1*48, pLYSC1*60, pLYSC1*80, pLYSC1*117, pLYSC1*126, pLYSC1*149, pLYSC1*150, pLYSC1*156, pLYSC1*158, pLYSC1*167, pLYSC1*169 and pLYSC1*172, respectively. An AK completely deficient strain GT3 was transformed with them and the wild type pLYSC1. A cell-free extract was prepared from each of transformed strains, and the enzyme activity of AKIII was measured.

The cell-free extract (crude enzyme solution) was prepared as follows. A transformed strain was cultivated in a 2×TY medium, and collected at an $OD_{660}$ of about 0.8. Cells were washed with 0.02 M $KH_2PO_4$ (pH 6.75)-0.03 M β-mercaptoethanol under a condition of 0° C., and the cells were ruptured by sonication (0° C., 100 W, 30 minutes×4). A ruptured cell solution was centrifuged at 33 krpm for 1 hour under a condition of 0° C. to obtain a supernatant, to which ammonium sulfate was added to give 80% saturation. After centrifugation, a pellet was dissolved in 0.02 M $KH_2PO_4$ (pH 6.75)-0.03 M β-mercaptoethanol, and stored at 0° C. overnight.

The enzyme activity of AKIII was measured in accordance with a method of Stadtman et al. (Stadtman, E. R., Cohen, G. N., LeBras, G., and Robichon-Szulmajster, H., J. Biol. Chem., 236, 2033 (1961)). Namely, a reaction solution having the following composition was incubated at 27° C. for 45 minutes, and an $FeCl_3$ solution (2.8 N HCl 0.4 ml +12% TCA 0.4 ml +5% $FeCl_3$. $6H_2O$/0.1 N HCl 0.7 ml) was added to develop a color, which was centrifuged followed by measurement of absorbance of a supernatant at 540 nm. The activity was indicated by an amount of hydroxamic acid generated per minute (1 U=1 μmol/min). The molar absorption coefficient was 600. Potassium aspartate was removed from the reaction solution to be used as a blank.

(Composition of Reaction Solution)

| | |
|---|---|
| Reaction mixture *1 | 0.3 ml |
| Hydroxylamine solution *2 | 0.2 ml |
| 0.1 M Potassium aspartate (pH 7.0) Enzyme solution | 0.1 ml |
| Water | (balance) |
| | total 1.0 ml |

*1: 1 M Tris-HCl (pH 8.1) 9 ml + 0.3 M MgSO$_4$ 0.5 ml + 0.2 M ATP (pH 7.0) 5 ml
*2: 8 M Hydroxylamine solution was neutralized just before use with KOH.

Figure 6A:
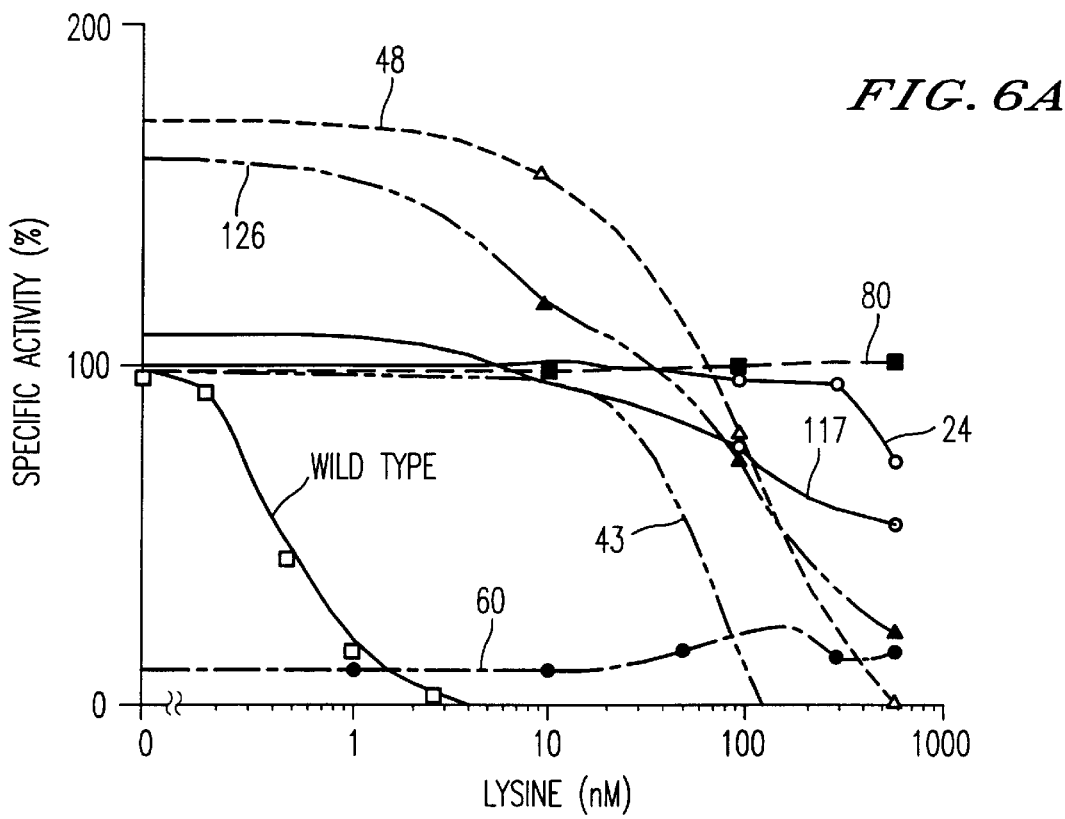
FIG. 6 shows inhibition by L-lysine for wild type and mutant AKIII's.
Figure 6B:
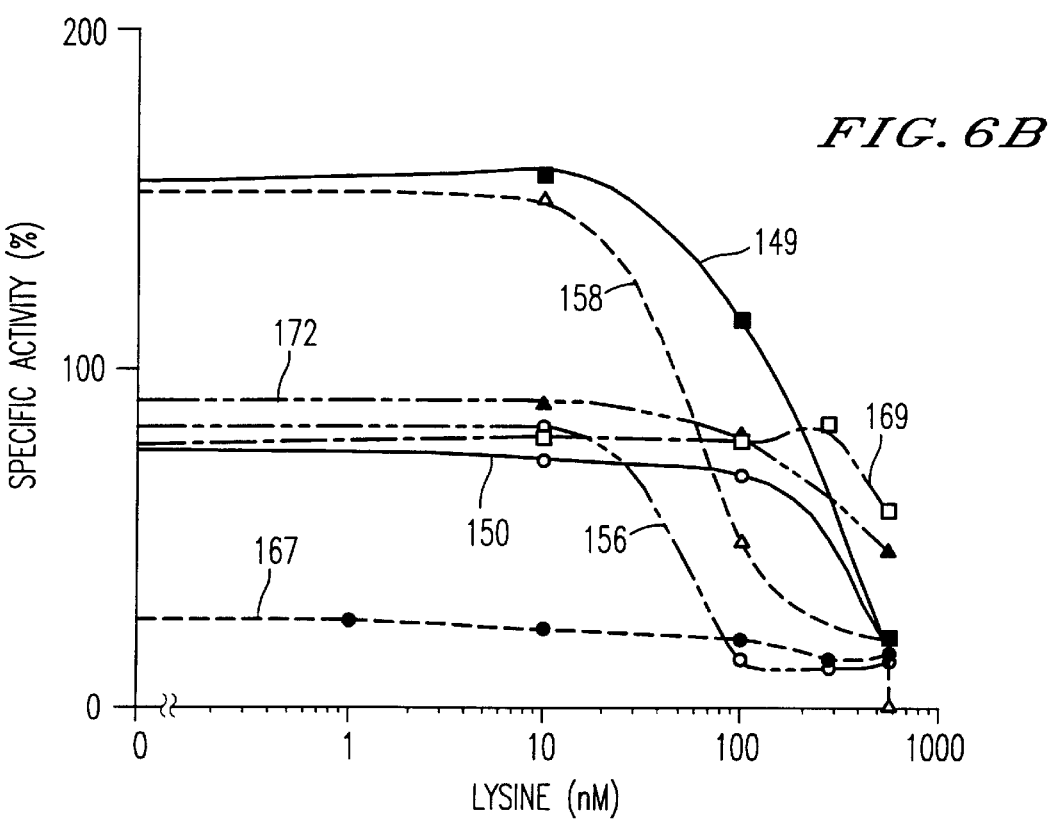

Various concentrations of L-lysine were added to the enzyme reaction solution for measurement of the enzyme activity of AK, and the degree of inhibition by L-lysine was examined. Results are shown in FIG. 6 and Table 3. The wild type and Nos. 24, 43, 48, 60, 80, 117 and 126 are shown in FIG. 6A. Nos. 149, 150, 156, 158, 167, 169 and 172 are shown in FIG. 6B.

As shown in these results, the wild type AKIII strongly suffered inhibition by L-lysine, which was inhibited by 50% at about 0.45 mM of L-lysine, and inhibited by about 100% at 5 mM. On the contrary, the mutant AKIII's obtained this time had various degrees of desensitization, however, inhibition by L-lysine was desensitized in all of 14 species. Especially in the case of Nos. 24, 80, 117, 169 and 172, inhibition was scarcely observed even at 100 mM of L-lysine, and they had 50%-inhibitory-concentrations which were not less than 200 times as compared with that of the wild type. The specific activity per total protein, which might be affected by growth situations of cell and preparation of samples, was equal to or more than that of the wild type in almost all cases, in which there was little problem of decrease in activity due to the introduction of mutation (Table 3). According to this fact, it was postulated that an active center of AKIII was independent from a regulatory site by L-lysine with each other. In Table 3, the inhibition desensitization degree (%) refers to an AK activity in the presence of 100 mM of L-lysine with respect to an AK activity in the absence of L-lysine in the reaction solution. The heat stability (%) refers to a ratio of activity maintenance after a treatment at 55° C. for 1.5 hour.

TABLE 3

| | Specific activity (U/mg protein) | Degree of desensitization of inhibition (%)*1 | Heat stability (%)*2 |
|---|---|---|---|
| Wild type | 0.0247 | 0 | 18 |
| No. 117 | 0.0069 | 120 | 0 |
| No. 24 | 0.0218 | 100 | 30 |
| No. 80 | 0.0244 | 99 | 36 |
| No. 172 | 0.0189 | 97 | 0 |
| No. 169 | 0.0128 | 96 | 2 |
| No. 150 | 0.0062 | 77 | 25 |
| No. 126 | 0.0250 | 61 | 39 |
| No. 149 | 0.0256 | 59 | 9 |
| No. 167 | 0.0083 | 43 | 45 |
| No. 48 | 0.0228 | 38 | 42 |
| No. 60 | 0.0144 | 35 | 9 |
| No. 158 | 0.0224 | 22 | 42 |
| No. 156 | 0.0101 | 18 | 2 |
| No. 43 | 0.0212 | 17 | 0 |

*1: AK activity (%) in the presence of 100 mM of L-lysine with respect to AK activity in the absence of L-lysine
*2: ratio of activity maintenance (%) after treatment at 55° C. for 1.5 hour Subsequently, the heat stability of the mutant enzymes was examined. When it is intended that an enzyme is improved to increase its activity, it is important that a created enzyme is maintained stably in cells. Measurement in vitro has some problems because of the difference in intracellular and extracellular protease activities and the influence of buffers for in vitro storage of enzymes. However, for convenience, the heat stability of the mutant AKIII's was investigated in vitro as one parameter.

Judging from results of investigation on the inactivation temperature of AKIII under various conditions, the ratio of activity maintenance after a treatment at 55° C. for 90 minutes was measured. As shown in Table 3, half the enzymes were rather more excellent than the wild type. Generally, a mutant enzyme is often unstable as compared with a wild type. However, some of the mutant AKIII's obtained this time were superior to the wild type in stability, and many of them seemed to be fairly useful in practical use for L-lysine production.

(2-2-4) Determination of Base Sequence of Wild Type lysC and Mutant lysC

A nucleotide sequence of the wild type lysC gene obtained this time was determined in accordance with an ordinary method by using a DNA sequencer ABI Model 373A (produced by Applied Biosystems Inc.) (SEQ ID NO:7). As a result, differences were found in six sites (two places at the amino acid level) from an already published sequence of lysc of an E. coli K-12 JC411 strain (Cassan, M., Rarsot, C., Cohen, G. N., and Patte, J. C., J. Biol. Chem., 261, 1052 (1986)). It is speculated that the difference in six sites is due to the difference in bacterial strain used.

In the same manner, base sequences were determined for each of lysC*'s existing on the 14 species of mutant pLYSC1's, and mutation points were clarified. Results are shown in Table 4. In this table, indications in parentheses show mutations of amino acid residues based on mutations of nucleotides. Types of mutations were 12 kinds because two sets (No. 4 and No. 167, No. 24 and No. 80) had exactly the same mutation types among the 14 species. With respect to mutation types, Nos. 149, 150, 156, 158, 167, 169 and 172 were obtained by the hydroxylamine treatment, and Nos. 24, 43, 48, 60, 80, 117 and 126 were obtained by the NTG treatment. However, as for the pattern of mutation, any of them resided in mutation from cytosine to thymine, or mutation from guanine to adenine on a coding strand due to mutation from cytosine to thymine on a noncoding strand.

TABLE 4

Determination of mutation points of lysC*

| lysC* mutation type | Mutagen | Mutation point (amino acid change) |
|---|---|---|
| No. 126 | N | GGT→GA*T ($^{323}$Gly→Asp) |
| No. 43 | N | GGT→GA*T ($^{323}$Gly→Asp) |
| | | GGC→GA*C ($^{408}$Gly→Asp) |
| No. 149 | H | CGT→T*GT ($^{34}$Arg→Cys) |
| | | GGT→GA*T ($^{323}$Gly→Asp) |
| No. 48/167 | N/H | CTC→T*TC ($^{325}$Leu→Phe) |
| No. 150 | H | ATG→ATA* ($^{318}$Met→Ile) |
| No. 172 | H | $^{775}$C→T (silent) |
| | | ATG→ATA* ($^{318}$Met→Ile) |
| | | GTG→A*TG ($^{349}$Val→Met) |
| No. 117 | N | TCA→TT*A ($^{345}$Ser→Leu) |
| No. 158 | H | GTG→A*TG ($^{347}$Val→Met) |
| No. 24/80 | N/N | ACC→AT*C ($^{352}$Thr→Ile) |
| No. 169 | H | $^{923}$C→T (silent) |
| | | ACC→AT*C ($^{352}$Thr→Ile) |
| | | TCT→TT*T ($^{369}$Ser→Phe) |
| No. 60 | N | $^{859}$G→A (silent) |
| | | GAA→A*AA ($^{164}$Glu→Lys) |
| No. 156 | H | ATG→ATA* ($^{417}$Met→Ile) |
| | | TGT→TA*T ($^{419}$Cys→Tyr) |
| | | $^{2014}$C→T (silent) |

*: H; hydroxylamine treatment, N; NTG treatment

EXAMPLE 3

Fermentation Production of L-lysine with Strain Being Introduced daDA*

In order to produce L-lysine by using *E. coli*, as indicated in Japanese Patent Application Laid-open No. 56-18596, U.S. Pat. No. 4,346,170 and *Applied Microbiology and Biotechnology*, 15, 227–231 (1982), it is considered to be essential that a host for enhancing DDPS has an aspartokinase which is changed not to suffer inhibition by L-lysine. L-threonine-producing bacteria may be exemplified as such a strain. As for L-threonine-producing *E. coli*, a B-3996 strain has the highest productivity among those known at present. Thus the B-3996 strain was used as a host for evaluating dapA*. The B-3996 strain harbors pVIC40 extra-chromosomally as a sole plasmid. Details are described in Japanese Patent Laid-open No. 3-501682 (PCT). This microorganism is deposited in Research Institute for Genetics and Industrial Microorganism Breeding under a registration No. of RIA 1867.

Figure 7:
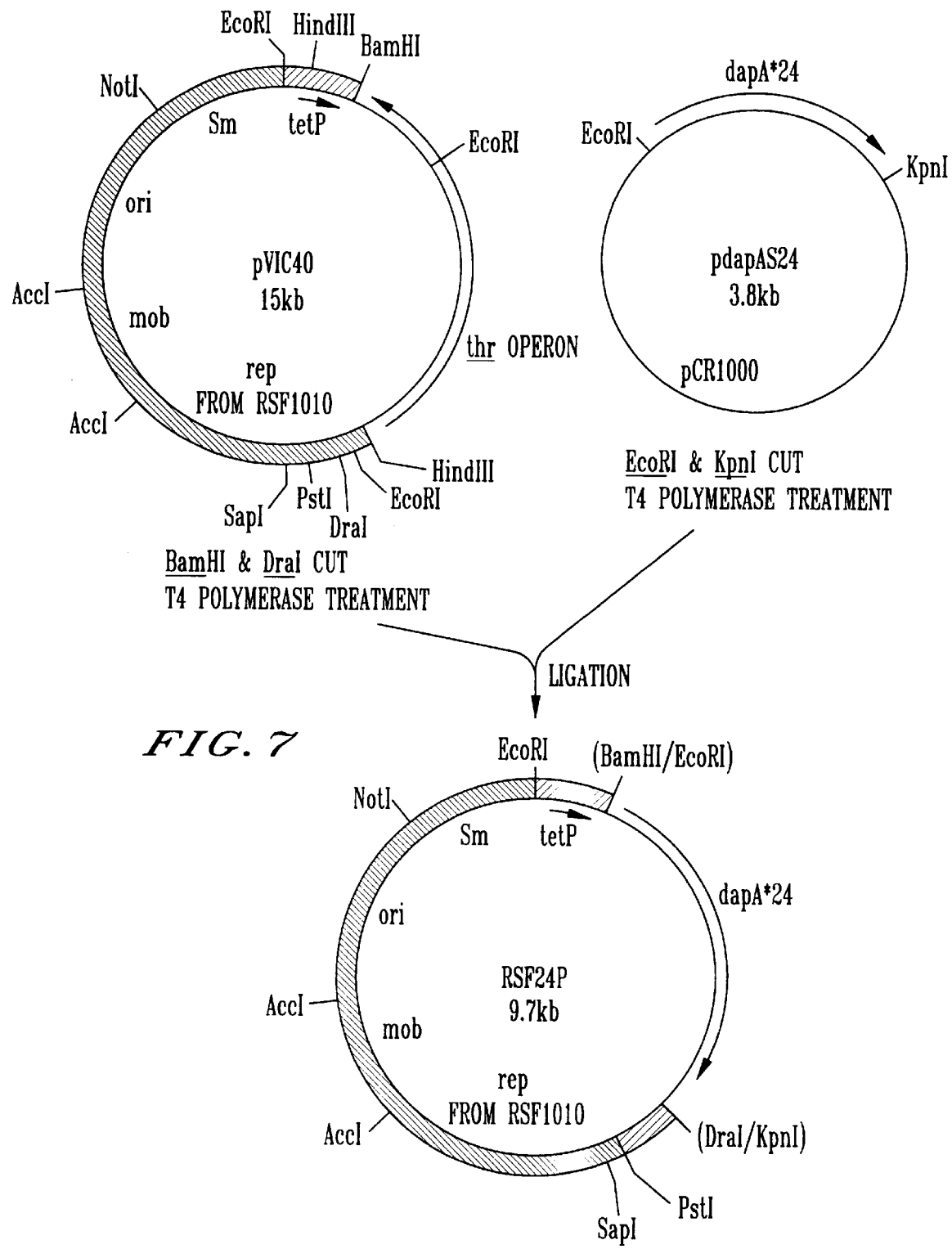
FIG. 7 shows preparation steps for a plasmid RSF24P originating from RSF1010 having dapA*24.

On the other hand, dapA* contained in pdapAS24 (in which the 118th histidine residue replaced with a tyrosine residue) was selected as dapA* to be introduced into *E. coli*, judging from the degree of desensitization of inhibition and the specific activity of the enzyme. At first, in order to increase the expression amount of dapA* and increase stability of the plasmid, mutant dapA* having existed on pdapAS24 (hereinafter referred to as "dapA*24") was ligated at the downstream from a promoter of a tetracycline resistance gene of pVIC40, and RSF24P was obtained as shown in FIG. 7.

A strain obtained by introducing the plasmid RSF24P into an *E. coli* JM109 strain was designated as AJ12395, which is deposited in National Institute of Bioscience and Human Technology of Agency of Industrial Science and Technology on October 28, 1993, as accession number of FERM P-13935, and transferred from the original deposition to international deposition based on Budapest Treaty on Nov. 1, 1994, and has been deposited as accession number of FERM BP-4858. Strains harboring pdapAS8 and pdapAS9 were not deposited. However, all of the mutation points of dapA* on each of the plasmids have been clarified as described above. Thus it is easy for those skilled in the art that the plasmid is recovered from the aforementioned deposited bacterium by using a method of Maniatis et al. (Sambrook, J., Fritsch, E. F., Maniatis, T., *Molecular Cloning*, Cold Spring Harbor Laboratory Press, 1.21 (1989)), and a target gene is obtained by using a site-directed mutagenesis method (Sambrook, J., Fritsch, E. F., Maniatis, T., *Molecular Cloning*, Cold Spring Harbor Laboratory Press, 15.63 (1989)).

pVIC40 was deleted from the B-3996 strain in accordance with an ordinary method, and a B-399 strain was obtained as a strain having no plasmid. The plasmid RSF24P was introduced into the B-399 strain in accordance with an ordinary method, and B-399/RSF24P was obtained. The L-lysine productivity of B-399/RSF24P was evaluated.

On the other hand, RSFP was constructed as a control plasmid. Namely, a large fragment was selected from digest of pVIC40 double-degested with BamHI and DraI as shown in FIG. 7, and it was blunt-ended with DNA polymerase Klenow fragment. The blunt-ended large fragment was self-ligated to obtain the plasmid RSFP. RSFP was introduced into the B-399 strain in accordance with an ordinary method, and B-399/RSFP was obtained. The L-lysine productivity was also evaluated for B-399/RSFP.

The cultivation was performed at an agitation of 114–116 rpm under a condition of a cultivation period of 48 hours and a temperature of 37° C. by using the following medium. Results are shown in Table 5.

(Medium for L-lysine Production)

| | | |
|---|---|---|
| A: | $(NH_4)_2SO_4$ | 16 g/L |
| | $KH_2PO_4$ | 1 g/L |
| | $MgSO_4 \cdot 7H_2O$ | 1 g/L |
| | $FeSO_4 \cdot 7H_2O$ | 0.01 g/L |
| | $MnSO_4 \cdot 5H_2O$ | 0.01 g/L |
| | Yeast Ext. (Difco) | 2 g/L |
| | L-methionine | 0.5 g/L |
| | L-threonine | 0.1 g/L |
| | L-isoleucine | 0.05 g/L |
| | pH is adjusted to 7.0 with KOH to be autoclave at 115° C. for 10 minutes. | (16/20 volume) |
| B: | 20% Glucose (autoclave at 115° C. for 10 minutes) | (4/20 volume) |
| C: | Pharmacopoeial $CaCO_3$ (heat-sterilized in dry state at 180° C. for 2 days) | (30 g/L) |

A and B are mixed in the ratio of A:B=4:1, 30 g of C is added to 1 L of the mixture and dissolved, and antibiotics (streptomycin: 100 µg/ml, kanamycin: 5 µg/ml) are added.

TABLE 5

| Bacterial strain | Production amount of L-lysine hydrochloride |
|---|---|
| B-399/RSF24P | 4.1 g/L |
| B-399/RSFP | 0 g/L |

EXAMPLE 4

Fermentation Production of L-lysine with Strain Being Introduced dapA* and lysC* (I)

Figure 8:
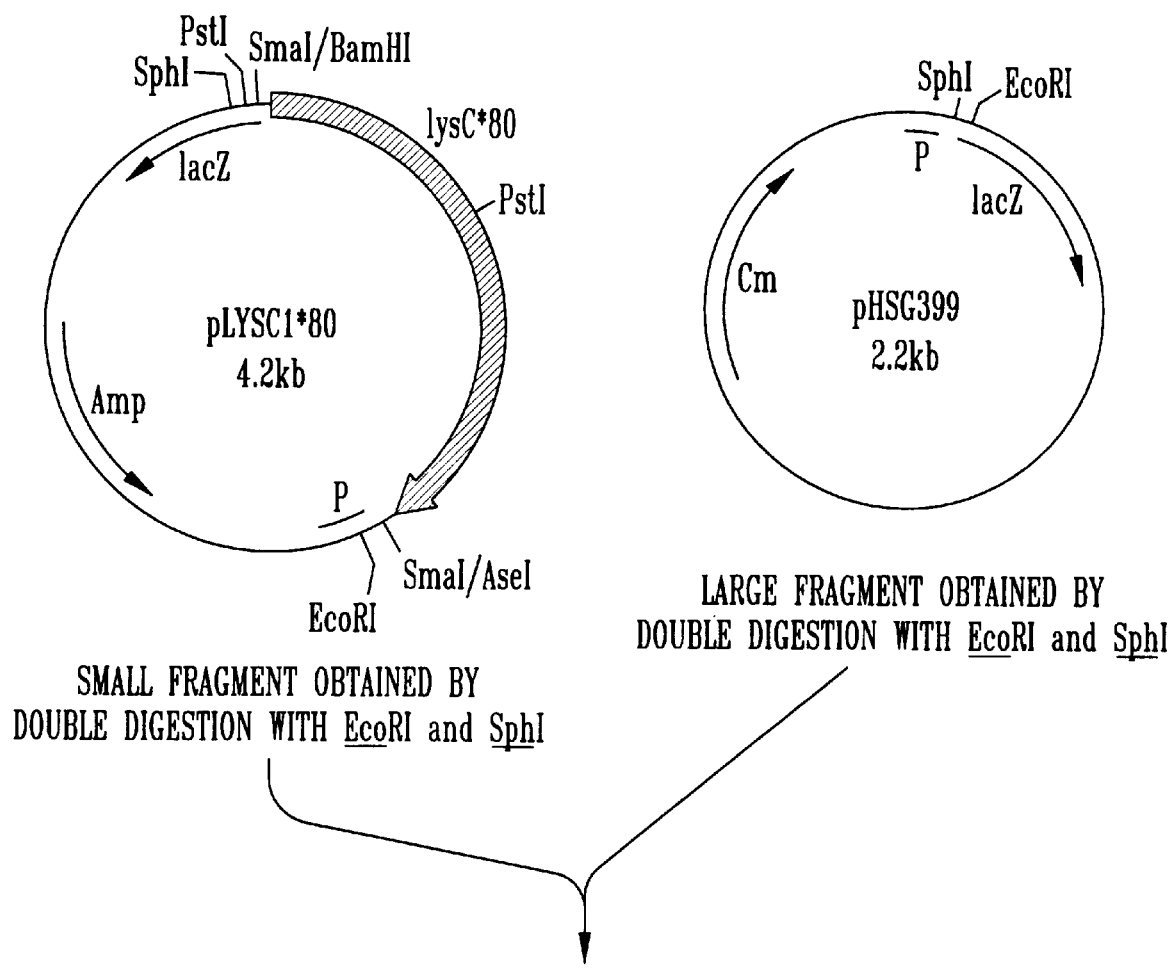
FIG. 8 shows preparation steps for a plasmid pLLC*80.
Figure 8:
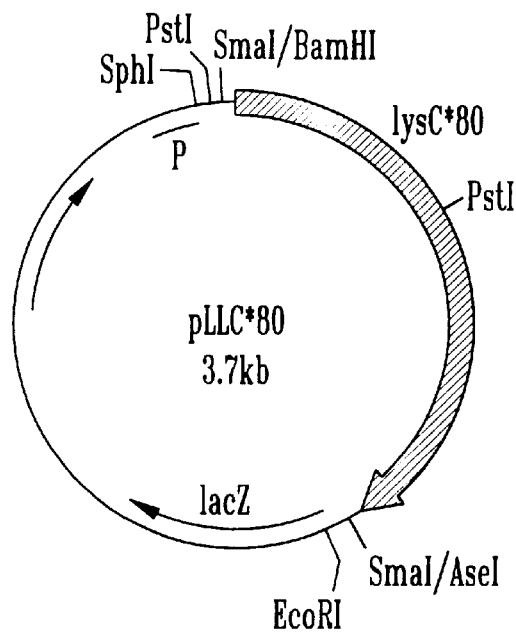

The effect of the mutant DDPS on L-lysine production has been shown in Example 3. In order to achieve further improvement, the mutant AKIII gene obtained in Example 2 was allowed to co-exist with the mutant DDPS gene. The mutant AKIII gene to co-exist with the mutant DDPS gene was selected as originating from the No. 80 strain (lysC*80), judging from the enzyme activity, heat stability and the like.

lysC*80 was used after excising it from a plasmid pLLC*80 (FIG. 8) prepared by alternatively ligating lysC* having existed on pLYSC1*80 (hereinafter referred to as "lysC*80") at the downstream of a lacZ promoter of vector pHSG399 (produced by Takara Shuzo Co., Ltd.) which has an inverted-directional-insertion site with respect to pUC18 in order to increase the expression amount of lysC*. pLLC*80 is a plasmid prepared to arrange lysC*80 to allow the direction of transcription to have a normal orientation with respect to the lacZ promoter in order to improve the productivity of L-lysine because lysC*80 on pLYSC1*80 has its direction of transcription arranged in a reversed orientation with respect to the lacZ promoter.

Figure 9:
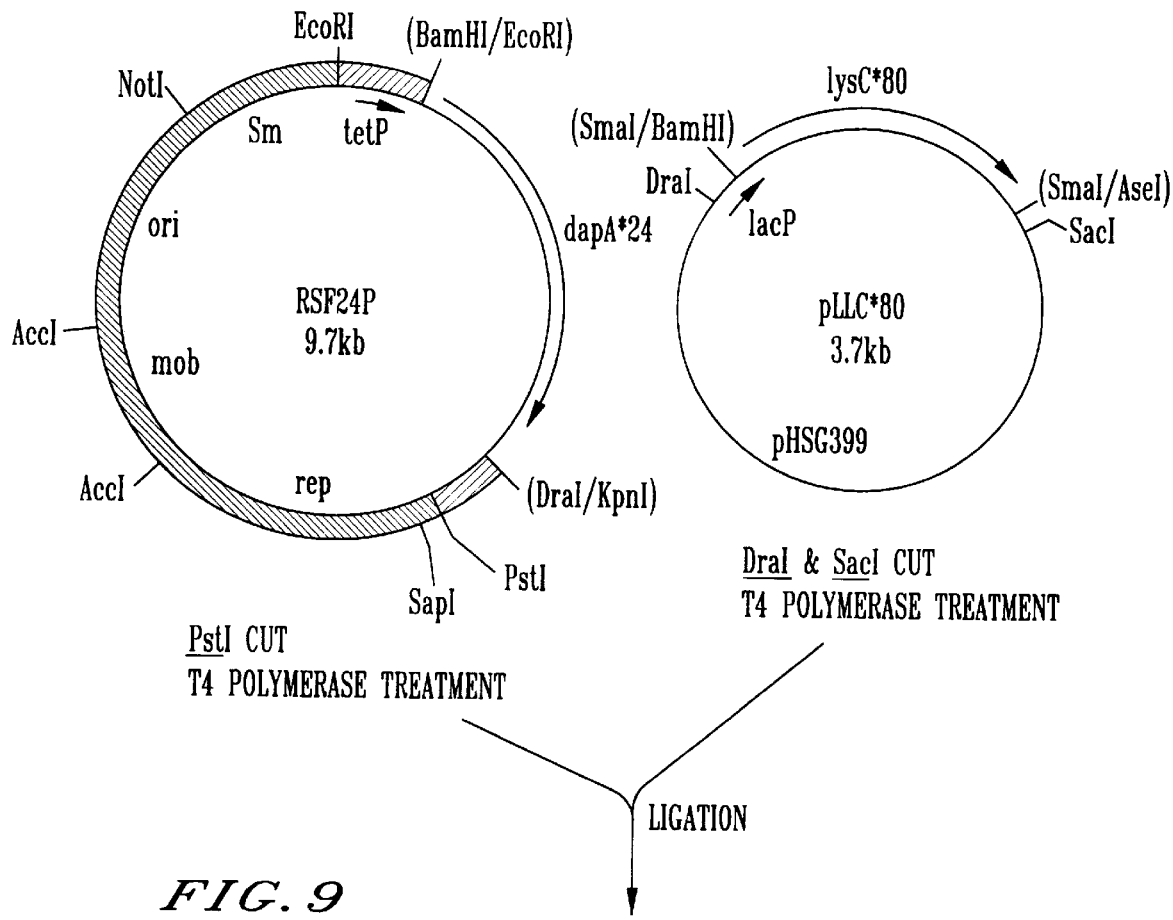
FIG. 9 shows preparation steps for a plasmid RSFD80 originating from RSF1010 having dapA*24 and lysC*80.
Figure 9:
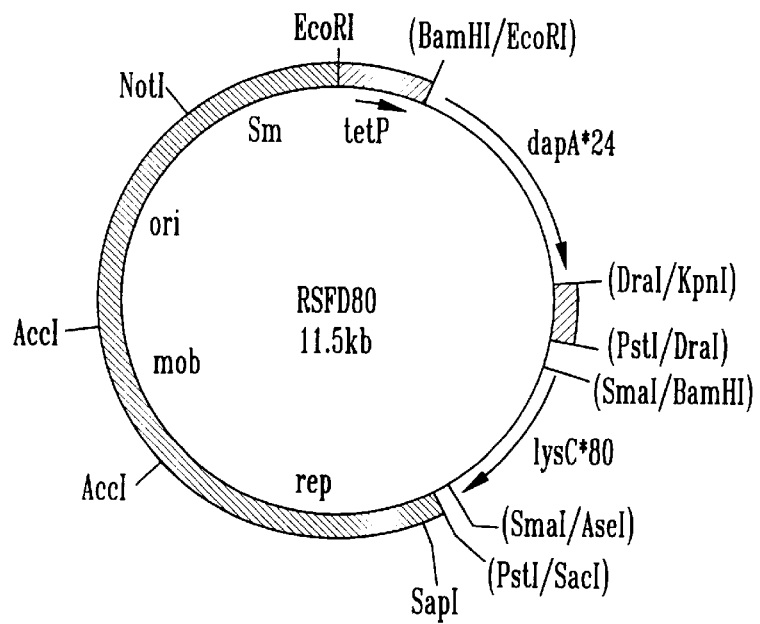

A plasmid, RSFD80, having dapA* and lysC* was prepared from pLLC*80 and RSF24P obtained in Example 3 as shown in FIG. 9. RSFD80 includes dapA*24 and lysC*80 arranged in this order to allow the direction of transcription to have a normal orientation with respect to tetP at the downstream from a promoter (tetp) of a tetracycline resistance gene.

The RSFD80 µplasmid was introduced into an *E. coli* JM109 strain, which was designated as AJ12396. AJ12396 is deposited in National Institute of Bioscience and Human Technology of Agency of Industrial Science and Technology on Oct. 28, 1993, as accession number of FERM P-13936, and transferred from the original deposition to international deposition based on Budapest Treaty on Nov. 1, 1994, and has been deposited as accession number of FERM BP-4859.

Strains harboring pLYSC1*24, pLYSC1*43, pLYSC1*48, pLYSC1*60, pLYSC1*117, pLYSC1*126, pLYSC1*149, pLYSC1*150, pLYSC1*156, pLYSC1*158, pLYSC1*167, pLYSC1*169 and pLYSC1*172 were not deposited. However, all of the mutation points of lysC* on each of the plasmids have been clarified as described above. Thus it is easy for those skilled in the art that the plasmid is recovered from the aforementioned deposited bacterium by using a method of Maniatis et al. (Sambrook, J., Fritsch, E. F., Maniatis, T., *Molecular Cloning*, Cold Spring Harbor Laboratory Press, 1.21 (1989)), and a target gene is obtained by using a site-directed mutagenesis method (Sambrook, J., Fritsch, E. F., Maniatis, T., *Molecular Cloning*, Cold Spring Harbor Laboratory Press, 15.63 (1989)). RSFD80 was introduced into B-399 strain in accordance with an ordinary method, and B-399/RSFD80 was obtained. The L-lysine productivity of B-399/RSFD80 was evaluated. The L-lysine productivity was also evaluated for B-399/RSFP as a control.

The cultivation was performed at an agitation of 114–116 rpm under a condition of a cultivation period of 48 hours and a temperature of 37° C. by using the same medium for production of L-lysine as in Example 3. Results are shown in Table 6.

TABLE 6

| Bacterial strain | Production amount of L-lysine hydrochloride |
|---|---|
| B-399/RSFD80 | 9.2 g/L |
| B-399/RSFP | 0 g/L |

EXAMPLE 5
Fermentation Production of L-lysine with Strain Being Introduced dapA* and lysC* (II)

It has been confirmed in Example 4 that the productivity of L-lysine can be improved by allowing the bacterium belonging to the genus Escherichia to harbor the mutant dapA gene and the mutant lysC gene. Experiments were performed to confirm whether or not this effect was maintained when the host is changed.

An *E. coli* W3110(tyrA) strain was used as a host. The W3110(tyrA) strain is described in detail in European Patent Publication No. 488424/92. Its preparation method will be briefly described as follows. The *E. coli* W3110 strain was obtained from National Institute of Genetics (Mishima-shi, Shizuoka-ken, Japan). This strain was spread on an LB plate containing streptomycin, and a streptomycin resistant strain was obtained by selecting strains which formed colonies. The selected streptomycin resistant strain was mixed with an *E. coli* K-12 ME8424 strain, and stationarily cultivated in a complete medium (L-Broth: 1% Bacto trypton, 0.5% Yeast extract, 0.5% NaCl) under a condition of 37° C. for 15 minutes to induce conjugation. The *E. coli* K-12 ME8424 strain has genetic characters of (HfrPO$_{45}$, thi, relA1, tyrA::Tn10, ung-1, nadB), which is available from National Institute of Genetics.

The culture was then spread on a complete medium (L-Broth: 1% Bacto trypton, 0.5% Yeast extract, 0.5% NaCl, 1.5% agar) containing streptomycin, tetracycline and L-tyrosine, and a colony-forming strain was selected. This strain was designated as *E. coli* W3110(tyrA) strain.

By the way, European Patent Publication No. 488424/92 describes many strains formed by introducing plasmids into the W3110(tyrA) strain. For example, a strain obtained by introducing a plasmid pHATerm is designated as *E. coli* W3110(tyrA)/pHATerm strain, and deposited in National Institute of Bioscience and Human Technology of Agency of Industrial Science and Technology, to which a registration No. of FERM BP-3653 is given. The W3110(tyrA) strain can be also obtained by curing the plasmid pHATerm from the *E. coli* W3110(tyrA)/pHATerm strain. The curing of the plasmid can be performed in accordance with an ordinary method.

The plasmid RSFD80 containing both of dapA* and lysc* obtained in Example 4 was introduced into the W3110(tyrA) obtained as described above, and W3110(tyrA)/RSFD80 was obtained. The L-lysine productivity was evaluated for W3110(tyrA)/RSFD80. As a control, RSFP was introduced into the W3110(tyrA) strain in accordance with an ordinary method, and W3110(tyrA)/RSFP was obtained. The L-lysine productivity was also evaluated for W3110(tyrA)/RSFP as a control.

The cultivation was performed at an agitation of 114–116 rpm under a condition of a cultivation period of 48 hours and a temperature of 37° C. by using the aforementioned medium for L-lysine production. Results are shown in Table 7.

TABLE 7

| Bacterial strain | Production amount of L-lysine hydrochloride |
|---|---|
| W3110 (tyrA) /RSFD80 | 8.9 g/L |
| W3110 (tyrA) /RSFP | 0 g/L |

EXAMPLE 6
Analysis of Rate Determining Steps of L-lysine Biosynthesis System and Improvement in L-lysine Productivity of L-lysine-producing Bacteria Belonging to the Genus Escherichia It was tried to improve the L-lysine productivity by analyzing rate determining steps of the L-lysine biosynthesis system of *E. coli* and enhancing genes for enzymes which catalyze the steps.

<1> Identification of the First Rate Determining Steps
(6-1-1) Preparation of Genes of L-lysine Biosynthesis System The rate determining step was identified by isolating various genes of the L-lysine biosynthesis system, introducing these genes into *E. coli*, and examining effects of each of the genes on the L-lysine productivity. The introduced genes for enzymes of the L-lysine biosynthesis system, and the enzymes encoded by them are as follows.

ppc: phosphoenolpyruvate carboxylase aspc: aspartate aminotransferase lysC: aspartokinase III lysC*80: inhibition-desensitized aspartokinase III asd: aspartate semialdehyde dehydrogenase dapA: dihydrodipicolinate synthase dapA*24: inhibition-desensitized dihydrodipicolinate synthase dapB: dihydrodipicolinate reductase DDH: diaminopimelate dehydrogenase (originating from *Brevibacterium lactofermentum*)

lysA: diaminopimelate decarboxylase

The L-lysine biosynthesis system from phosphoenolpyruvic acid to L-lysine can be thoroughly covered by the genes described above. The dapc, dapD, dapE and dapF genes, among the genes of the L-lysine biosynthesis system originally possessed by E. coli, are replaced with the gene DDH coding for DDH (diaminopimelate dehydrogenase) of Brevibacterium lactofermentum which can catalyze reactions concerning these gene products by itself. The W3110(tyrA) strain of the E. coli K-12 series was used as a host for introducing these genes.

Figure 10:
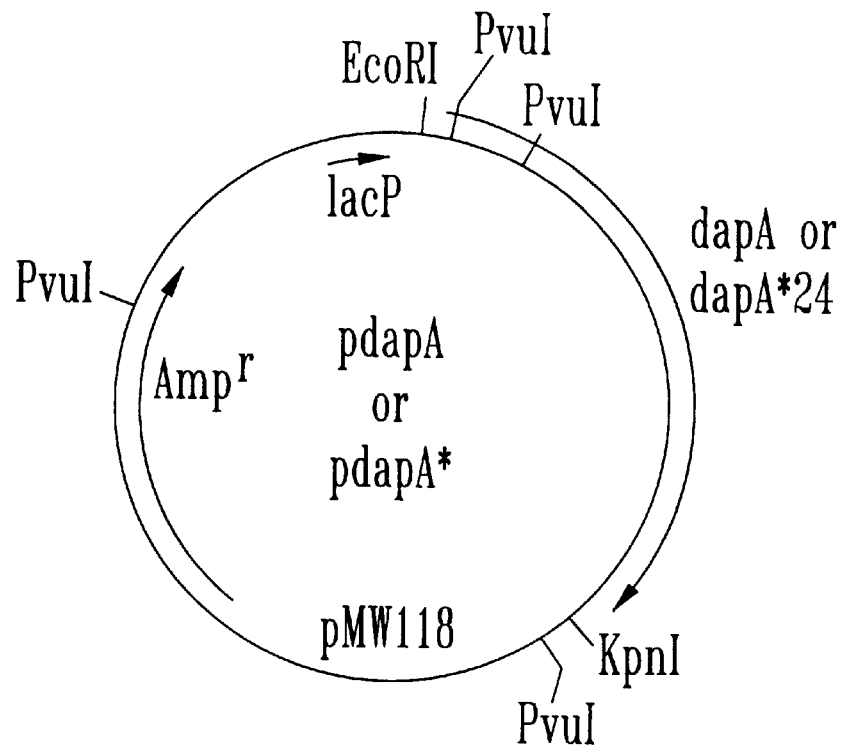
FIG. 10 shows structures of plasmids pdapA and pdapA* having dapA or dapA*.
Figure 11:
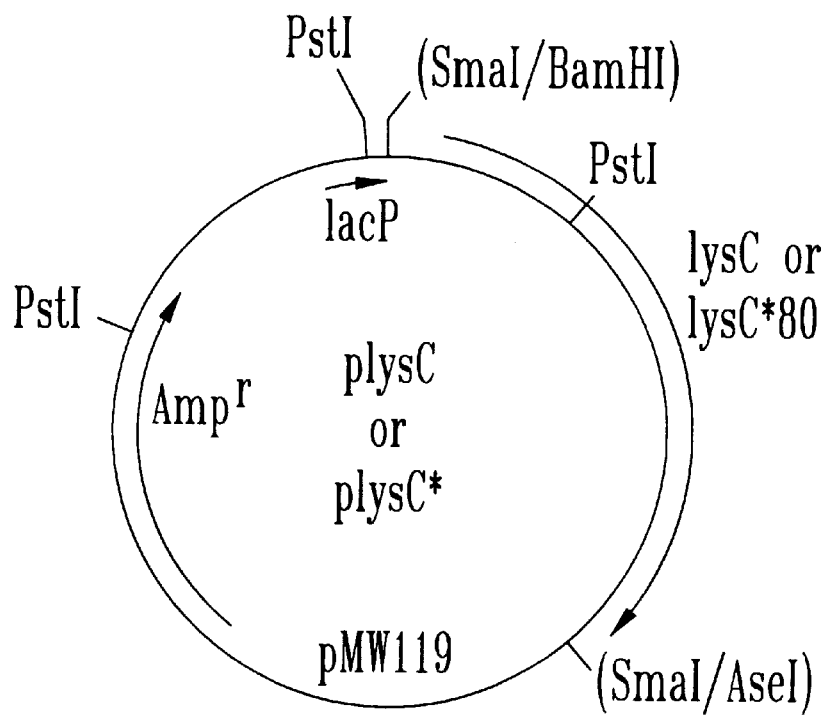
FIG. 11 shows structures of plasmids plysC and plysC* having lysC or lysC*80.

The dapA and dapA*24 genes were respectively obtained by excision from pdapA2 and pdapAS24 (see Example 1) with EcoRI and KpnI (FIG. 10). These genes were ligated with pMW118 which was digested with EcoRI and KpnI to obtain pdapA and pdapA*. The lysC and lysC*80 genes were respectively obtained by excision from pLYSC1 and pLLC*80 (see Example 2) with EcoRI and SphI. These genes were ligated with pMW119 which was digested with EcoRI and SphI to obtain plysc and plysC* (FIG. 11).

Figure 12:
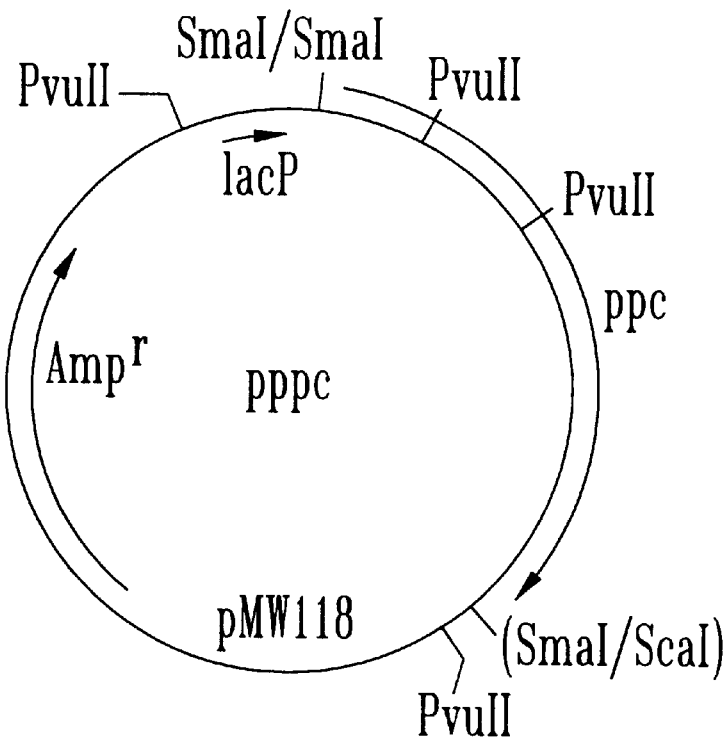
FIG. 12 shows a structure of a plasmid pppc having ppc.

The ppc gene was obtained from a plasmid pT2 having this gene. pT2 was cut with SmaI and ScaI, and the termini were blunt-ended, followed by insertion into a SmaI site of pMW118 to obtain a plasmid pppc (FIG. 12). E. coli F15 (AJ12873) harboring pT2 is deposited in National Institute of Bioscience and Human Technology of Agency of Industrial Science and Technology under an accession number of FERM BP-4732.

Figure 13:
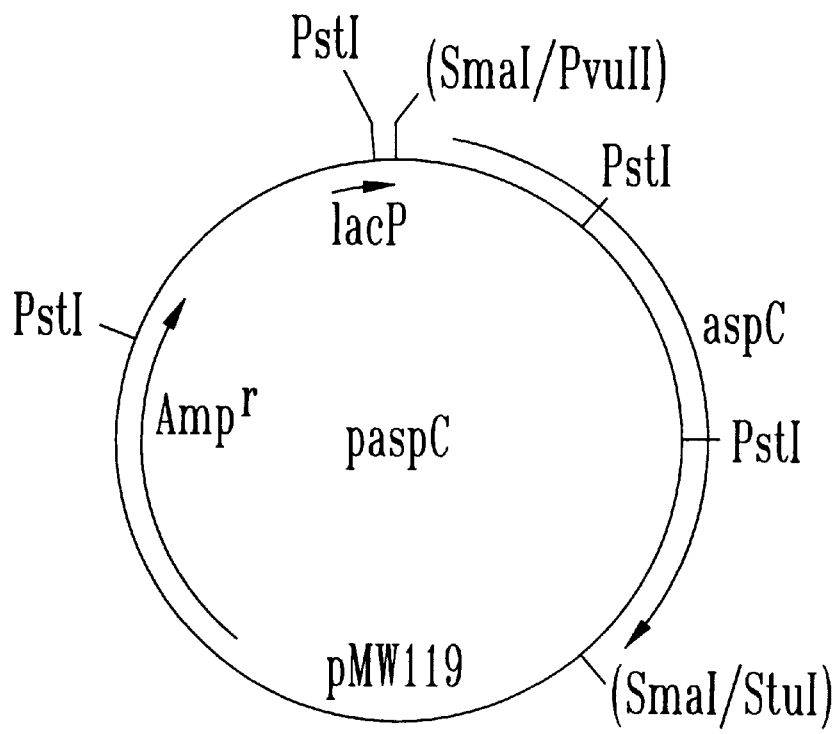
FIG. 13 shows a structure of a plasmid paspc having aspc.

The aspC gene was obtained from a plasmid pLF4 (Inokuchi, K. et al., Nucleic Acids Res., 10, 6957 (1982)) having this gene (FIG. 13). pLF4 was cut with PvuII and StuI, and the termini were blunt-ended, followed by insertion into a SmaI site of pMW119 to obtain a plasmid paspc.

Figure 14:
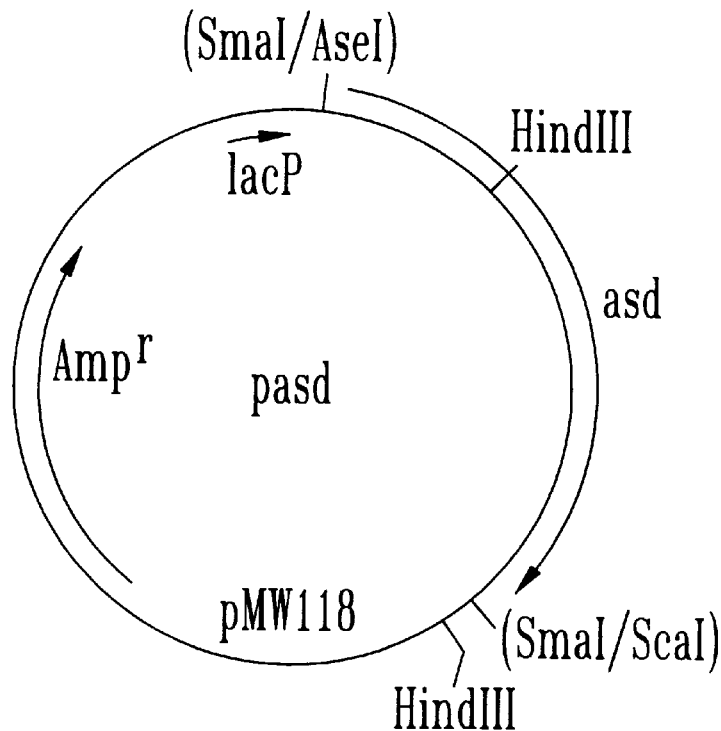
FIG. 14 shows a structure of a plasmid pasd having asd.

The asd gene was obtained from a plasmid pAD20 (Haziza, C. et al., EMBO, 1, 379 (1982)) having this gene. pAD20 was cut with AseI and ClaI, and the termini were blunt-ended, followed by insertion into a SmaI site of pMW118 to obtain a plasmid pasd (FIG. 14).

Figure 15:
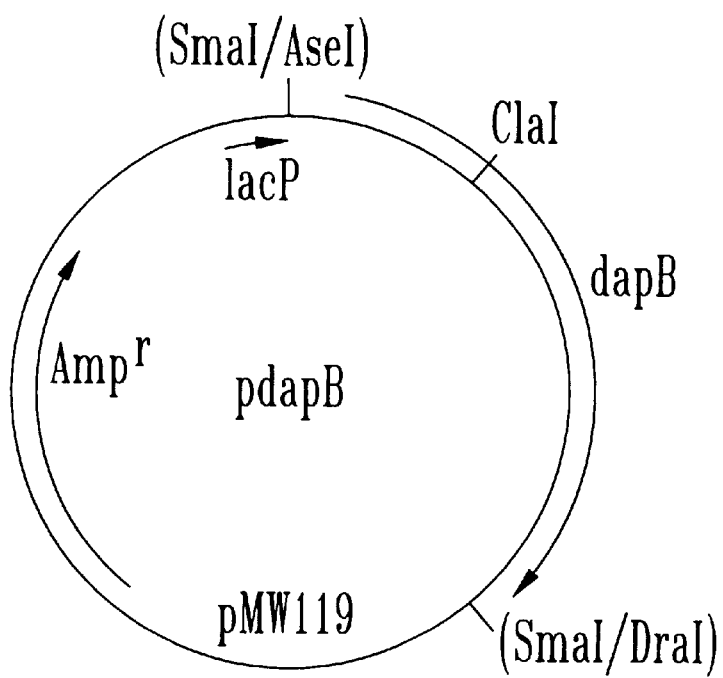
FIG. 15 shows a structure of a plasmid pdapB having dapB.

The dapB gene was obtained by amplifying a dapB gene from chromosomal DNA of an E. coli W3110 strain by means of the PCR method by using two species of oligonucleotide primers (SEQ ID NO:9, NO:10) prepared on the basis of a nucleotide sequence of a known dapB gene (Bouvier, J. et al., J. Biol. Chem., 259, 14829 (1984)) (FIG. 15). An obtained amplified DNA fragment was cut with AseI and DraI, and the termini were blunt-ended, followed by insertion into a SmaI site of pMW119 to obtain a plasmid pdapB.

Figure 16:
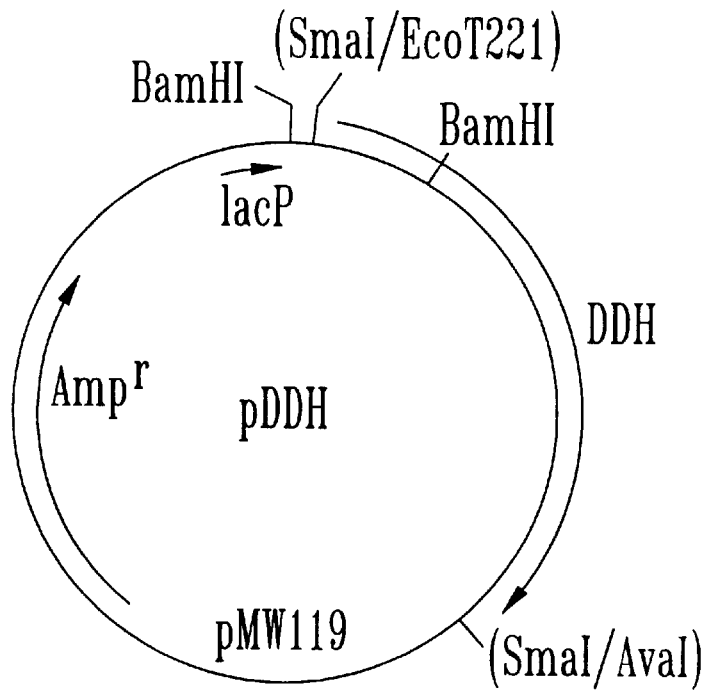
FIG. 16 shows a structure of a plasmid pDDH having DDH.

The DDH gene was obtained by amplifying a DDH gene from chromosomal DNA of Brevibacterium lactofermentum ATCC13869 by means of the PCR method by using two species of oligonucleotide primers (SEQ ID NO:11, NO:12) prepared on the basis of a known nucleotide sequence of a DDH gene of Corynebacterium glutamicum (Ishino, S. et al., Nucleic Acids Res., 15, 3917 (1987)). An obtained amplified DNA fragment was cut with EcoT22I and AvaI, and the termini were blunt-ended, followed by insertion into a SmaI site of pMW119 to obtain a plasmid pDDH (FIG. 16).

Figure 17:
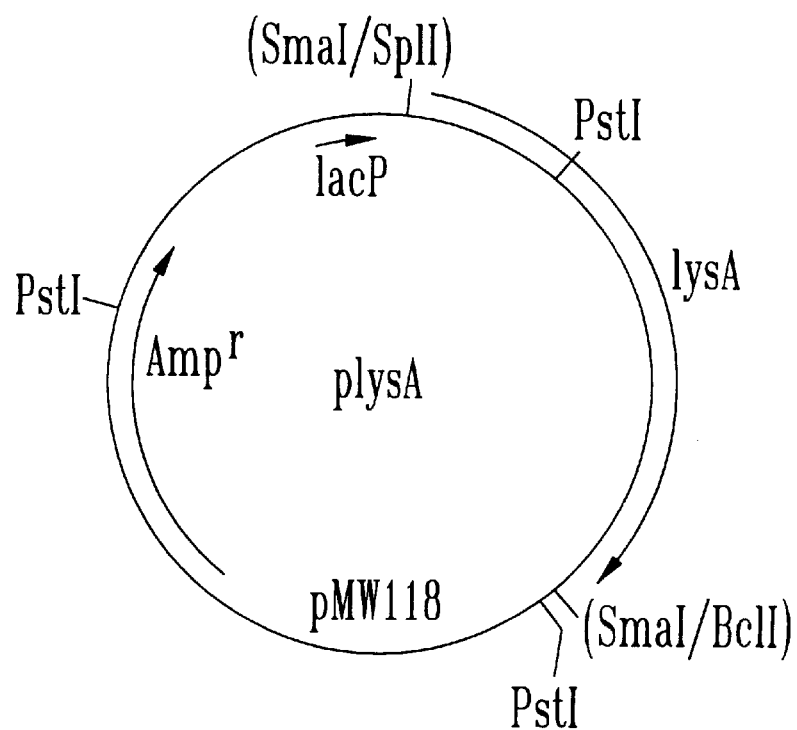
FIG. 17 shows a structure of a plasmid plysA having lysA.

The lysA gene was obtained by amplifying a lysA gene from chromosomal DNA of an E. coli W3110 strain by means of the PCR method by using two species of oligonucleotide primers (SEQ ID NO:13, NO:14) prepared on the basis of a nucleotide sequence of a known lysA gene (Stragier, P. et al., J. Mol. Biol., 168, 321 (1983)). An obtained amplified DNA fragment was cut with SpII and BclI, and the termini were blunt-ended, followed by insertion into a SmaI site of pMW118 to obtain a plasmid plysA (FIG. 17).

Confirmation of the fact that each of the aforementioned genes was cloned was performed by cutting them with restriction enzymes shown in the figures. The vectors pMW118 and pMW119 (produced by Nippon Gene) used for cloning of these genes were selected because they were able to co-exist in cells of E. coli together with RSF1010 as a vector used for preparation of plasmids for lysine production described below, and also had a stable distribution mechanism.

(6-1-2) L-lysine Productivity of E. coli with Introduced Genes of L-lysine Biosynthesis System E. coli W3110(tyrA) was transformed with each of the plasmids containing the genes of the L-lysine biosynthesis system described above, and obtained transformants were cultivated to perform L-lysine production. The cultivation was performed for 30 hours under a condition of a cultivation temperature of 37° C. and an agitation of 114–116 rpm by using the following medium. Results are shown in Table 8.

(Medium Composition)

| | |
|---|---|
| Glucose | 40 g/l |
| MgSO$_4$•7H$_2$O | 1 g/l |
| (NH$_4$)$_2$SO$_4$ | 16 g/l |
| KH$_2$PO$_4$ | 1 g/l |
| FeSO$_4$•7H$_2$O | 0.01 g/l |
| NnSO$_4$•5H$_2$O | 0.01 g/l |
| Yeast Ext. (Difco) | 2 g/l |
| L-tyrosine | 0.1 g/l |
| pH was adjusted to 7.0 with KOH to be autoclaved at 115° C. for 10 minutes (Glucose and MgSO$_4$.7H$_2$O were separately sterilized). | |
| Pharmacopoeial CaCO$_3$ | 25 g/l |
| (heat-sterilized in dry state at 180° C. for 2 days) | |
| Antibiotics | |
| (streptomycin 20 mg/l or ampicillin 50 mg/l depending on species of plasmids to be introduced) | |

TABLE 8

| Bacterial strain | Production amount of L-lysine hydrochloride (g/l) | Yield versus sugar (%) |
|---|---|---|
| W3110(tyrA) | 0.08 | 0.2 |
| W3110(tyrA)/pppc | 0.08 | 0.2 |
| W3110(tyrA)/paspC | 0.12 | 0.3 |
| W3110(tyrA)/plysC | 0.08 | 0.2 |
| W3110(tyrA)/plysC* | 2.27 | 5.57 |
| W3110(tyrA)/pasd | 0.12 | 0.3 |
| W3110(tyrA)/pdapA | 2.32 | 5.70 |
| W3110(tyrA)/pdapA* | 3.63 | 8.90 |
| W3110(tyrA)/pdapB | 0.08 | 0.2 |
| W3110(tyrA)/pDDH | 0.08 | 0.2 |
| W3110(tyrA)/plysA | 0.12 | 0.3 | i E. coliW3110(tyrA) became to produce L-lysine by introduction of plysC*, pdapA or pdapA*. Since both of lysC product and dapA product suffer feedback inhibition by L-lysine, it can be postulated that these enzymes are major regulatory points in L-lysine biosynthesis. The reaction catalyzed by dapA product exists in a position of branching to a biosynthesis system for L-threonine, L-methionine and L-isoleucine and a biosynthesis system for L-lysine, and is the first step of the biosynthesis system inherent to L-lysine. It was already reported that E. coli also becomes to produce L-lysine by amplification of a wild type dapA (Eur. J. Appl. Microbiol. Biotechnol., 15, 227 (1982)), which has been also confirmed from the result described above. On the other hand, the result of Example 3 has been confirmed again in that the yield of L-lysine is further increased when dapA* as an inhibition-desensitized type gene is introduced into E. coli.

Crude enzyme solutions were prepared from W3110 (tyrA), W3110(tyrA)/pdapA and W3110(tyrA)/pdapA* in the same manner as in Example 1, the DDPS (dihydrodipicolinate synthase) activity was measured, and the degree of inhibition of the DDPS activity by L-lysine was examined. Results are shown in Table 9.

TABLE 9

| Bacterial strain | Specific activity *1 | Degree of desensitization of inhibition *2 |
| --- | --- | --- |
| W3110(tyrA) | 0.0423 | 50 |
| W3110(tyrA)/pdapA | 0.2754 | 22.9 |
| W3110(tyrA)/pdapA* | 0.1440 | 76.5 |

*1: μmols/min/mg protein
*2: ratio of activity maintenance (%) in the presence of 5 mM of L-lysine The inhibition-desensitized dapA* product probably has a large effect on L-lysine production because it has a high degree of desensitization of inhibition although it has a lower specific activity than the wild type enzyme (about ½). The necessity of the desensitization of inhibition of the dapA product has been shown for L-lysine production.

In addition, the fact that lysc* has an effect on L-lysine production can be considered as follows. The first rate determining step is a step at which HD (homoserine dehydrogenase: product of thrA or metLM) competes with DDPS (dapA product) in acquiring ASA (aspartate-β-semialdehyde) as a substrate to serve at a branching point of the biosynthesis system, and when dapA is enhanced as described above, the reaction flows in a direction of L-lysine biosynthesis. On the other hand, it is speculated that when the supply amount of ASA is increased by enhancing lysc which participates in a reaction further upstream from dapA, any of reactions relevant to HD and DDPS is also facilitated, and thus the production amount of L-lysine has been also increased. However, this effect is scarcely obtained by enhancement of the wild type lysC only. This is probably because the inhibition of the wild type AKIII (lysC product) by L-lysine is more strict than that of the wild type DDPS (AKIII and DDPS are inhibited by about 100% and 80% respectively in the presence of 5 mM of L-lysine).

According to the facts described above, it was judged that the reaction by DDPS having a higher lysine-producing effect was the first rate determining step, and it was postulated that the reaction by AKIII was the second rate determining step.

<2> Identification of the Second Rate Determining Step

The second rate determining step was identified by enhancing various genes of the L-lysine biosynthesis system in strains with introduced dapA*. In order that other plasmids were stably harbored when they were introduced into E. coli harboring a plasmid containing dapA*, dapA* was transferred from pdapA to RSF1010, and RSF24P was obtained (FIG. 7). E. coli W3110(tyrA) was transformed with the plasmid RSF24P having dapA*.

Plasmids having genes of the L-lysine biosynthesis system were introduced into E. coli W3110(tyrA)/RSF24P. Two species of plasmids, namely RSF24P and a plasmid containing another gene of the L-lysine biosynthesis system, co-exist in each of obtained transformants. The L-lysine productivity was examined for these strains in the same manner as in (6-1-2). Results are shown in Table 10.

TABLE 10

| Bacterial strain | Production amount of L-lysine hydrochloride (g/l) | Yield versus sugar (%) |
| --- | --- | --- |
| W3110(tyrA)/RSF24P | 3.63 | 8.9 |
| W3110(tyrA)/RSF24P + pppc | 3.67 | 9.0 |
| W3110(tyrA)/RSF24P + paspC | 3.59 | 8.8 |
| W3110(tyrA)/RSF24P + plysC | 3.42 | 8.4 |
| W3110(tyrA)/RSF24P + plysC* | 9.17 | 22.5 |
| W3110(tyrA)/RSF24P + pasd | 3.75 | 9.2 |
| W3110(tyrA)/RSF24P + pdapA | 3.55 | 8.7 |
| W3110(tyrA)/RSF24P + pdapA* | 3.46 | 8.5 |
| W3110(tyrA)/RSF24P + pdapB | 4.08 | 10.0 |
| W3110(tyrA)/RSF24P + pDDH | 3.67 | 9.0 |
| W3110(tyrA)/RSF24P + plysA | 3.55 | 8.7 |

As a result, a remarkable enhancing effect on the L-lysine productivity was found only in lysC*. The wild type lysC had no effect at all. This is probably because the inhibition by L-lysine is strong as described above. Thus it was confirmed that the reaction participated by lysC* was the second rate determining step.

lysc* was integrated into RSF24P, and RSFD80 was obtained (FIG. 9). In the same manner, lysC was integrated into RSF24P, and an obtained plasmid was designated as RSFD1. These plasmids were introduced into E. coli W3110 (tyrA), crude enzyme solutions were prepared, and the AK activity and the degree of inhibition of AK activity by L-lysine were examined in the same manner as in (6-1-2). Results are shown in Table 11.

TABLE 11

| Bacterial strain for AK activity | Specific activity *1 | Degree of desensitization of inhibition *2 |
| --- | --- | --- |
| W3110(tyrA)/RSF24P | 0.94 | 42.9 |
| W3110(tyrA)/RSFD1 | 18.55 | 7.2 |
| W3110(tyrA)/RSFD80 | 33.36 | 98.8 |

*1: nmols/min/mg protein
*2: ratio of activity maintenance (%) in the presence of 5 mM of L-lysine The specific activities of AK of the strains harboring the plasmids were increased 20–30 times by integrating lysC and lysC* into RSF24P. E. coli has three species of AK's, and lysC codes for AKIII among them. However, a total activity of the three species of AK's was measured in the experiment described above. It is speculated that the inhibition by L-lysine also becomes high in the strain harboring RSFD1 with the inserted wild type lysc because the ratio occupied by AKIII is higher than those by AKI and AKIII as compared with the control (W3110(tyrA)/RSF24P), resulting in no indication of the effect on enhancement of the L-lysine productivity. On the other hand, it was revealed that the inhibition was desensitized for about 100% of AKIII in the strain harboring RSFD80, and this fact contributed to the improvement in L-lysine production.

<3> Identification of the Third Rate Determining Step

Next, various plasmids of the L-lysine biosynthesis system were introduced into E. coli W3110(tyrA)/RSFD80, and cultivation for L-lysine production was performed. Cultivation results are shown in Table 12.

TABLE 12

| Bacterial strain | Production amount of L-lysine hydrochloride (g/l) | Yield versus sugar (%) |
|---|---|---|
| W3110(tyrA)/RSFD80 | 9.17 | 22.5 |
| W3110(tyrA)/RSFD80 + pppc | 8.97 | 22.0 |
| W3110(tyrA)/RSFD80 + paspC | 9.05 | 22.2 |
| W3110(tyrA)/RSFD80 + plysC | 8.56 | 21.0 |
| W3110(tyrA)/RSFD80 + plysC* | 8.15 | 20.0 |
| W3110(tyrA)/RSFD80 + pasd | 8.35 | 20.5 |
| W3110(tyrA)/RSFD80 + pdapA | 8.56 | 21.0 |
| W3110(tyrA)/RSFD80 + pdapA* | 8.15 | 20.0 |
| W3110(tyrA)/RSFD80 + pdapB | 10.80 | 26.5 |
| W3110(tyrA)/RSFD80 + pDDH | 8.56 | 21.0 |
| W3110(tyrA)/RSFD80 + plysA | 8.48 | 20.8 |

Figure 18:
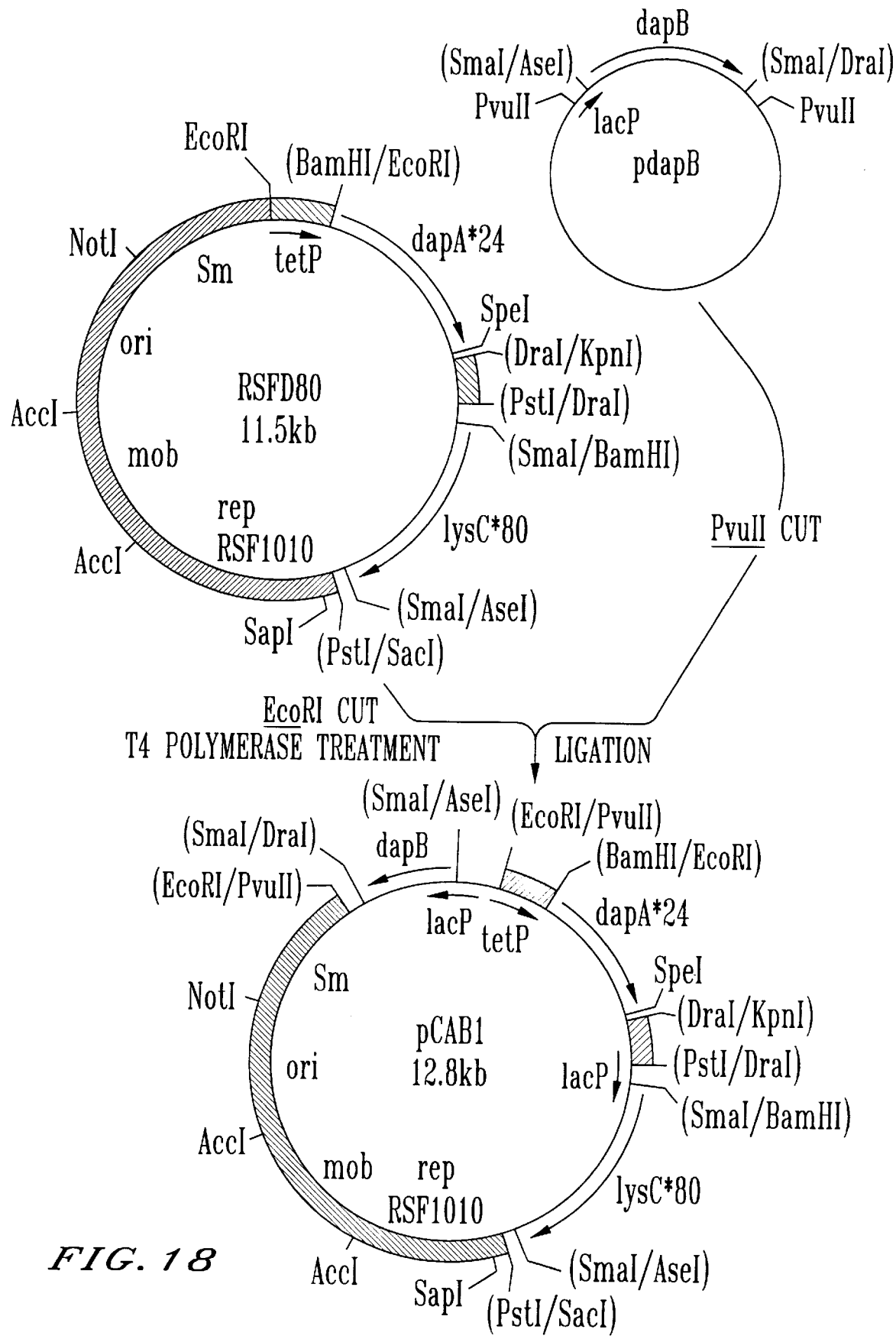
FIG. 18 shows preparation steps for a plasmid pCAB1 originating from RSF1010 having dapA*24, lysC*80 and dapB.

An enhancing effect on the L-lysine productivity was observed only in dapB, and it was found that the reaction participated by dapB was the third rate determining step. Thus dapB was inserted into RSFD80, and pCAB1 was obtained (FIG. 18). This plasmid was introduced into *E. coli* W3110(tyrA), a crude enzyme solution was prepared, and the enzyme activity of DDPR (dihydrodipicolinate reductase) was measured in accordance with a method described by Tamir, H. and Gilvarg, C., *J. Biol. Chem.,* 249, 3034 (1974). In the same manner, crude enzyme solutions were prepared from a strain harboring only RSFD80 and a strain harboring both RSFD80 and pdapB, and the DDPR activity was measured. Results are shown in Table 13.

TABLE 13

| Bacterial strain | Specific activity (μmols/min/mg protein) |
|---|---|
| W3110(tyrA)/RSFD80 | 0.027 |
| W3110(tyrA)/RSFD80 + pdapB | 0.092 |
| W3110(tyrA)/PCAB1 | 0.178 |

The DDPR activity was increased about 3 times in the strain harboring RSFD80 and pdapB, and it was increased about 6.5 times in the strain harboring pCAB1 in which dapB was inserted into RSFD80, as compared with the control (strain harboring RSFD80 only). According to the fact that both W3110(tyrA)/RSFD80+pdapB and W3110(tyrA)/pCAB1 had equivalent L-lysine accumulation of 10.8 g/l, it was judged that dapB was provided in a sufficient amount for L-lysine production, and the rate determining step was shifted to the next step.

<4> Identification of the Fourth Rate Determining Step

Next, the fourth rate determining step was identified by using the plasmid pCAB1 harboring lysc*, dapA* and dapB. Various plasmids of the L-lysine biosynthesis system were introduced into *E. coli* W3110(tyrA)/pCAB1, and cultivation for L-lysine production was performed. Cultivation results are shown in Table 14.

TABLE 14

| Bacterial strain | Production amount of L-lysine hydrochloride (g/l) | Yield versus sugar (%) |
|---|---|---|
| W3110(tyrA)/pCAB1 | 10.80 | 26.5 |
| W3110(tyrA)/pCAB1 + pppc | 11.00 | 27.0 |
| W3110(tyrA)/pCAB1 + paspC | 10.88 | 26.7 |
| W3110(tyrA)/pCAB1 + plysC | 10.60 | 26.0 |
| W3110(tyrA)/pCAB1 + plysC* | 10.39 | 25.5 |
| W3110(tyrA)/pCAB1 + pasd | 10.19 | 25.0 |
| W3110(tyrA)/pCAB1 + pdapA | 10.72 | 26.3 |
| W3110(tyrA)/pCAB1 + pdapA* | 10.80 | 26.5 |
| W3110(tyrA)/pCAB1 + pdapB | 10.92 | 26.8 |
| W3110(tyrA)/pCAB1 + pDDH | 12.23 | 30.0 |
| W3110(tyrA)/pCAB1 + plysA | 10.60 | 26.0 |

Figure 19:
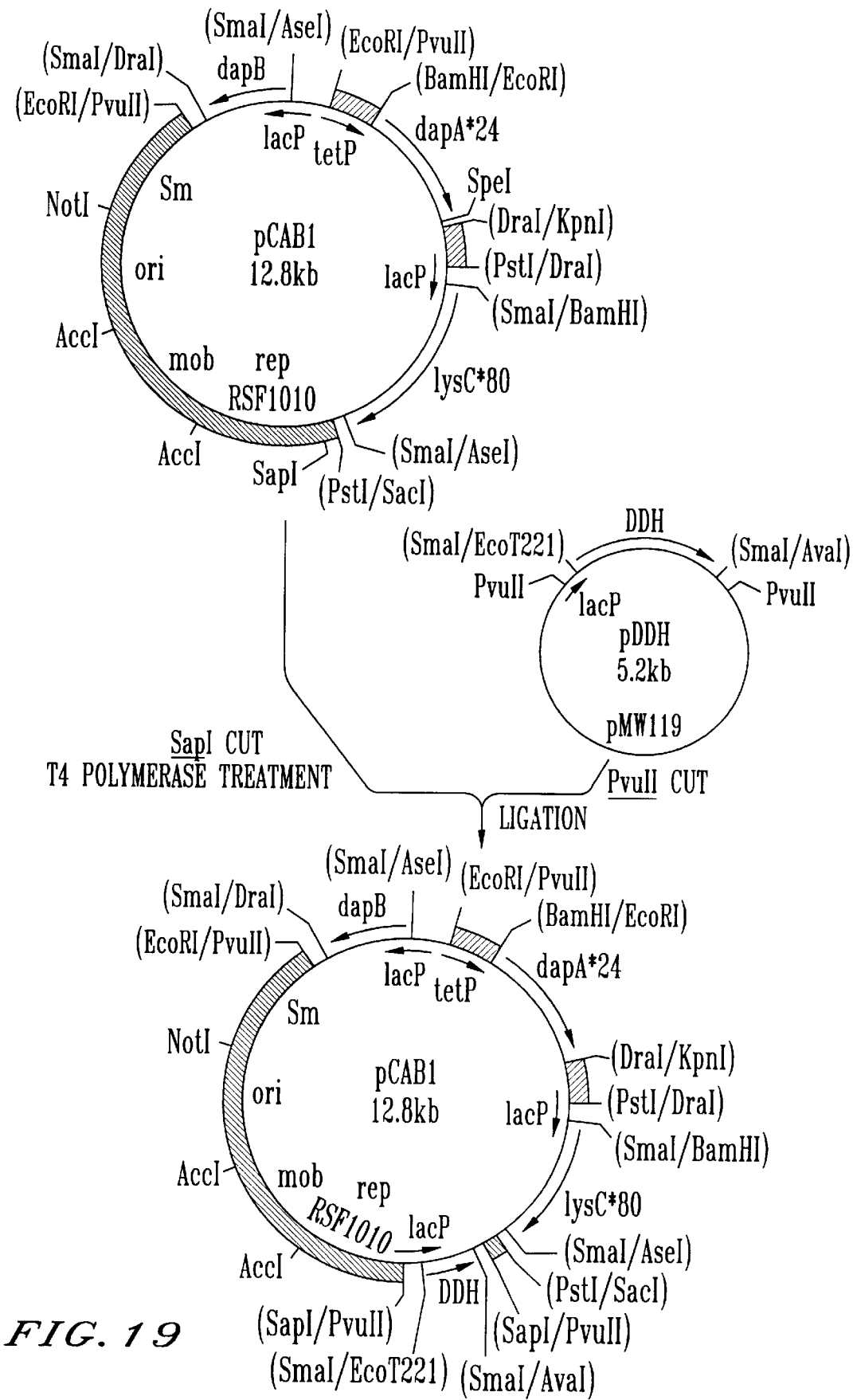
FIG. 19 shows preparation steps for a plasmid pCABD2 originating from RSF1010 having dapA*24, lysC*80, dapB and DDH.

An enhancing effect on the L-lysine productivity was observed only in DDH, and it was found that the reaction catalyzed by DDH was the fourth rate determining step. In addition, SDAP (N-succinyl-L,L-α, ε-diaminopimelic acid) detected in a culture broth of the DDH non-introduced strain was not detected in a culture broth of the DDH introduced strain. Detection of SDAP was performed by means of TLC development (composition of development solvent; methanol:water:10N HCl:pyridine =80:17.5:2.5:10) (Bouvier, J., Richaud, C., Higgins, W., Bogler, O. and Stragier, P., *J. Bacteriol.,* 174, 5265 (1992)). Further, the color of broth was brown in the case of the DDH non-introduced strain, but it was changed to yellow in the case of the DDH introduced strain. Thus DDH was integrated into pCAB1 to prepared a plasmid pCABD2 (FIG. 19), and the DDH activity of *E. coli* W3110(tyrA) transformed with this plasmid was measured. The DDH enzyme activity was measured in accordance with a literature (Azizono, Haruo, *Fermentation and Industry,* 45, 964 (1987)). Results are shown in Table 15.

TABLE 15

| Bacterial strain | Specific activity (μmols/min/mg protein) |
|---|---|
| W3110(tyrA)/pCAB1 | 0.000 |
| W3110(tyrA)/pCAB1 + pDDH | 0.799 |
| W3110(tyrA)/pCABD2 | 2.214 |

The DDH activity was not detected in the control (W3110(tyrA)/pCAB1) because DDH was originally not present in *E. coli*. The specific activity of DDH of the strain harboring pCABD2 (W3110(tyrA)/pCABD2) was about 2.5 times that of the strain harboring pDDH (W3110(tyrA)/pCAB1+pDDH), however, the both strain had an equivalent L-lysine accumulation amount (12.23 g/l). Thus it was judged that the DDH expression amount of pCABD2 was a sufficient amount.

<5> Analysis of Rate Determining Steps Among dapC, dapD, dapE and dapF

Next, in order to examine a rate limiting order of dapC, dapD, dapE and dapF replaced by DDH in the analysis described above, at first these genes were cloned. dapc was not cloned because of no report on its base sequence, however, the remaining three species of genes were cloned in accordance with the PCR method.

Figure 20:
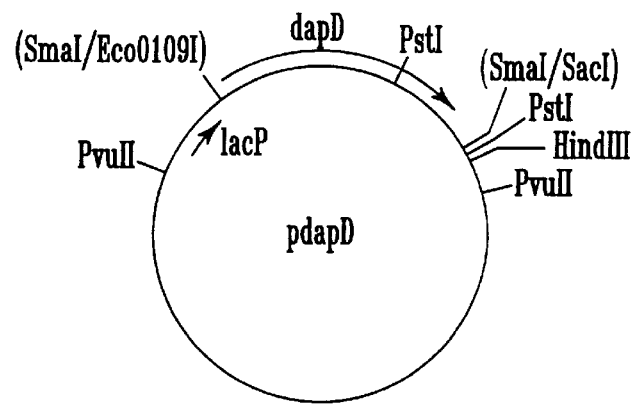
FIG. 20 shows a structure of a plasmid pdapD having dapD.

The dapD gene was obtained by amplifying a dapD gene from chromosomal DNA of an *E. coli* W3110 strain by means of the PCR method by using two species of oligo-nucleotide primers (SEQ ID NO:15, NO:16) prepared on the basis of a nucleotide sequence of a known dapD gene (Richaud, C. et al., *J. Biol. Chem.,* 259, 14824 (1984)). An obtained amplified DNA fragment was cut with Eco0109I and SacI, and the termini were blunt-ended, followed by insertion into a SmaI site of pMW118 to obtain a plasmid pdapD (FIG. 20).

Figure 21:
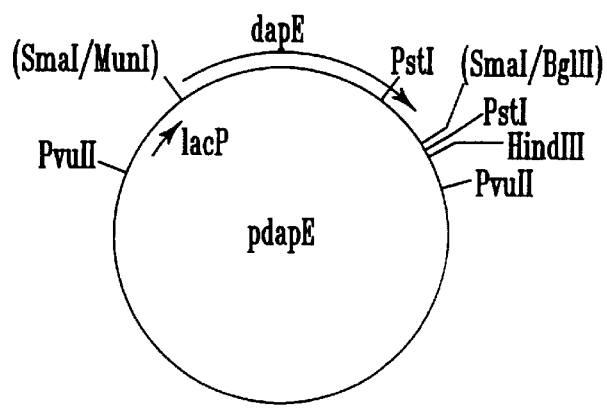
FIG. 21 shows a structure of a plasmid pdapE having dapE.

The dapE gene was obtained by amplifying a dapE gene from chromosomal DNA of an *E. coli* W3110 strain by means of the PCR method by using two species of oligonucleotide primers (SEQ ID NO:17, NO:18) prepared on the basis of a nucleotide sequence of a known dapE gene (Bouvier, J. et al., *J. Bacteriol.*, 174, 5265 (1992)). An obtained amplified DNA fragment was cut with MunI and BalII, and the termini were blunt-ended, followed by insertion into a SmaI site of pMW118 to obtain a plasmid pdapE (FIG. 21).

Figure 22:
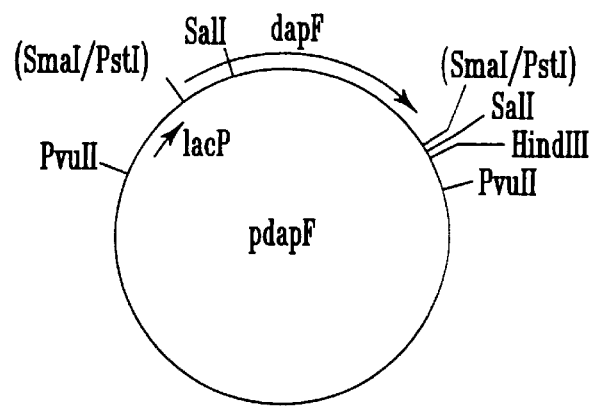
FIG. 22 shows a structure of a plasmid pdapF having dapF.

The dapF gene was obtained by amplifying a dapF gene from chromosomal DNA of an *E. coli* W3110 strain by means of the PCR method by using two species of oligonucleotide primers (SEQ ID NO:19, NO:20) prepared on the basis of a nucleotide sequence of a known dapF gene (Richaud, C. et al., *Nucleic Acids Res.*, 16, 10367 (1988)). An obtained amplified DNA fragment was cut with PstI, and the termini were blunt-ended, followed by insertion into a SmaI site of pMW118 to obtain a plasmid pdapF (FIG. 22).

Each of the plasmids obtained as described above was introduced into W3110(tyrA)/pCAB1, and cultivation for L-lysine production was performed. In the previous experiment, the changes were observed in the color of broth and in the presence or absence of accumulation of the intermediate (SDAP) in addition to the L-lysine production amount between before and after the introduction of DDH. Thus the analysis of the rate determining step was performed also by using them as indexes. Results are shown in Table 16.

TABLE 16

| Bacterial strain | Production amount of L-lysine hydrochloride (g/l) | Yield versus sugar (%) | Color of broth | Accumulation of SDAP |
|---|---|---|---|---|
| W3110(tyrA)/pCAB1 | 10.80 | 26.5 | brown | + |
| W3110(tyrA)/pCAB1 + pdapD | 11.08 | 27.2 | yellow | + |
| W3110(tyrA)/pCAB1 + pdapE | 11.12 | 27.3 | brown | – |
| W3110(tyrA)/pCAB1 + pdapF | 10.96 | 26.9 | brown | + |
| W3110(tyrA)/pCABD2 | 12.23 | 30.0 | yellow | – |

Figure 23:
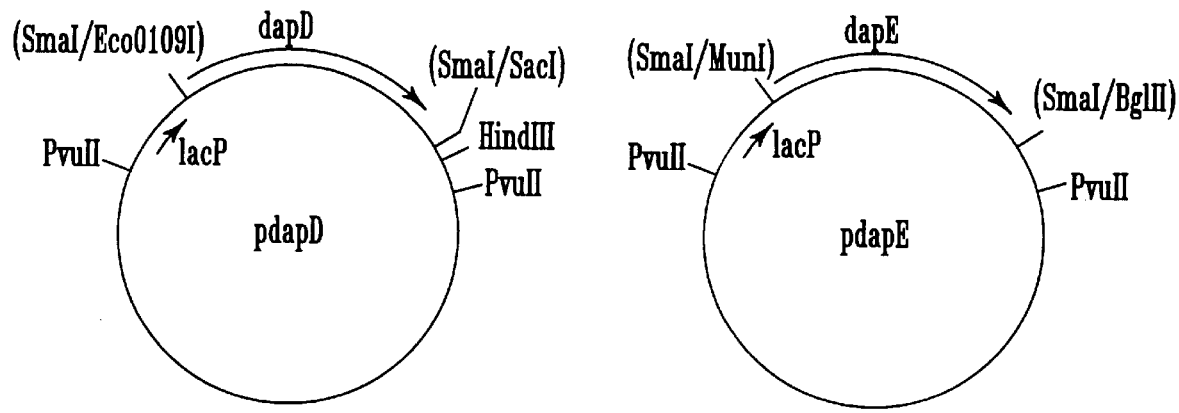
FIG. 23 shows preparation steps for a plasmid pMW-dapDE1 having dapD and dapE.
Figure 23:
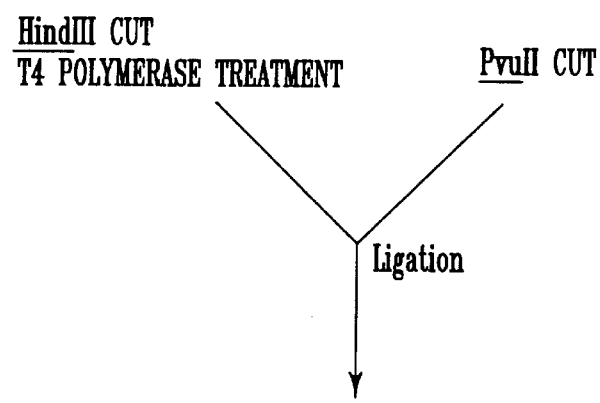
Figure 23:
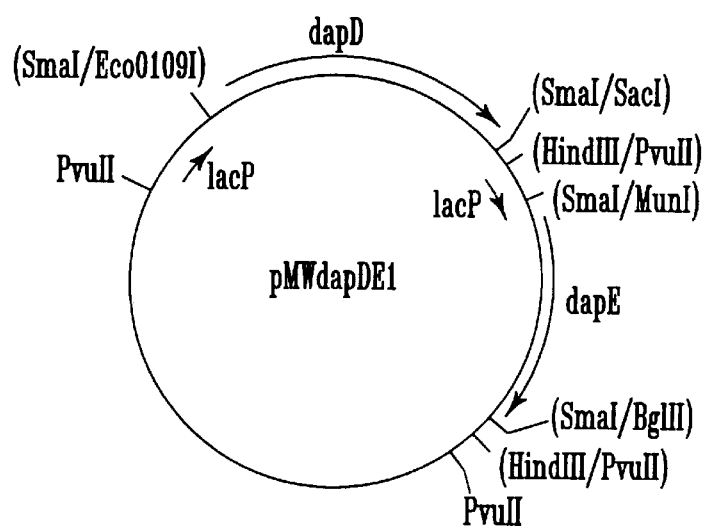
Figure 24:
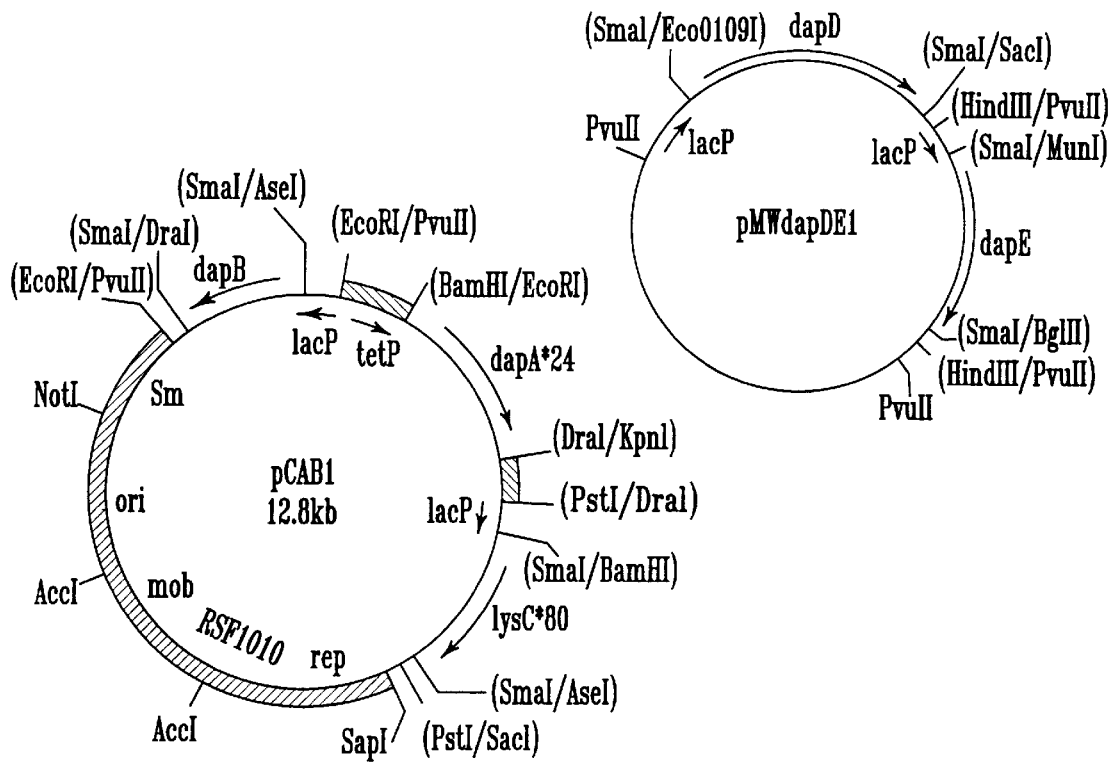
FIG. 24 shows preparation steps for a plasmid pCABDE1 having dapA*24, lysC*80, dapB, dapD and dapE.
Figure 24:
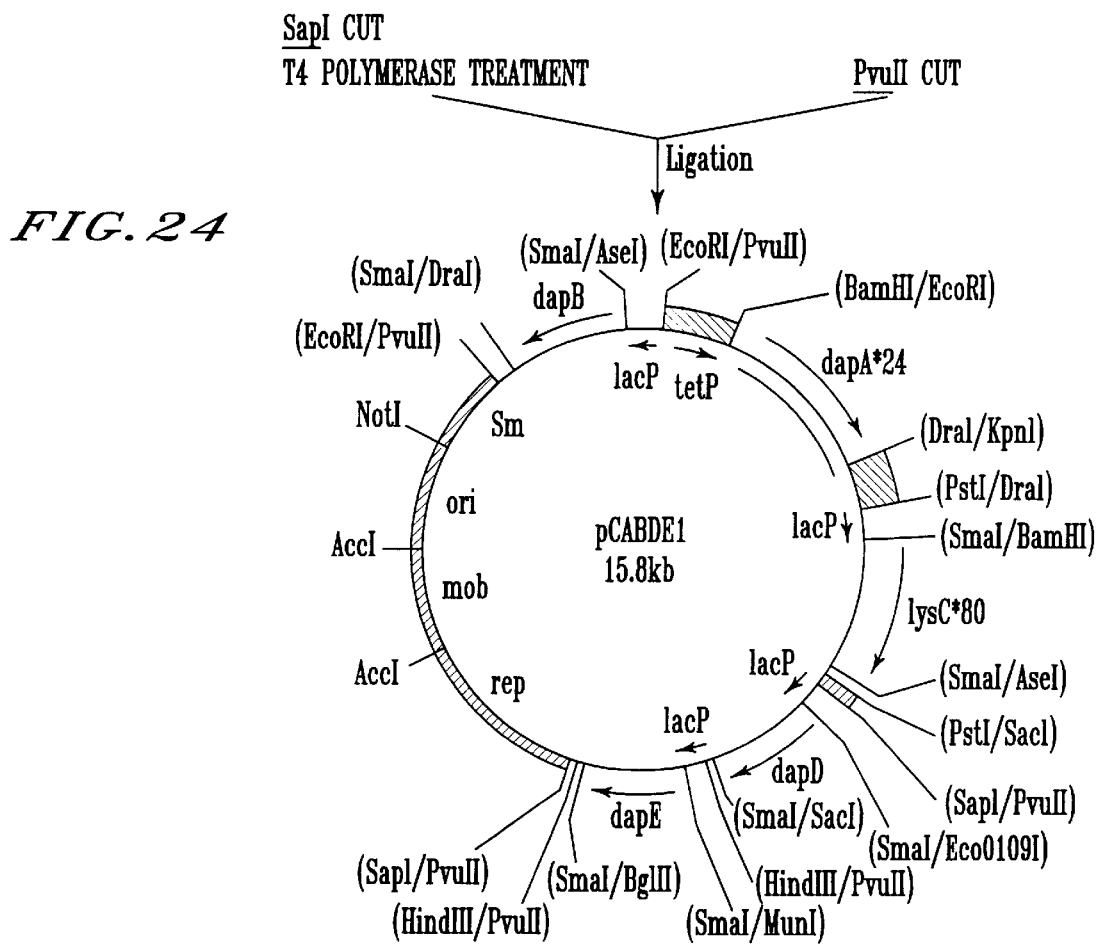

The production amount of L-lysine was increased a little by the enhancement of dapD or dapE, but DDH was not exceeded. Further, it was found that the change in color of broth and the accumulation of SDAP as an intermediate observed upon the introduction of DDH were independent phenomena with each other, the change in color of broth resulted from dapD, and the disappearance of SDAP resulted from dapE. The relation between dapE and SDAP may be postulated judging from the biosynthesis pathway of L-lysine. The enhancement of dapF had no effect on the improvement in L-lysine productivity.

dapE was excised from pdapE, and it was inserted into pdapD to prepare a plasmid pMWdapDE1 containing both dapE and dapD (FIG. 23). Further, a fragment containing dapE and dapD was excised from pMWdapDE1, and it was inserted into pCAB1 to prepare pCABDE1 (FIG. 24). Strains harboring pCAB1, pCABDE1 or pCABD2 and a strain harboring both pCABDE1 and pdapF were prepared, and cultivation for L-lysine production was performed by using these strains. Results are shown in FIG. 17.

TABLE 17

| Bacterial strain | Production amount of L-lysine hydrochloride (g/l) | Yield versus sugar (%) | Color of broth | Accumulation of SDAP |
|---|---|---|---|---|
| W3110(tyrA)/pCAB1 | 10.80 | 26.5 | brown | + |
| W3110(tyrA)/pCABDE1 | 12.23 | 30.0 | yellow | – |
| W3110(tyrA)/pCABDE1 + pdapF | 11.82 | 29.0 | yellow | – |
| W3110(tyrA)/pCABD2 | 12.23 | 30.0 | yellow | – |

It was found that the L-lysine production amount, the color of broth, and the presence or absence of accumulation of SDAP became equivalent to those in the case of the production of DDH by enhancing dapD and dapE in combination. In addition, it was found that further enhancement of dapF had no effect on the improvement in L-lysine productivity, and the reaction participated by dapF did not make rate limitation. The results described above can be interpreted as follows.

Upon the step of introduction of pCAB1, intermediates are accumulated at two steps of SKAP (N-succinyl-ε-keto-L-α-aminopimelic acid) and SDAP. Among these intermediates, SDAP was detected in an extracellular broth. Although SKAP was not detected, it was speculated to be accumulated in bacterial cells. The reason for such speculation resides in the color of broth. The color of broth is yellow in the case of the wild type strain (W3110(tyrA)) or the like producing no L-lysine. However, the broth becomes brown probably due to bacteriolysis or the like when a load is applied to growth. It is speculated that SDAP has a small load on growth because it is discharged to the outside of cells, and hence, the broth is improved to have a yellow color although the accumulation amount of SDAP increases when SKAP is metabolized by the enhancement of only dapD. However, even if dapD is enhanced, the accumulation amount of L-lysine does not increase unless rate limitation by further downstream dapE is desensitized.

<6> Conclusion

According to the results described above, it has been found that the L-lysine productivity is improved in a stepwise manner by performing (1) introduction of dapA*, (2) introduction of lysC*, (3) enhancement of dapB, and (4) enhancement of DDH or dapD and dapE in bacteria belonging to the genus Escherichia. Further, *E. coli*, in which the L-lysine productivity is improved in a stepwise manner, has been obtained.

<7> Analysis of Rate Determining Step of L-lysine Biosynthesis System in *E. coli* C Strain In order to examine whether or not the conclusion obtained in the foregoing could be applied to strains other than the *E. coli* K-12 series, rate determining steps of an L-lysine biosynthesis system of an *E. coli* C strain (IFO 13891) were analyzed in the same manner as described above. The cultivation condition was the same as that of W3110 (tyrA), however, L-tyrosine was not added to the medium.

(1) Identification of the First Rate Determining Step

The *E. coli* C strain (IFO 13891) transformed with plasmids containing genes of the L-lysine biosynthesis system was cultivated in the medium for L-lysine production, and the production amount of L-lysine hydrochloride was measured. Results are shown in Table 18.

TABLE 18

| Bacterial strain | Production amount of L-lysine hydrochloride (g/l) | Yields versus sugar (%) |
|---|---|---|
| C | 0.08 | 0.2 |
| C/pppc | 0.08 | 0.2 |
| C/paspC | 0.12 | 0.3 |
| C/plysC | 0.08 | 0.2 |
| C/plysC* | 0.12 | 0.3 |
| C/pasd | 0.08 | 0.2 |
| C/pdapA | 0.32 | 0.8 |
| C/pdapA* | 0.71 | 1.75 |
| C/pdapB | 0.12 | 0.3 |
| C/pDDH | 0.08 | 0.2 |
| C/plysA | 0.08 | 0.2 |

In the same manner as in W3110 (tyrA), L-lysine was also accumulated in the medium by the C strain by introducing the wild type dapA and further the inhibition-desensitized type dapA*. lysC* had no effect on the L-lysine productivity.

(2) Identification of the Second Rate Determining Step p The plasmid RSF24P containing dapA* was introduced into the E. coli C strain, and plasmids containing genes of the L-lysine biosynthesis system were further introduced. Obtained transformants were cultivated in the medium for L-lysine production, and the production amount of L-lysine hydrochloride was measured. Results are shown in Table 19.

TABLE 19

| Bacterial strain | Production amount of L-lysine hydrochloride (g/l) | Yield versus sugar (%) |
|---|---|---|
| C/RSF24P | 0.71 | 1.75 |
| C/RSF24P + pppc | 0.71 | 1.74 |
| C/RSF24P + paspC | 0.69 | 1.70 |
| C/RSF24P + plysC | 0.65 | 1.60 |
| C/RSF24P + plysC* | 1.82 | 4.50 |
| C/RSF24P + pasd | 0.70 | 1.73 |
| C/RSF24P + pdapA | 0.71 | 1.75 |
| C/RSF24P + pdapA* | 0.69 | 1.70 |
| C/RSF24P + pdapB | 0.99 | 2.45 |
| C/RSF24P + pDDH | 0.73 | 1.80 |
| C/RSF24P + plysA | 0.69 | 1.70 |

It was found that lysC* had an effect on the improvement in L-lysine productivity even in the case of the C strain with transformed dapA*, and the reaction participated by lysC* was the second rate determining step.

(3) Identification of the Third Rate Determining Step

The plasmid RSFD80 containing dapA* and lysC* was introduced into the E. coli C strain, and plasmids containing genes of the L-lysine biosynthesis system were further introduced. Obtained transformants were cultivated in the medium for L-lysine production, and the production amount of L-lysine hydrochloride was measured. Results are shown in Table 20.

TABLE 20

| Bacterial strain | Production amount of L-lysine hydrochloride (g/l) | Yield versus sugar (%) |
|---|---|---|
| C/RSFD80 | 1.82 | 4.5 |
| C/RSFD80 + pppc | 1.74 | 4.3 |
| C/RSFD80 + paspC | 1.82 | 4.5 |
| C/RSFD80 + plysC | 1.91 | 4.7 |

TABLE 20-continued

| Bacterial strain | Production amount of L-lysine hydrochloride (g/l) | Yield versus sugar (%) |
|---|---|---|
| C/RSFD80 + plysC* | 1.74 | 4.3 |
| C/RSFD80 + pasd | 1.82 | 4.5 |
| C/RSFD80 + pdapA | 1.95 | 4.8 |
| C/RSFD80 + pdapA* | 1.91 | 4.7 |
| C/RSFD80 + pdapB | 2.31 | 5.7 |
| C/RSFD80 + pDDH | 2.15 | 5.3 |
| C/RSFD80 + plysA | 1.95 | 4.8 |

In the same manner as in the W3110 strain, only dapB had an effect on the improvement in L-lysine productivity, and it was found to be the third rate determining step.

(4) Identification of the Fourth Rate Determining Step

The plasmid pCAB1 containing dapA*, lysC* and dapB was introduced into the E. coli C strain, and plasmids containing genes of the L-lysine biosynthesis system were further introduced. Obtained transformants were cultivated in the L-lysine-producing medium, and the production amount of L-lysine hydrochloride was measured. Results are shown in Table 21.

TABLE 21

| Bacterial strain | Production amount of L-lysine hydrochloride (g/l) | Yield versus sugar (%) |
|---|---|---|
| C/pCAB1 | 2.31 | 5.7 |
| C/pCAB1 + pppc | 2.23 | 5.5 |
| C/pCAB1 + paspC | 2.35 | 5.8 |
| C/pCAB1 + plysC | 2.27 | 5.6 |
| C/pCAB1 + plysC* | 2.19 | 5.4 |
| C/pCAB1 + pasd | 2.23 | 5.5 |
| C/pCAB1 + pdapA | 2.31 | 5.7 |
| C/pCAB1 + pdapA* | 2.27 | 5.6 |
| C/pCAB1 + pdapB | 2.23 | 5.5 |
| C/pCAB1 + pDDH | 2.59 | 6.4 |
| C/pCAB1 + plysA | 2.19 | 5.4 |

In the same manner as in the W3110 strain, only DDH had an effect on the improvement in L-lysine productivity, and it was found to be the fourth rate determining step.

(5) Analysis of Rate Determining Steps Among dapC, dapD, dapE and dapF

Plasmid harboring the dapD, dapE or dapF genes were introduced, instead of DDH, into the E. coli C strain harboring pCAB1, and cultivation for L-lysine production was performed. Results are shown in Table 22.

TABLE 22

| Bacterial strain | Production amount of L-lysine hydrochloride (g/l) | Yield versus sugar (%) | Color of broth | Accumulation of SDAP |
|---|---|---|---|---|
| C/pCAB1 | 2.31 | 5.7 | brown | + |
| C/pCAB1 + pdapD | 2.43 | 6.0 | yellow | + |
| C/pCAB1 + pdapE | 2.35 | 5.8 | brown | − |
| C/pCAB1 + pdapF | 2.23 | 5.5 | brown | + |
| C/pCABDE1 | 2.59 | 6.4 | yellow | − |
| C/pCABDE1 + pdapF | 2.43 | 6.0 | yellow | − |
| C/pCABD2 | 2.59 | 6.4 | yellow | − |

It was found that the two steps of dapD and dapE also concerned the rate determining in the C strain in the same manner as in the W3110 strain.

As described above, the strains of K-12 and C belonging to the different series had the same rate determining order.

Thus it is believed that the entire species of *E. coli* can be applied with the concept that the L-lysine productivity can be improved in a stepwise manner by performing introduction of dapA* and lysC* and enhancement of dapB and DDH (or dapD and dapE) in this order.

Industrial Applicability

According to the present invention, there has been obtained a DDPS mutant gene originating from a bacterium belonging to the genus Escherichia in which feedback inhibition by L-lysine is sufficiently desensitized. An L-lysine-producing bacterium more improved than those in the prior art has been able to be obtained by introducing the gene into a bacterium belonging to the genus Escherichia harboring an aspartokinase in which feedback inhibition by L-lysine is desensitized.

Further, the L-lysine productivity can be improved in a stepwise manner by enhancing dapB and DDH (or dapD and dapE) of the aforementioned L-lysine-producing bacterium in this order.

What is claimed is:

1. An isolated DNA coding for a dihydrodipicolinate synthase originating from a bacterium belonging to the genus Escherichia, wherein the dihydrodipicolinate synthase has a mutation which desensitizes feedback inhibition by L-lysine, wherein the mutation is selected from the group consisting of (a) a mutation to replace the alanine residue at the 81st position as counted from the N-terminal in the amino acid sequence of the dihydrodipicolinate synthase of SEQ ID NO: 4 with another amino acid residue, (b) a mutation to replace the histidine residue at the 118th position as counted from the N-terminal in the amino acid sequence of the dihydrodipicolinate synthase of SEQ ID NO: 4 with another amino acid residue, and (c) a mutation to replace the alanine residue at the 81st position as counted from the N-terminal in the amino acid sequence of the dihydrodipicolinate synthase of SEQ ID NO: 4 with another amino acid residue and replace the histidine residue at the 118th position as counted from the N-terminal in the amino acid sequence of the dihydrodipicolinate synthase of SEQ ID NO: 4 with another amino acid residue, (d) a mutation to replace the alanine residue corresponding to the 81st position as counted from the N-terminal in the amino acid sequence of the dihydrodipicolinate synthase of SEQ ID NO: 4 with another amino acid residue, (e) a mutation to replace the histidine residue corresponding to the 118th position as counted from the N-terminal in the amino acid sequence of the dihydrodipicolinate synthase of SEQ ID NO: 4 with another amino acid residue, and (f) a mutation to replace the alanine residue corresponding to the 81st position as counted from the N-terminal in the amino acid sequence of the dihydrodipicolinate synthase of SEQ ID NO: 4 with another amino acid residue and replace the histidine residue corresponding to the 118th position as counted from the N-terminal in the amino acid sequence of the dihydrodipicolinate synthase of SEQ ID NO: 4 with another amino acid residue.

2. The isolated DNA of claim 1, wherein the mutation to desensitize feedback inhibition by L-lysine is selected from the group consisting of (a) a mutation to replace the alanine residue at the 81st position as counted from the N-terminal in the amino acid sequence of the dihydrodipicolinate synthase of SEQ ID NO: 4 with a valine residue, (b) a mutation to replace the histidine residue at the 118th position as counted from the N-terminal in the amino acid sequence of the dihydrodipicolinate synthase of SEQ ID NO: 4 with a tyrosine residue, and (c) a mutation to replace the alanine residue at the 81$^{st}$ position as counted from the N-terminal in the amino acid sequence of the dihydrodipicolinate synthase of SEQ ID NO: 4 with a valine residue and replace the 118th histidine residue as counted from the N-terminal in the amino acid sequence of the dihydrodipicolinate synthase of SEQ ID NO: 4 with a tyrosine residue, (d) a mutation to replace the alanine residue corresponding to the 81st position as counted from the N-terminal in the amino acid sequence of the dihydrodipicolinate synthase of SEQ ID NO: 4 with a valine residue, (e) a mutation to replace the histidine residue corresponding to the 118th position as counted from the N-terminal in the amino acid sequence of the dihydrodipicolinate synthase of SEQ ID NO: 4 with a tyrosine residue, and (f) a mutation to replace the alanine residue corresponding to the 81$^{st}$ position as counted from the N-terminal in the amino acid sequence of the dihydrodipicolinate synthase of SEQ ID NO: 4 with a valine residue and replace the histidine residue corresponding to the 118th residue as counted from the N-terminal in the amino acid sequence of the dihydrodipicolinate synthase of SEQ ID NO: 4 with a tyrosine residue.

3. A bacterium belonging the genus Escherichia which is transformed with a DNA coding for a dihydrodipicolinate synthase originating from a bacterium belonging to the genus Escherichia and having mutation to desensitize feedback inhibition by L-lysine, wherein the mutation is selected from the group consisting of (a) a mutation to replace the alanine residue at the 81st position as counted from the N-terminal in the amino acid sequence of the dihydrodipicolinate synthase of SEQ ID NO: 4 with another amino acid residue, (b) a mutation to replace the histidine residue at the 118th position as counted from the N-terminal in the amino acid sequence of the dihydrodipicolinate synthase of SEQ ID NO: 4 with another amino acid residue, and (c) a mutation to replace the alanine residue at the 81st position as counted from the N-terminal in the amino acid sequence of the dihydrodipicolinate synthase of SEQ ID NO: 4 with another amino acid residue and replace the histidine residue at the 118th position as counted from the N-terminal in the amino acid sequence of the dihydrodipicolinate synthase of SEQ ID NO: 4 with another amino acid residue, (d) a mutation to replace the alanine residue corresponding to the 81st position as counted from the N-terminal in the amino acid sequence of the dihydrodipicolinate synthase of SEQ ID NO: 4 with another amino acid residue, (e) a mutation to replace the histidine residue corresponding to the 118th position as counted from the N-terminal in the amino acid sequence of the dihydrodipicolinate synthase of SEQ ID NO: 4 with another amino acid residue, and (f) a mutation to replace the alanine residue corresponding to the 81st position as counted from the N-terminal in the amino acid sequence of the dihydrodipicolinate synthase of SEQ ID NO: 4 with another amino acid residue and replace the histidine residue corresponding to the 118th position as counted from the N-terminal in the amino acid sequence of the dihydrodipicolinate synthase of SEQ ID NO: 4 with another amino acid residue.

4. The bacterium of claim 3, wherein the mutation is selected from the group consisting of (a) a mutation to replace the alanine residue at the 81st position as counted from the N-terminal in the amino acid sequence of the dihydrodipicolinate synthase of SEQ ID NO: 4 with a valine residue, (b) a mutation to replace the histidine residue at the 118th position as counted from the N-terminal in the amino acid sequence of the dihydrodipicolinate synthase of SEQ ID NO: 4 with a tyrosine residue, and (c) a mutation to replace the alanine residue at the 81st position as counted from the N-terminal in the amino acid sequence of the dihydrodipicolinate synthase of SEQ ID NO: 4 with a valine residue and replace the histidine residue at the 118th position as counted from the N-terminal in the amino acid sequence of the dihydrodipicolinate synthase of SEQ ID NO: 4 with a tyrosine residue, (d) a mutation to replace the alanine residue corresponding to the 81st position as counted from the N-terminal in the amino acid sequence of the dihydrodipicolinate synthase of SEQ ID NO: 4 with a valine residue, (e) a mutation to replace the histidine residue corresponding to the 118th position as counted from the N-terminal in the amino acid sequence of the dihydrodipicolinate synthase of SEQ ID NO: 4 with a tyrosine residue, and (f) a mutation to replace the alanine residue corresponding to the 81st position as counted from the N-terminal in the amino acid sequence of the dihydrodipicolinate synthase of SEQ ID NO: 4 with a valine residue and replace the histidine residue corresponding to the 118th position as counted from the N-terminal in the amino acid sequence of the dihydrodipicolinate synthase of SEQ ID NO: 4 with a tyrosine residue.

5. The bacterium of claim 3, further harboring an aspartokinase which is desensitized to feedback inhibition by L-lysine.

6. The bacterium of claim 5, which is obtained by introducing, into its cells, a DNA coding for an aspartokinase III originating from a bacterium belonging to the genus Escherichia, wherein the aspartokinase III has a mutation which desensitizes feedback inhibition by L-lysine.

7. The bacterium of claim 6, wherein the mutation is selected from the group consisting of (a) a mutation to replace the glycine residue at the 323rd position as counted from the N-terminal in the amino acid sequence of the aspartokinase III of SEQ ID NO: 8 with another amino acid residue, (b) a mutation to replace the glycine residue at the 323rd position as counted from the N-terminal in the amino acid sequence of the aspartokinase III of SEQ ID NO:8 with another amino acid residue and replace the glycine residue at the 408th position as counted from the N-terminal in the amino acid sequence of the aspartokinase III of SEQ ID NO: 8 with another amino acid residue, (c) a mutation to replace the glycine residue at the 34th position as counted from the N-terminal in the amino acid sequence of the aspartokinase III of SEQ ID NO: 8 with another amino acid residue and replace the glycine residue at the 323rd position as counted from the N-terminal in the amino acid sequence of the aspartokinase III of SEQ ID NO: 8 with another amino acid residue, (d) a mutation to replace the leucine residue at the 325th position as counted from the N-terminal in the amino acid sequence of the aspartokinase III of SEQ ID NO: 8 with another amino acid residue, (e) a mutation to replace the methionine residue at the 318th position as counted from the N-terminal in the amino acid sequence of the aspartokinase III of SEQ ID NO: 8 with another amino acid residue, (f) a mutation to replace the methionine residue at the 318th position as counted from the N-terminal in the amino acid sequence of the aspartokinase III of SEQ ID NO: 8 with another amino acid residue and replace the valine residue at the 349th position as counted from the N-terminal in the amino acid sequence of the aspartokinase III of SEQ ID NO: 8 with another amino acid residue, (g) a mutation to replace the serine residue at the 345th position as counted from the N-terminal in the amino acid sequence of the aspartokinase III of SEQ ID NO: 8 with another amino acid residue, (h) a mutation to replace the valine residue at the 347th position as counted from the N-terminal in the amino acid sequence of the aspartokinase III of SEQ ID NO: 8 with another amino acid residue, (i) a mutation to replace the threonine residue at the 352nd position as counted from the N-terminal in the amino acid sequence of the aspartokinase III of SEQ ID NO: 8 with another amino acid residue, (j) a mutation to replace the threonine residue at the 352nd position as counted from the N-terminal in the amino acid sequence of the aspartokinase III of SEQ ID NO: 8 with another amino acid residue and replace the serine residue at the 369th position as counted from the N-terminal in the amino acid sequence of the aspartokinase III of SEQ ID NO: 8 with another amino acid residue, (k) a mutation to replace the glutamic acid residue at the 164th position as counted from the N-terminal in the amino acid sequence of the aspartokinase III of SEQ ID NO: 8 with another amino acid residue, and (l) a mutation to replace the methionine residue at the 417th position as counted from the N-terminal in the amino acid sequence of the aspartokinase III of SEQ ID NO: 8 with another amino acid residue and replace the cysteine residue at the 419th position as counted from the N-terminal in the amino acid sequence of the aspartokinase III of SEQ ID NO: 8 with another amino acid residue, (m) a mutation to replace the glycine residue corresponding to the 323rd position as counted from the N-terminal in the amino acid sequence of the aspartokinase III of SEQ ID NO: 8 with another amino acid residue, (n) a mutation to replace the glycine residue corresponding to the 323rd position as counted from the N-terminal in the amino acid sequence of the aspartokinase III of SEQ ID NO:8 with another amino acid residue and replace the glycine residue corresponding to the 408th position as counted from the N-terminal in the amino acid sequence of the aspartokinase III of SEQ ID NO: 8 with another amino acid residue, (o) a mutation to replace the glycine residue corresponding to the 34th position as counted from the N-terminal in the amino acid sequence of the aspartokinase III of SEQ ID NO:8 with another amino acid residue and replace the glycine residue corresponding to the 323rd position as counted from the N-terminal in the amino acid sequence of the aspartokinase III of SEQ ID NO: 8 with another amino acid residue, (p) a mutation to replace the leucine residue corresponding to the 325th position as counted from the N-terminal in the amino acid sequence of the aspartokinase III of SEQ ID NO: 8 with another amino acid residue, (q) a mutation to replace the methionine residue corresponding to the 318th position as counted from the N-terminal in the amino acid sequence of the aspartokinase III of SEQ ID NO: 8 with another amino acid residue, (r) a mutation to replace the methionine residue corresponding to the 318th position as counted from the N-terminal in the amino acid sequence of the aspartokinase III of SEQ ID NO: 8 with another amino acid residue and replace the valine residue corresponding to the 349th position as counted from the N-terminal in the amino acid sequence of the aspartokinase III of SEQ ID NO: 8 with another amino acid residue, (s) a mutation to replace the serine residue corresponding to the 345th position as counted from the N-terminal in the amino acid sequence of the aspartokinase III of SEQ ID NO: 8 with another amino acid residue, (t) a mutation to replace the valine residue corresponding to the 347th position as counted from the N-terminal in the amino acid sequence of the aspartokinase III of SEQ ID NO: 8 with another amino acid residue, (u) a mutation to replace the threonine residue corresponding to the 352nd position as counted from the N-terminal in the amino acid sequence of the aspartokinase III of SEQ ID NO: 8 with another amino acid residue, (v) a mutation to replace the threonine residue corresponding to the 352nd position as counted from the N-terminal in the amino acid sequence of the aspartokinase III of SEQ ID NO: 8 with another amino acid residue and replace the serine residue corresponding to the 369th position as counted from the N-terminal in the amino acid sequence of the aspartokinase III of SEQ ID NO: 8 with another amino acid residue, (w) a mutation to replace the glutamic acid residue corresponding to the 164th position as counted from the N-terminal in the amino acid sequence of the aspartokinase III of SEQ ID NO: 8 with another amino acid residue, and (x) a mutation to replace the methionine residue corresponding to the 417th position as counted from the N-terminal in the amino acid sequence of the aspartokinase III of SEQ ID NO: 8 with another amino acid residue and replace the cysteine residue corresponding to the 419th position as counted from the N-terminal in the amino acid sequence of the aspartokinase III of SEQ ID NO: 8 with another amino acid residue.

8. The bacterium of claim 7, wherein the mutation is selected from the group consisting of (a) a mutation to replace the glycine residue at the 323rd position as counted from the N-terminal in the amino acid sequence of the aspartokinase III of SEQ ID NO: 8 with an aspartic acid residue, (b) a mutation to replace the glycine residue at the 323rd position as counted from the N-terminal in the amino acid sequence of the aspartokinase III of SEQ ID NO: 8 with an aspartic acid residue and replace the glycine residue at the 408th position as counted from the N-terminal in the amino acid sequence of the aspartokinase III of SEQ ID NO: 8 with an aspartic acid residue, (c) a mutation to replace the arginine residue at the 34th position as counted from the N-terminal in the amino acid sequence of the aspartokinase III of SEQ ID NO:8 with a cysteine residue and replace the glycine residue at the 323rd position as counted from the N-terminal in the amino acid sequence of the aspartokinase III of SEQ ID NO: 8 with an aspartic acid residue, (d) a mutation to replace the leucine residue at the 325th position as counted from the N-terminal in the amino acid sequence of the aspartokinase III of SEQ ID NO: 8 with a phenylalanine residue, (e) a mutation to replace the methionine residue at the 318th position as counted from the N-terminal in the amino acid sequence of the aspartokinase III of SEQ ID NO: 8 with an isoleucine residue, (f) a mutation to replace the methionine residue at the 318th position as counted from the N-terminal in the amino acid sequence of the aspartokinase III of SEQ ID NO: 8 with an isoleucine residue and replace the valine residue at the 349th position as counted from the N-terminal in the amino acid sequence of the aspartokinase III of SEQ ID NO: 8 with a methionine residue, (g) a mutation to replace the serine residue at the 345th position as counted from the N-terminal in the amino acid sequence of the aspartokinase III of SEQ ID NO: 8 with a leucine residue, (h) a mutation to replace the valine residue at the 347th position as counted from the N-terminal in the amino acid sequence of the aspartokinase III of SEQ ID NO: 8 with a valine residue, (i) a mutation to replace the threonine residue at the 352nd position as counted from the N-terminal in the amino acid sequence of the aspartokinase III of SEQ ID NO: 8 with an isoleucine residue, (j) a mutation to replace the threonine residue at the 352nd position as counted from the N-terminal in the amino acid sequence of the aspartokinase III of SEQ ID NO: 8 with an isoleucine residue and replace the serine residue at the 369th position as counted from the N-terminal in the amino acid sequence of the aspartokinase III of SEQ ID NO: 8 with a phenylalanine residue, (k) a mutation to replace the glutamic acid residue at the 164th position as counted from the N-terminal in the amino acid sequence of the aspartokinase III of SEQ ID NO: 8 with a lysine residue, and (l) a mutation to replace the methionine residue at the 417th position as counted from the N-terminal in the amino acid sequence of the aspartokinase III of SEQ ID NO: 8 with an isoleucine residue and replace the cysteine residue at the 419th position as counted from the N-terminal in the amino acid sequence of the aspartokinase III of SEQ ID NO: 8 with a tyrosine residue, (m) a mutation to replace the glycine residue corresponding to the 323rd position as counted from the N-terminal in the amino acid sequence of the aspartokinase III of SEQ ID NO: 8 with an aspartic acid residue, (n) a mutation to replace the glycine residue corresponding to the 323rd position as counted from the N-terminal in the amino acid sequence of the aspartokinase III of SEQ ID NO: 8 with an aspartic acid residue and replace the glycine residue corresponding to the 408th position as counted from the N-terminal in the amino acid sequence of the aspartokinase III of SEQ ID NO: 8 with an aspartic acid residue, (o) a mutation to replace the arginine residue corresponding to the 34th position as counted from the N-terminal in the amino acid sequence of the aspartokinase III of SEQ ID NO:8 with a cysteine residue and replace the glycine residue corresponding to the 323rd position as counted from the N-terminal in the amino acid sequence of the aspartokinase III of SEQ ID NO: 8 with an aspartic acid residue, (p) a mutation to replace the leucine residue corresponding to the 325th position as counted from the N-terminal in the amino acid sequence of the aspartokinase III of SEQ ID NO: 8 with a phenylalanine residue, (q) a mutation to replace the methionine residue corresponding to the 318th position as counted from the N-terminal in the amino acid sequence of the aspartokinase III of SEQ ID NO: 8 with an isoleucine residue, (r) a mutation to replace the methionine residue corresponding to the 318th position as counted from the N-terminal in the amino acid sequence of the aspartokinase III of SEQ ID NO: 8 with an isoleucine residue and replace the valine residue corresponding to the 349th position as counted from the N-terminal in the amino acid sequence of the aspartokinase III of SEQ ID NO: 8 with a methionine residue, (s) a mutation to replace the serine residue corresponding to the 345th position as counted from the N-terminal in the amino acid sequence of the aspartokinase III of SEQ ID NO: 8 with a leucine residue, (t) a mutation to replace the valine residue corresponding to the 347th position as counted from the N-terminal in the amino acid sequence of the aspartokinase III of SEQ ID NO: 8 with a valine residue, (u) a mutation to replace the threonine residue corresponding to the 352nd position as counted from the N-terminal in the amino acid sequence of the aspartokinase III of SEQ ID NO: 8 with an isoleucine residue, (v) a mutation to replace the threonine residue corresponding to the 352nd position as counted from the N-terminal in the amino acid sequence of the aspartokinase III of SEQ ID NO: 8 with an isoleucine residue and replace the serine residue corresponding to the 369th position as counted from the N-terminal in the amino acid sequence of the aspartokinase III of SEQ ID NO: 8 with a phenylalanine residue, (w) a mutation to replace the glutamic acid residue corresponding to the 164th position as counted from the N-terminal in the amino acid sequence of the aspartokinase III of SEQ ID NO: 8 with a lysine residue, and (x) a mutation to replace the methionine residue corresponding to the 417th position as counted from the N-terminal in the amino acid sequence of the aspartokinase III of SEQ ID NO: 8 with an isoleucine residue and replace the cysteine residue corresponding to the 419th position as counted from the N-terminal in the amino acid sequence of the aspartokinase III of SEQ ID NO: 8 with a tyrosine residue.

9. The bacterium of claim 5, wherein a dihydrodipicolinate reductase gene is enhanced.

10. The bacterium of claim 9, transformed with a recombinant DNA constructed by ligating the dihydrodipicolinate reductase gene with a vector autonomously replicable in cells of bacteria belonging to the genus Escherichia.

11. The bacterium of claim 9, into which an enhanced diaminopimelate dehydrogenase gene originating from coryneform bacterium has been introduced.

12. The of claim 11, transformed with a recombinant DNA constructed by ligating the diaminopimelate dehydrogenase gene originating from a coryneform bacterium with a vector autonomously replicable in cells of bacteria belonging to the genus Escherichia.

13. The bacterium of claim 9, wherein a succinyldiaminopimelate transaminase gene and a succinyldiaminopimelate transaminase gene and a succinyldiaminopimelate deacylase gene are enhanced.

14. The bacterium of claim 13, transformed with a single recombinant DNA or two recombinant DNA's constructed by ligating the succinyldiaminopimelate transaminase gene and the succinyldiaminopimelate deacylase gene with an identical vector or different vectors autonomously replicable in cells of bacteria belonging to the genus Escherichia.

15. A method of producing L-lysine, comprising:
cultivating the bacterium of claim 3 in a suitable culture medium, producing and accumulating L-lysine in the culture thereof, and collecting L-lysine from the culture.

16. A bacterium belonging the genus Escherichia which is transformed with a DNA coding for a dihydrodipicolinate synthase originating from a bacterium belonging to the genus Escherichia and having mutation to desensitize feedback inhibition by L-lysine, and further harboring an aspartokinase which is desensitized to feedback inhibition by L-lysine, and wherein a dihydrodipicolinate reductase gene is enhanced.

17. The bacterium of claim 16, transformed with a recombinant DNA constructed by ligating the dihydrodipicolinate reductase gene with a vector autonomously replicable in cells of bacteria belonging to the genus Escherichia.

18. The bacterium of claim 16, into which an enhanced diaminopimelate dehydrogenase gene originating from coryneform bacterium has been introduced.

19. The of claim 18, transformed with a recombinant DNA constructed by ligating the diaminopimelate dehydrogenase gene originating from a coryneform bacterium with a vector autonomously replicable in cells of bacteria belonging to the genus Escherichia.

20. The bacterium of claim 16, wherein a succinyldiaminopimelate transaminase gene and a succinyldiaminopimelate transaminase gene and a succinyldiaminopimelate deacylase gene are enhanced.

21. The bacterium of claim 20, transformed with a single recombinant DNA or two recombinant DNA's constructed by ligating the succinyldiaminopimelate transaminase gene and the succinyldiaminopimelate deacylase gene with an identical vector or different vectors autonomously replicable in cells of bacteria belonging to the genus Escherichia.

22. A method of producing L-lysine, comprising:
cultivating the bacterium of claim 16 in a suitable culture medium, producing and accumulating L-lysine in the culture thereof, and collecting L-lysine from the culture.

* * * * *

UNITED STATES PATENT AND TRADEMARK OFFICE
CERTIFICATE OF CORRECTION

PATENT NO. : 6,040,160
DATED : March 21, 2000
INVENTOR(S) : Kojima et al.

It is certified that error appears in the above-identified patent and that said Letters Patent is hereby corrected as shown below:

Column 67,
Line 34-35, "succinyldiaminopimelate transaminase" should read
-- tetrahydrodipicolinate succinylase --.
Lines 35-36, delete "and a succinyldiaminopimelate transaminase gene".
Line 40, "succinyldiaminopimelate transaminase" should read
-- tetrahydrodipicolinate succinylase --.

Column 68,
Line 3, "producing and accumulating" should read -- to produce and accumulate --.
Lines 26-27, "succinyldiaminopimelate transaminase" should read
-- tetrahydrodipicolinate succinylase --.
Lines 27-28, delete "and a succinyldiaminopimelate transaminase gene".
Line 32, "succinyldiaminopimelate transaminase" should read
-- tetrahydrodipicolinate succinylase --.
Line 38, "producing and accumulating" should read -- to produce and accumulate --.

Signed and Sealed this

Second Day of July, 2002

Attest:

JAMES E. ROGAN
Attesting Officer     Director of the United States Patent and Trademark Office